(12) United States Patent
Zepp et al.

(10) Patent No.: US 9,994,443 B2
(45) Date of Patent: Jun. 12, 2018

(54) MODIFIED NICOTINIC COMPOUNDS AND RELATED METHODS

(75) Inventors: Charles Zepp, Hardwick, MA (US); Yun Gao, Southborough, MA (US)

(73) Assignee: Selecta Biosciences, Inc., Watertown, MA (US)

( * ) Notice: Subject to any disclaimer, the term of this patent is extended or adjusted under 35 U.S.C. 154(b) by 0 days. days.

(21) Appl. No.: 13/289,211

(22) Filed: Nov. 4, 2011

(65) Prior Publication Data

US 2012/0114677 A1 May 10, 2012

Related U.S. Application Data

(60) Provisional application No. 61/410,597, filed on Nov. 5, 2010.

(51) Int. Cl.
*B82Y 5/00* (2011.01)
*C07D 401/04* (2006.01)
*C08G 73/02* (2006.01)
*C08G 65/26* (2006.01)
*C08G 65/329* (2006.01)
*C08G 65/333* (2006.01)
*A61K 39/00* (2006.01)
*A61K 39/385* (2006.01)
*A61K 47/60* (2017.01)
*A61K 47/59* (2017.01)

(52) U.S. Cl.
CPC ............ *B82Y 5/00* (2013.01); *A61K 39/0013* (2013.01); *A61K 39/385* (2013.01); *A61K 47/59* (2017.08); *A61K 47/60* (2017.08); *C07D 401/04* (2013.01); *C08G 65/2609* (2013.01); *C08G 65/2618* (2013.01); *C08G 65/329* (2013.01); *C08G 65/33317* (2013.01); *C08G 65/33396* (2013.01); *C08G 73/0206* (2013.01); *C08G 73/0233* (2013.01); *C08L 2203/02* (2013.01)

(58) Field of Classification Search
CPC .......... B82Y 5/00; A61K 47/60; A61K 47/59; A61K 39/0013; A61K 39/385; C07D 401/04; C08G 65/2609; C08G 65/2618; C08G 65/329; C08G 65/33317; C08G 65/33396; C08G 73/0206; C08G 73/0233; C08L 2203/02
See application file for complete search history.

(56) References Cited

U.S. PATENT DOCUMENTS

| | | |
|---|---|---|
| 3,996,355 A | 12/1976 | Lin et al. |
| 4,021,364 A | 5/1977 | Speiser et al. |
| 4,225,581 A | 9/1980 | Kreuter et al. |
| 4,950,432 A | 8/1990 | Mehta et al. |
| 5,175,296 A | 12/1992 | Gerster |
| 5,389,640 A | 2/1995 | Gerster et al. |
| 5,395,937 A | 3/1995 | Nikolaides et al. |
| 5,543,158 A | 8/1996 | Gref et al. |
| 5,578,325 A | 11/1996 | Domb et al. |
| 5,605,899 A | 2/1997 | Gerster et al. |
| 5,663,153 A | 9/1997 | Hutcherson et al. |
| 5,741,909 A | 4/1998 | Gerster et al. |
| 5,762,904 A | 6/1998 | Okada et al. |
| 5,871,747 A | 2/1999 | Gengoux-Sedlik |
| 5,876,727 A | 3/1999 | Swain et al. |
| 5,912,017 A | 6/1999 | Mathiowitz et al. |
| 5,928,647 A | 7/1999 | Rock |
| 5,939,100 A | 8/1999 | Albrechtsen et al. |
| 5,977,366 A | 11/1999 | Gerster et al. |
| 5,985,325 A | 11/1999 | Nagi |
| 5,989,591 A | 11/1999 | Nagi |
| 6,007,845 A | 12/1999 | Domb et al. |
| 6,039,969 A | 3/2000 | Tomai et al. |
| 6,043,224 A | 3/2000 | Lee et al. |
| 6,060,082 A | 5/2000 | Chen et al. |
| 6,083,505 A | 7/2000 | Miller et al. |
| 6,130,082 A | 10/2000 | Majarian et al. |
| 6,132,723 A | 10/2000 | Malcolm |
| 6,194,388 B1 | 2/2001 | Krieg et al. |
| 6,197,229 B1 | 3/2001 | Ando et al. |
| 6,207,646 B1 | 3/2001 | Krieg et al. |
| 6,218,371 B1 | 4/2001 | Krieg et al. |
| 6,232,082 B1 | 5/2001 | Ennifar et al. |
| 6,239,116 B1 | 5/2001 | Krieg et al. |
| 6,245,776 B1 | 6/2001 | Skwierczynski et al. |
| 6,254,890 B1 | 7/2001 | Hirosue et al. |
| 6,288,040 B1 | 9/2001 | Muller et al. |
| 6,329,381 B1 | 12/2001 | Kurimoto et al. |
| 6,348,462 B1 | 2/2002 | Gerster et al. |
| 6,365,187 B2 | 4/2002 | Mathiowitz et al. |
| 6,387,397 B1 | 5/2002 | Chen et al. |

(Continued)

FOREIGN PATENT DOCUMENTS

| | | |
|---|---|---|
| CA | 2 649 149 A1 | 10/2007 |
| CN | 1692943 A | 11/2005 |

(Continued)

OTHER PUBLICATIONS

International Preliminary Report on Patentability for PCT/US2011/059350 dated May 16, 2013.
International Search Report and Written Opinion for PCT/US2011/059350 dated Mar. 13, 2012.
[No Author Listed] R 848 Vanguard Medica phase change II, Europe. Highbeam Business. R & D Focus Drug News. Mar. 6, 2000. http://business.highbeam.com/436989/article-1G1-59732297/r-848-vanguard-medica-phase-change-ii-europe [last Accessed Feb. 16, 2011]. 1 page.

(Continued)

*Primary Examiner* — Timothy R Rozof
(74) *Attorney, Agent, or Firm* — Wolf, Greenfield & Sacks, P.C.

(57) ABSTRACT

Provided herein are compounds and related composition and methods that may be used to raise an antibody response to nicotinic compounds, in some embodiments.

29 Claims, No Drawings

(56) References Cited

U.S. PATENT DOCUMENTS

| | | | |
|---|---|---|---|
| 6,465,654 B2 | 10/2002 | Gerster et al. | |
| 6,486,168 B1 | 11/2002 | Skwierczynski et al. | |
| 6,518,031 B2 | 2/2003 | Ennifar et al. | |
| 6,558,951 B1 | 5/2003 | Tomai et al. | |
| 6,565,859 B1 | 5/2003 | Fricker et al. | |
| 6,569,463 B2 | 5/2003 | Patel et al. | |
| 6,585,980 B1 | 7/2003 | Chan et al. | |
| 6,605,299 B2 | 8/2003 | Zalipsky | |
| 6,608,201 B2 | 8/2003 | Gerster et al. | |
| 6,610,319 B2 | 8/2003 | Tomai et al. | |
| 6,610,713 B2 | 8/2003 | Tracey | |
| 6,656,469 B1 | 12/2003 | Svensson et al. | |
| 6,686,472 B2 | 2/2004 | Gerster et al. | |
| 6,693,086 B1 | 2/2004 | Dow et al. | |
| 6,696,076 B2 | 2/2004 | Tomai et al. | |
| 6,699,474 B1 | 3/2004 | Cerny | |
| 6,723,429 B2 | 4/2004 | Bengs et al. | |
| 6,747,156 B2 | 6/2004 | Johansson et al. | |
| 6,767,702 B2 | 7/2004 | Mirkin et al. | |
| 6,773,891 B2 | 8/2004 | Ennifar et al. | |
| 6,790,961 B2 | 9/2004 | Gerster et al. | |
| 6,800,296 B1 | 10/2004 | Langer et al. | |
| 6,800,624 B2 | 10/2004 | Crooks et al. | |
| 6,811,975 B2 | 11/2004 | Cook et al. | |
| 6,849,270 B2 | 2/2005 | Zalipsky | |
| 7,037,523 B2 | 5/2006 | Hussain et al. | |
| 7,097,837 B2 | 8/2006 | Nielsen et al. | |
| 7,132,475 B2 | 11/2006 | Hubbell et al. | |
| 7,149,574 B2 | 12/2006 | Yun et al. | |
| 7,192,725 B2 | 3/2007 | Chan et al. | |
| 7,223,398 B1 | 5/2007 | Tuck et al. | |
| 7,238,368 B2 | 7/2007 | Zalipsky et al. | |
| 7,247,502 B2 | 7/2007 | Ennifar et al. | |
| 7,250,403 B2 | 7/2007 | Van Nest et al. | |
| 7,250,499 B2 | 7/2007 | Mirkin et al. | |
| 7,262,286 B2 | 8/2007 | Kandimalla et al. | |
| 7,276,489 B2 | 10/2007 | Agrawal et al. | |
| 7,285,289 B2 | 10/2007 | Nagy et al. | |
| 7,357,936 B1 | 4/2008 | Garcon | |
| 7,363,076 B2 | 4/2008 | Yun et al. | |
| 7,375,180 B2 | 5/2008 | Gorden et al. | |
| 7,375,234 B2 | 5/2008 | Sharpless et al. | |
| 7,387,271 B2 | 6/2008 | Noelle et al. | |
| 7,390,780 B2 | 6/2008 | Huang et al. | |
| 7,427,629 B2 | 9/2008 | Kedl et al. | |
| 7,452,541 B2 | 11/2008 | Bachmann et al. | |
| 7,501,134 B2 | 3/2009 | O'Hagan et al. | |
| 7,517,520 B2 | 4/2009 | Manolova et al. | |
| 7,550,441 B2 | 6/2009 | Farokhzad et al. | |
| 7,566,703 B2 | 7/2009 | Krieg et al. | |
| 7,727,969 B2 | 6/2010 | Farokhzad et al. | |
| 7,776,620 B2 | 8/2010 | Ennifar et al. | |
| 7,842,312 B2 | 11/2010 | Burgermeister et al. | |
| 8,367,113 B2 | 2/2013 | Gu et al. | |
| 8,629,151 B2 | 1/2014 | Zepp et al. | |
| 8,652,487 B2 | 2/2014 | Maldonado et al. | |
| 9,006,254 B2 | 4/2015 | Zepp et al. | |
| 9,066,978 B2 | 6/2015 | Ilyinskii et al. | |
| 9,265,815 B2 | 2/2016 | Fraser et al. | |
| 9,289,476 B2 | 3/2016 | Fraser et al. | |
| 9,289,477 B2 | 3/2016 | Fraser et al. | |
| 9,295,718 B2 | 3/2016 | Fraser et al. | |
| 9,764,031 B2 | 9/2017 | Ilyinskii et al. | |
| 2003/0009029 A1 | 1/2003 | Buchholz et al. | |
| 2003/0035804 A1 | 2/2003 | D'Amico et al. | |
| 2003/0054042 A1 | 3/2003 | Liversidge et al. | |
| 2003/0133988 A1 | 7/2003 | Fearon et al. | |
| 2003/0165478 A1 | 9/2003 | Sokoll | |
| 2004/0022840 A1 | 2/2004 | Nagy et al. | |
| 2004/0059094 A1 | 3/2004 | Bachmann et al. | |
| 2004/0109894 A1 | 6/2004 | Shefer et al. | |
| 2004/0141958 A1 | 7/2004 | Steinaa et al. | |
| 2004/0247680 A1 | 12/2004 | Farokhzad et al. | |
| 2004/0258698 A1 | 12/2004 | Wightman et al. | |
| 2005/0037075 A1 | 2/2005 | Farokhzad et al. | |
| 2005/0042298 A1 | 2/2005 | Pardridge et al. | |
| 2005/0079152 A1 | 4/2005 | Bot et al. | |
| 2005/0089524 A1 | 4/2005 | Sanderson et al. | |
| 2005/0107322 A1 | 5/2005 | O'Hagan et al. | |
| 2005/0192248 A1 | 9/2005 | Tsuji et al. | |
| 2005/0233948 A1 | 10/2005 | D'Amico et al. | |
| 2005/0239734 A1 | 10/2005 | Uhlmann et al. | |
| 2005/0281845 A1 | 12/2005 | Bachmann et al. | |
| 2006/0002852 A1 | 1/2006 | Saltzman et al. | |
| 2006/0045868 A1 | 3/2006 | Meezan et al. | |
| 2006/0111271 A1 | 5/2006 | Cerny et al. | |
| 2006/0142202 A1 | 6/2006 | Alkan et al. | |
| 2006/0234912 A1 | 10/2006 | Wang et al. | |
| 2006/0241076 A1 | 10/2006 | Uhlmann et al. | |
| 2007/0014807 A1 | 1/2007 | Maida, III | |
| 2007/0020620 A1 | 1/2007 | Finn et al. | |
| 2007/0116768 A1 | 5/2007 | Chorny et al. | |
| 2007/0166384 A1 | 7/2007 | Zarraga et al. | |
| 2007/0184068 A1 | 8/2007 | Renner et al. | |
| 2007/0264481 A1 | 11/2007 | DeSimone et al. | |
| 2008/0014281 A1 | 1/2008 | Shibata et al. | |
| 2008/0026000 A1 | 1/2008 | Ennifar | |
| 2008/0031899 A1 | 2/2008 | Reddy et al. | |
| 2008/0050450 A1 | 2/2008 | Arnold et al. | |
| 2008/0081074 A1 | 4/2008 | Gu et al. | |
| 2008/0145441 A1 | 6/2008 | Penades et al. | |
| 2008/0171059 A1 | 7/2008 | Howland et al. | |
| 2008/0207550 A1 | 8/2008 | Fearon et al. | |
| 2008/0213377 A1 | 9/2008 | Bhatia et al. | |
| 2008/0234251 A1 | 9/2008 | Doherty et al. | |
| 2008/0268063 A1 | 10/2008 | Jon et al. | |
| 2008/0306050 A1 | 12/2008 | Doherty et al. | |
| 2009/0004118 A1 | 1/2009 | Nie et al. | |
| 2009/0011009 A1 | 1/2009 | Benita et al. | |
| 2009/0074828 A1 | 3/2009 | Alexis et al. | |
| 2009/0104268 A1 | 4/2009 | Himmler et al. | |
| 2009/0130210 A1 | 5/2009 | Raheja et al. | |
| 2009/0169636 A1 | 7/2009 | O'Hagan et al. | |
| 2009/0181402 A1 | 7/2009 | Finn et al. | |
| 2009/0238797 A1 | 9/2009 | Lang et al. | |
| 2009/0297609 A1 | 12/2009 | Shoichet et al. | |
| 2009/0297614 A1 | 12/2009 | Rademacher et al. | |
| 2009/0297621 A1 | 12/2009 | Lim et al. | |
| 2009/0298710 A1 | 12/2009 | Farokhzad et al. | |
| 2009/0324551 A1 | 12/2009 | Carson et al. | |
| 2009/0325292 A1 | 12/2009 | Baker et al. | |
| 2010/0068285 A1 | 3/2010 | Zale et al. | |
| 2010/0075995 A1 | 3/2010 | Biggadike et al. | |
| 2010/0092425 A1* | 4/2010 | von Andrian et al. | 424/85.2 |
| 2010/0098770 A1 | 4/2010 | Ramalingam et al. | |
| 2010/0104653 A1 | 4/2010 | Ludwig et al. | |
| 2010/0129392 A1* | 5/2010 | Shi | A61K 39/00 424/193.1 |
| 2010/0129439 A1 | 5/2010 | Alexis et al. | |
| 2010/0143453 A1 | 6/2010 | Schiffelers et al. | |
| 2010/0166876 A1 | 7/2010 | Singh et al. | |
| 2010/0172993 A1 | 7/2010 | Singh et al. | |
| 2010/0203142 A1 | 8/2010 | Zhang et al. | |
| 2010/0233231 A1 | 9/2010 | Labrecque et al. | |
| 2010/0233251 A1 | 9/2010 | Von Andrian et al. | |
| 2010/0303850 A1 | 12/2010 | Lipford et al. | |
| 2010/0316724 A1 | 12/2010 | Whitfield et al. | |
| 2010/0323019 A1 | 12/2010 | Lim et al. | |
| 2010/0323199 A1 | 12/2010 | Gu et al. | |
| 2011/0014281 A1 | 1/2011 | Aleksov et al. | |
| 2011/0020388 A1 | 1/2011 | Zepp et al. | |
| 2011/0027217 A1 | 2/2011 | Zepp et al. | |
| 2011/0027368 A1 | 2/2011 | Burgermeister et al. | |
| 2011/0052697 A1 | 3/2011 | Farokhzad et al. | |
| 2011/0110965 A1 | 5/2011 | Fraser et al. | |
| 2011/0171248 A1 | 7/2011 | Pittet et al. | |
| 2011/0223201 A1 | 9/2011 | Lipford et al. | |
| 2011/0262491 A1 | 10/2011 | Keegan et al. | |
| 2011/0272836 A1 | 11/2011 | Keegan et al. | |
| 2011/0293700 A1* | 12/2011 | Bratzler et al. | 424/450 |
| 2011/0293701 A1 | 12/2011 | Bratzler et al. | |
| 2011/0293723 A1 | 12/2011 | Bratzler et al. | |
| 2012/0027806 A1 | 2/2012 | Ilyinskii et al. | |
| 2012/0058153 A1 | 3/2012 | Ilyinskii et al. | |

(56) References Cited

U.S. PATENT DOCUMENTS

| | | |
|---|---|---|
| 2012/0058154 A1 | 3/2012 | Ilyinskii et al. |
| 2012/0064110 A1 | 3/2012 | Ilyinskii et al. |
| 2012/0070493 A1 | 3/2012 | Fraser et al. |
| 2012/0171229 A1 | 7/2012 | Zepp et al. |
| 2012/0244222 A1 | 9/2012 | Altreuter et al. |
| 2012/0276109 A1 | 11/2012 | Fraser et al. |
| 2012/0276133 A1 | 11/2012 | Maldonado et al. |
| 2012/0276134 A1 | 11/2012 | Fraser et al. |
| 2012/0276155 A1 | 11/2012 | Kishimoto et al. |
| 2012/0276156 A1 | 11/2012 | Fraser et al. |
| 2012/0276157 A1 | 11/2012 | Fraser et al. |
| 2012/0276158 A1 | 11/2012 | Fraser et al. |
| 2012/0276159 A1 | 11/2012 | Fraser et al. |
| 2012/0276160 A1 | 11/2012 | Maldonado et al. |
| 2012/0294888 A1 | 11/2012 | Kishimoto et al. |
| 2012/0301498 A1 | 11/2012 | Altreuter et al. |
| 2012/0301510 A1 | 11/2012 | Kishimoto et al. |
| 2013/0028857 A1 | 1/2013 | Gao et al. |
| 2013/0028941 A1 | 1/2013 | Altreuter et al. |
| 2013/0039954 A1 | 2/2013 | Pittet et al. |
| 2013/0058894 A1 | 3/2013 | Maldonado et al. |
| 2013/0058901 A1 | 3/2013 | Maldonado et al. |
| 2013/0058902 A1 | 3/2013 | Kishimoto et al. |
| 2013/0058963 A1 | 3/2013 | Maldonado et al. |
| 2013/0058970 A1 | 3/2013 | Kishimoto et al. |
| 2013/0058974 A1 | 3/2013 | Maldonado et al. |
| 2013/0058975 A1 | 3/2013 | Maldonado et al. |
| 2013/0058976 A1 | 3/2013 | Kishimoto et al. |
| 2013/0058977 A1 | 3/2013 | Maldonado et al. |
| 2013/0058978 A1 | 3/2013 | Maldonado et al. |
| 2013/0059009 A1 | 3/2013 | Kishimoto et al. |
| 2014/0030344 A1 | 1/2014 | Zepp et al. |
| 2014/0193453 A1 | 7/2014 | Zepp et al. |
| 2014/0199340 A1 | 7/2014 | Maldonado |
| 2014/0242173 A1 | 8/2014 | Zepp et al. |
| 2014/0328854 A1 | 11/2014 | Maldonado et al. |
| 2014/0328921 A1 | 11/2014 | Maldonado |
| 2014/0328922 A1 | 11/2014 | Maldonado |
| 2014/0328923 A1 | 11/2014 | Maldonado et al. |
| 2014/0328924 A1 | 11/2014 | Kishimoto |
| 2014/0356361 A1 | 12/2014 | Maldonado et al. |
| 2015/0320728 A1 | 11/2015 | Fraser et al. |
| 2015/0320856 A1 | 11/2015 | Altreuter et al. |
| 2015/0320870 A1 | 11/2015 | Maldonado |
| 2015/0320884 A1 | 11/2015 | Fraser et al. |
| 2015/0328300 A1 | 11/2015 | Zepp et al. |
| 2015/0328309 A1 | 11/2015 | Ilyinskii et al. |
| 2015/0328333 A1 | 11/2015 | Fraser et al. |
| 2015/0335762 A1 | 11/2015 | Fraser et al. |
| 2015/0359865 A1 | 12/2015 | Kishimoto |
| 2015/0374815 A1 | 12/2015 | Kishimoto et al. |
| 2016/0022650 A1 | 1/2016 | Fraser et al. |
| 2016/0030554 A1 | 2/2016 | Kishimoto et al. |
| 2016/0030555 A1 | 2/2016 | Kishimoto et al. |
| 2016/0067228 A1 | 3/2016 | Kishimoto et al. |
| 2016/0074372 A1 | 3/2016 | Kishimoto |
| 2016/0074427 A1 | 3/2016 | Kishimoto |
| 2016/0074531 A1 | 3/2016 | Kishimoto |
| 2016/0074532 A1 | 3/2016 | Kishimoto |
| 2016/0128986 A1 | 5/2016 | O'Neil et al. |
| 2016/0128987 A1 | 5/2016 | Griset et al. |
| 2016/0220501 A1 | 8/2016 | Fraser et al. |
| 2016/0243253 A1 | 8/2016 | Fraser et al. |
| 2016/0256401 A1 | 9/2016 | Fraser et al. |
| 2016/0279234 A1 | 9/2016 | Kishimoto et al. |
| 2017/0258927 A1 | 9/2017 | Johnston |

FOREIGN PATENT DOCUMENTS

| | | |
|---|---|---|
| EP | 0 636 031 B1 | 9/1996 |
| EP | 0 582 581 B1 | 5/1999 |
| EP | 1 140 091 B1 | 9/2005 |
| EP | 1 221 955 B9 | 11/2005 |
| EP | 1 752 141 A1 | 2/2007 |
| EP | 0 938 315 B1 | 7/2007 |
| WO | WO 92/15582 A1 | 9/1992 |
| WO | WO 97/47623 A1 | 12/1997 |
| WO | WO 98/14216 A2 | 4/1998 |
| WO | WO 98/37919 A1 | 9/1998 |
| WO | WO 98/40100 A1 | 9/1998 |
| WO | WO 98/52581 A1 | 11/1998 |
| WO | WO 99/56755 A1 | 11/1999 |
| WO | WO 99/61054 A1 | 12/1999 |
| WO | WO 00/06123 A1 | 2/2000 |
| WO | WO 00/50075 A2 | 8/2000 |
| WO | WO 01/68103 A2 | 9/2001 |
| WO | WO 2003/086280 A2 | 10/2003 |
| WO | WO 2004/009116 A2 | 1/2004 |
| WO | WO 2004/022594 A2 | 3/2004 |
| WO | WO 2004/053104 A2 | 6/2004 |
| WO | WO 2004/058179 A2 | 7/2004 |
| WO | WO 2005/042018 A2 | 5/2005 |
| WO | WO 2005/058282 A1 | 6/2005 |
| WO | WO 2005/097993 A2 | 10/2005 |
| WO | WO 2005/110013 A2 | 11/2005 |
| WO | WO 2006/031878 A2 | 3/2006 |
| WO | WO 2006/135434 A2 | 12/2006 |
| WO | WO 2007/001448 A2 | 1/2007 |
| WO | WO 2007/003054 A1 | 1/2007 |
| WO | WO 2007/040840 A2 | 4/2007 |
| WO | WO 2007/062107 A2 | 5/2007 |
| WO | WO 2007/070682 A2 | 6/2007 |
| WO | WO 2007/109810 A2 | 9/2007 |
| WO | WO 2007/118653 A2 | 10/2007 |
| WO | WO 2007/131972 A1 | 11/2007 |
| WO | WO 2007/133807 A2 | 11/2007 |
| WO | WO 2007/137117 A2 | 11/2007 |
| WO | WO 2007/149802 A2 | 12/2007 |
| WO | WO 2007/150030 A2 | 12/2007 |
| WO | WO 2008/019142 A2 | 2/2008 |
| WO | WO 2008/033432 A2 | 3/2008 |
| WO | WO 2008/079924 A1 | 7/2008 |
| WO | WO 2008/093173 A1 | 8/2008 |
| WO | WO 2008/105773 A2 | 9/2008 |
| WO | WO 2008/115319 A2 | 9/2008 |
| WO | WO 2008/115641 A2 | 9/2008 |
| WO | WO 2008/124632 A1 | 10/2008 |
| WO | WO 2008/124634 A1 | 10/2008 |
| WO | WO 2008/124639 A2 | 10/2008 |
| WO | WO 2008/127532 A1 | 10/2008 |
| WO | WO 2008/147456 A2 | 12/2008 |
| WO | WO 2009/027971 A2 | 3/2009 |
| WO | WO 2009/038685 A1 | 3/2009 |
| WO | WO 2009/051837 A2 | 4/2009 |
| WO | WO 2009/076158 A1 | 6/2009 |
| WO | WO 2009/109428 A2 | 9/2009 |
| WO | WO 2009/111588 A1 | 9/2009 |
| WO | WO 2009/158687 A1 | 12/2009 |
| WO | WO 2010/003009 A2 | 1/2010 |
| WO | WO 2010/017330 A1 | 2/2010 |
| WO | WO 2010/018130 A1 | 2/2010 |
| WO | WO 2010/018131 A1 | 2/2010 |
| WO | WO 2010/018132 A1 | 2/2010 |
| WO | WO 2010/018133 A1 | 2/2010 |
| WO | WO 2010/037566 A1 | 4/2010 |
| WO | WO 2010/042870 A1 | 4/2010 |
| WO | WO 2010/054215 A1 | 5/2010 |
| WO | WO 2010/115046 A2 | 10/2010 |
| WO | WO 2010/123569 A2 | 10/2010 |
| WO | WO 2010/128303 A1 | 11/2010 |
| WO | WO 2010/138192 A2 | 12/2010 |
| WO | WO 2010/138194 A2 | 12/2010 |
| WO | WO 2010/146606 A1 | 12/2010 |
| WO | WO 2011/150240 A1 | 12/2011 |

OTHER PUBLICATIONS

[No Author Listed] S-28463. Drugs Future. 1999;24(6):622-7.

Abad et al., Comparison of a Monoclonal Antibody-Based Enzyme-Linked Immunosorbent Assay and Gas Chromatography for the Determination of Nicotine in Cigarette Smoke Condensates. Anal Chem. 1993;65:3227-31.

(56) References Cited

OTHER PUBLICATIONS

Aliferis et al., Living polypeptides. Biomacromolecules. Sep.-Oct. 2004;5(5):1653-6.

Allison, The mode of action of immunological adjuvants. Dev Biol Stand. 1998;92:3-11.

Amsberry et al., Amine prodrugs which utilize hydroxy amide lactonization. I. A potential redox-sensitive amide prodrug. Pharm Res. Mar. 1991;8(3):323-30.

Anderson et al., Immunization to nicotine with a peptide-based vaccine composed of a conformationally biased agonist of C5a as a molecular adjuvant. Int Immunopharmacol. Jan. 2003;3(1):137-46.

Bachmann et al., Chapter 19. Virus-like Particles: Combining Innate and Adaptive Immunity for Effective Vaccination. Novel Vaccination Strategies. 2004:415-32.

Badiee et al., Coencapsulation of CpG oligodeoxynucleotides with recombinant Leishmania major stress-inducible protein 1 in liposome enhances immune response and protection against leishmaniasis in immunized BALB/c mice. Clin Vaccine Immunol. Apr. 2008;15(4):668-74. Epub Jan. 30, 2008.

Bauer et al., Human TLR9 confers responsiveness to bacterial DNA via species-specific CpG motif recognition. Proc Natl Acad Sci U S A. Jul. 31, 2001;98(16):9237-42. Epub Jul. 24, 2001.

Bjercke et al., Comparison of monoclonal and polyclonal antibodies to continine in nonisotopic and isotopic immunoassays. J Immunol Meth. 1987;96:239-46.

Black et al., Advances in the design and delivery of peptide subunit vaccines with a focus on toll-like receptor agonists. Expert Rev Vaccines. Feb. 2010;9(2):157-73.

Borchardt et al., Stereopopulation control. 3. Facilitation of intramolecular conjugate addition of the carboxyl group. J Am Chem Soc. Dec. 27, 1972;94(26):9175-82.

Bourquin et al., Targeting CpG oligonucleotides to the lymph node by nanoparticles elicits efficient antitumoral immunity. J Immunol. Sep. 1, 2008;181(5):2990-8.

Buter et al., Synthesis of Macrocyclic sulfides using cesium thiolates: 1,4,8,11-tetrathiacyclotetradecane. Organic Synthesis. 1993;8:592. 5 pages.

Carpino et al., Reductive Lactonization of strategically methylated quinone propionic acid esters and amides. J Org Chem. 1989;54:3303-10.

Carrot et al., Two general methods for the synthesis of Thiol-Functional Polycaprolactones. Macromolecules. 1999;32:5264-9.

Castro et al., Nicotine Antibodies: Comparison of Ligand Specificities of Antibodies Produced against Two Nicotine Conjugates. Eur Biochem. 1980;104:331-40.

Castro et al., Nicotine Antibody Production: Comparison of two nicotine conjugates in different animal species. Biochem Biophys Res Comm. 1975;67(2):583-9.

Castro et al., Nicotine enzyme immunoassay. Res Commun Chem Pathol Pharmacol. Mar. 1986;51(3):393-404.

Cerny et al., Anti-nicotine abuse vaccines in the pipeline: an update. Expert Opin Investig Drugs. May 2008;17(5):691-6.

Cerritelli et al., PEG-SS-PPS: reduction-sensitive disulfide block copolymer vesicles for intracellular drug delivery. Biomacromolecules. Jun. 2007;8(6):1966-72. Epub May 12, 2007.

Chan et al., Preparation and characterization of immunogens for antibody production against metanephrine and normetanephrine. J Immunol Methods. Aug. 1, 2002;266(1-2):143-54.

Chan et al.,Synthesis and immunological characterization of toll-like receptor 7 agonistic conjugates. Bioconjug Chem. Jun. 2009;20(6):1194-200.

Chinen et al., Basic and clinical immunology. J Allergy Clin Immunol. Aug. 2005;116(2):411-8.

Chu et al., CpG oligodeoxynucleotides act as adjuvants that switch on T helper 1 (Th1) immunity. J Exp Med. Nov. 17, 1997;186(10):1623-31.

Connor et al., Ex vivo evaluation of anti-EpCAM immunocytokine huKS-IL2 in ovarian cancer. J Immunother. 2004;27(3):211-19.

Cornuz et al., A vaccine against nicotine for smoking cessation: a randomized controlled trial. PLoS One. Jun. 25, 2008;3(6):e2547.

Cruz et al., The influence of PEG chain length and targeting moiety on antibody-mediated delivery of nanoparticle vaccines to human dendritic cells. Biomaterials. Oct. 2011;32(28):6791-803. Epub Jul. 2, 2011. E-pub version.

Czarniecki, Small molecule modulators of toll-like receptors. J Med Chem. Nov. 13, 2008;51(21):6621-6. doi: 10.1021/jm800957k. Epub Oct. 2, 2008.

Davis et al., CpG DNA is a potent enhancer of specific immunity in mice immunized with recombinant hepatitis B surface antigen. J Immunol. Jan. 15, 1998;160(2):870-6.

De Gregorio et al., Alum adjuvanticity: unraveling a century old mystery. Eur J Immunol. Aug. 2008;38(8):2068-71.

Delemarre et al., Repopulation of macrophages in popliteal lymph nodes of mice after liposome-mediated depletion. J Leukoc Biol. 1990;47(3):251-7.

Diwan et al., Dose sparing of CpG oligodeoxynucleotide vaccine adjuvants by nanoparticle delivery. Curr Drug Deliv. Oct. 2004;1(4):405-12.

Diwan et al., Enhancement of immune responses by co-delivery of a CpG oligodeoxynucleotide and tetanus toxoid in biodegradable nanospheres. J Control Release. Dec. 13, 2002;85(1-3):247-62.

Dockrell et al., Imiquimod and resiquimod as novel immunomodulators. J Antimicrob Chemother. Dec. 2001;48(6):751-5.

Feuillet et al., Involvement of Toll-like receptor 5 in the recognition of flagellated bacteria. Proc Natl Acad Sci U S A. Aug. 15, 2006;103(33):12487-92. Epub Aug. 4, 2006.

Fife et al., Highly Efficient intramolecular nucleophilic reactions. The cyclization of p-nitrophenyl N-(2-mercaptophenyl)-N-methylcarbamate and phenyl N-(2-Aminophenyl)-N-methylcarbamate. JACS. 1975;97:5878-82.

Fukuyama et al., 2,4 Dinitrobenzenesulfonamides: A Simple and Practical Method for the Preparation of a Variety of Secondary Amines and Diamines. Tetrahedron Letters. 1997;38(33):5831-4.

Gant et al., Semiquinone anion radicals formed by the reaction of quinones with glutathione or amino acids. FEBS Lett. Jun. 9, 1986;201(2):296-300.

Gao et al., In vivo molecular and cellular imaging with quantum dots. Curr Op Biotechnol. 2005;16:63-72.

Garçon et al., Boosting vaccine power. Sci Am. Oct. 2009;301(4):72-9.

Gomes et al., Cyclization-activated prodrugs. Molecules. Nov. 12, 2007;12(11):2484-506.

Gratton et al., The effect of particle design on cellular internalization pathways. Proc Natl Acad Sci U S A. Aug. 19, 2008;105(33):11613-8. Epub Aug. 12, 2008.

Greenwald et al., Drug delivery systems based on trimethyl lock lactonization: poly(ethylene glycol) prodrugs of amino-containing compounds. J Med Chem. Feb. 10, 2000;43(3):475-87.

Haas et al., Sequence independent interferon-alpha induction by multimerized phosphodiester DNA depends on spatial regulation of Toll-like receptor-9 activation in plasmacytoid dendritic cells. Immunology. Feb. 2009;126(2):290-8. Epub Nov. 15, 2008.

Haddadi, Delivery of rapamycin by PLGA nanoparticles enhances its suppressive activity on dendritic cells. J Biomed Mat Res A. 2007;84A(4):885-98.

Hammerbeck et al., Administration of a dual toll-like receptor 7 and toll-like receptor 8 agonist protects against influenza in rats. Antiviral Res. Jan. 2007;73(1):1-11. Epub Aug. 18, 2006.

Hatsukami et al., Safety and immunogenicity of a nicotine conjugate vaccine in current smokers. Clin Pharmacol Ther. Nov. 2005;78(5):456-67.

Hattermann et al., The Toll-like receptor 7/8-ligand resiquimod (R-848) primes human neutrophils for leukotriene B4, prostaglandin E2 and platelet-activating factor biosynthesis. FASEB J. May 2007;21(7):1575-85. Epub Jan. 30, 2007.

Heeg et al., Structural requirements for uptake and recognition of CpG oligonucleotides. Int J Med Microbiol. Jan. 2008;298(1-2):33-8. Epub Aug. 13, 2007.

Heil et al., Species-specific recognition of single-stranded RNA via toll-like receptor 7 and 8. Science. Mar. 5, 2004;303(5663):1526-9. Epub Feb. 19, 2004.

(56) References Cited

OTHER PUBLICATIONS

Hemmi et al., A Toll-like receptor recognizes bacterial DNA. Nature. Dec. 7, 2000;408(6813):740-5.
Hermanson, Bioconjugate Techniques 2nd Edition. Academic Press. 2008. 1233 pages.
Hieda et al., Active Immunization Alters the Plasma Nicotine Concentration in Rats. J Pharmacol Exp Therapeutics. 1997;283:1076-81.
Hieda et al., Immunization of rats reduces nicotine distribution to brain. Psychopharmacology. 1999;143:150-7.
Hieda et al., Vaccination against nicotine during continued nicotine administration in rats: immunogenicity of the vaccine and effects on nicotine distribution to brain. Int J Immunopharmacol. Oct. 2000;22(10):809-19.
Hruby et al., Poly (ethylene oxide)-coated polymide nanoparticles deradable by glutathione. Colloid Polym Sci. 2007;285:569-74.
Hutchins et al., Facile intramolecular nucleophilic attack by alkoxide ions on ethyl and p-nitrophenyl carbamates. J Am Chem Soc. May 30, 1973;95(11):3786-90.
Hutchins et al., Fast Intramolecular Nucleophilic attack by phenoxide ion on carbamate ester groups. JACS. 1973;95:2282-6.
Iwasaki et al., Cell-specific delivery of polymeric nanoparticles to carbohydrate-tagging cells. Biomacromolecules. Oct. 2007;8(10):3162-8. Epub Sep. 21, 2007.
Jennings et al., Immunodrugs: therapeutic VLP-based vaccines for chronic diseases. Annu Rev Pharmacol Toxicol. 2009;49:303-26.
Jurk et al., Human TLR7 or TLR8 independently confer responsiveness to the antiviral compound R-848. Nat Immunol. Jun. 2002;3(6):499.
Kamber et al., Organocatalytic ring-opening polymerization. Chem Rev. Dec. 2007;107(12):5813-40. Epub Nov. 8, 2007.
Keyler et al., Enhanced immunogenicity of a bivalent nicotine vaccine. Int Immunopharmacol. Nov. 2008;8(11):1589-94. Epub Jul. 24, 2008.
Kimura et al., Binding of oligoguanylate to scavenger receptors is required for oligonucleotides to augment NK cell activity and induce IFN. J Biochem. Nov. 1994;116(5):991-4.
King et al., Stereopopulation Control. 7. Rate Enhancement in the Lactonization of 3-(o-Hydroxyphenyl) propionic Acids: Dependence on the Size of Aromatic Ring Substituents. J Am Chem Soc. 1983;105:2752-60.
Klein, Probing the interactions of proteins and nanoparticles. Proc Natl Acad Sci U S A. Feb. 13, 2007;104(7):2029-30. Epub Feb. 6, 2007.
Krieg et al., CpG motifs in bacterial DNA trigger direct B-cell activation. Nature. 1995;374(6522):546-9.
Kwon et al., Pseudopoly(amino acids): A study of the synthesis and characterization of poly(acyl-hydroxyproline-esters). Macromolecules. 1989;22:3250-5.
Langone et al., Nicotine and its metabolites. Radioinununoassays for nicotine and cotinine. Biochem. 1973;12(24):5025-30.
Langone et al., Radioimmunoassay of Nicotine, Cotinine, and y-(3-Pyridyl)- y-oxo-N-methylbutyramide. Met Enzymol. 1982;84:628-40.
Le Pera et al., Highly specific N-monomethylation of primary aromatic amines. Tetrahedron. 2006;62:6100-6.
Lee et al., Polyketal microparticles: a new delivery vehicle for superoxide dismutase. Bioconjug Chem. Jan.-Feb. 2007;18(1):4-7.
Lee et al., Synthesis of 3-(2-aminoethylthio)propyl glycosides. Carbohydr Res. Oct. 1974;37(1):193-201.
Liang et al., Activation of human B cells by phosphorothioate oligodeoxynucleotides. J Clin Invest. Sep. 1, 1996;98(5):1119-29.
Lindblad, Aluminium compounds for use in vaccines. Immunol Cell Biol. Oct. 2004;82(5):497-505.
Lipford et al., Bacterial DNA as immune cell activator. Trends Microbiol. Dec. 1998;6(12):496-500.
Lipford et al., CpG-containing synthetic oligonucleotides promote B and cytotoxic T cell responses to protein antigen: a new class of vaccine adjuvants. Eur J Immunol. Sep. 1997;27(9):2340-4.

Lloyd, Disulphide reduction in lysosomes. The role of cysteine. Biochem J. Jul. 1, 1986;237(1):271-2.
Lönnberg, Solid-phase synthesis of oligonucleotide conjugates useful for delivery and targeting of potential nucleic acid therapeutics. Bioconjug Chem. Jun. 2009;20(6):1065-94.
Malin et al., Passive immunization against nicotine prevents nicotine alleviation of nicotine abstinence syndrome. Pharmacol Biochem Behav. Jan. 2001;68(1):87-92.
Malyala et al., Enhancing the therapeutic efficacy of CpG oligonucleotides using biodegradable microparticles. Adv Drug Deliv Rev. Mar. 28, 2009;61(3):218-25. Epub Jan. 11, 2009.
Malyala et al., The potency of the adjuvant, CpG oligos, is enhanced by encapsulation in PLG microparticles. J Pharm Sci. Mar. 2008;97(3):1155-64.
Manolova et al., Nanoparticles target distinct dendritic cell populations according to their size. Eur J Immunol. 2008;38:1404-13.
Maurer et al., A therapeutic vaccine for nicotine dependence: preclinical efficacy, and Phase I safety and immunogenicity. Eur J Immunol. Jul. 2005;35(7):2031-40.
McSorley et al., Bacterial flagellin is an effective adjuvant for CD4+ T cells in vivo. J Immunol. Oct. 1, 2002;169(7):3914-9.
Meldal et al., Cu-catalyzed azide-alkyne cycloaddition. Chem Rev. Aug. 2008;108(8):2952-3015.
Michiels et al., Patent exemption for clinical trials: current status of the Bolar-type provisions in Europe. Life Sciences Intellectual Property Review 2008. Lavoix. www.worldipreview.com. 2008:68-70.
Milstien et al., Rate acceleration by stereopopulation control: models for enzyme action. Proc Natl Acad Sci U S A. Nov. 1970;67(3):1143-7.
Milstien et al., Stereopopulation control. I. Rate enhancement in the lactonizations of 0-hydroxyhydrocinnamic acids. J Am Chem Soc. Dec. 27, 1972;94(26):9158-65.
Nickerson et al., Studies on quinone-thioethers. I. Mechanism of formation and properties of thiodione. Biochemistry. May-Jun. 1963;2:537-43. Biochemistry. May-Jun. 1963;2:537-43.
Paolicelli et al., Surface-modified PLGA-based nanoparticles that can efficiently associate and deliver virus-like particles. Nanomedicine (Lond). Aug. 2010;5(6):843-53.
Papot et al., Design of selectively activated anticancer prodrugs: elimination and cyclization strategies. Curr Med Chem Anticancer Agents. Mar. 2002;2(2):155-85.
Pentel et al., A nicotine conjugate vaccine reduces nicotine distribution to brain and attenuates its behavioral and cardiovascular effects in rats. Pharmacol Biochem Behav. Jan. 1, 2000;65(1):191-8.
Pockros, Current Status of Immunomodulatory Therapies in HCV Infection. Current Hepatitis Reports. 2004;3:16-22.
Richardson, The Synthesis and Chemistry of Certain 2-Substituted 5,6-Dihydroimidazo-, -oxazolo-, and -thiazolo[ij]quinolines. 1963;28:2581-7.
Rissing et al., The Thiol-ene Reaction for the Synthesis of Multifunctional Branched. Organosilanes. Organometallics. 2008;27:5394-7. E-pub Sep. 11, 2008.
Roman et al., Immunostimulatory DNA sequences function as T helper-1-promoting adjuvants. Nat Med. Aug. 1997;3(8):849-54.
Rostovtsev et al., A stepwise huisgen cycloaddition process: copper(I)-catalyzed regioselective "ligation" of azides and terminal alkynes. Angew Chem Int Ed Engl. Jul. 15, 2002;41(14):2596-9.
Saito et al., Drug delivery strategy utilizing conjugation via reversible disulfide linkages: role and site of cellular reducing activities. Adv Drug Deliv Rev. Feb. 10, 2003;55(2):199-215.
Seeman et al., Preparation of hydroxyalkyl-substituted nicotinoids. J Org Chem. 1986;51:1548-61.
Skwarczynski et al., Polyacrylate dendrimer nanoparticles: a self-adjuvanting vaccine delivery system. Angew Chem Int Ed Engl. Aug. 2, 2010;49(33):5742-5.
Sonehara et al., Hexamer palindromic oligonucleotides with 5'-Cg-3' motif(s) induce production of interferon. J Interferon Cytokine Res. Oct. 1996;16(10):799-803.
Strable et al., Chemical modification of viruses and virus-like particles. Curr Top Microbiol Immunol. 2009;327:1-21.

(56) References Cited

OTHER PUBLICATIONS

Thorek et al., Comparative analysis of nanoparticle-antibody conjugations: carbodiimide versus click chemistry. Mol Imaging. Jul.-Aug. 2009;8(4):221-9.

Tomai et al., Resiquimod and other immune response modifiers as vaccine adjuvants. Expert Rev Vaccines. Oct. 2007;6(5):835-47.

Tong et al., Ring-opening polymerization-mediated controlled formulation of polylactide-drug nanoparticles. J Am Chem Soc. Apr. 8, 2009;131(13):4744-54. E-pub Mar. 12, 2009.

Verma et al., Surface-structure-regulated cell-membrane penetration by monolayer-protected nanoparticles. Nat Mater. Jul. 2008;7(7):588-95. Epub May 25, 2008.

Vollmer et al., Characterization of three CpG oligodeoxynucleotide classes with distinct immunostimulatory activities. Eur J Immunol. Jan. 2004;34(1):251-62.

Wang et al., Synthesis of a Novel Esterase-Sensitive Cyclic Prodrug System for Peptides That Utilizes a "Trimethyl Lock"—Facilitated Lactonization Reaction. J Org Chem. 1997;62:1363-7.

Wong SS, Chemistry of Protein Conjugation and Cross-linking, CRC Press Publishers, Boca Raton, 1991.

Wriggers et al. Control of protein functional dynamics by peptide linkers. Biopolymers. 2005;80(6):736-46.

Wu et al., A novel chitosan CpG nanoparticle regulates cellular and humoral immunity of mice.Biomed Environ Sci. Apr. 2006;19(2):87-95.

Wu et al., Resiquimod: a new immune response modifier with potential as a vaccine adjuvant for Th1 immune responses. Antiviral Res. Nov. 2004;64(2):79-83.

Wu et al., Synthesis of glycoconjugate vaccines for Candida albicans using novel linker methodology. J Org Chem. Sep. 2, 2005;70(18):7381-8.

Yu et al., Potent CpG oligonucleotides containing phosphodiester linkages: in vitro and in vivo immunostimulatory properties. Biochem Biophys Res Commun. Sep. 13, 2002;297(1):83-90.

Zhou et al., Preparation of poly(L-serine ester): a structural analog of conventional poly(L-serine). Macromolecules. 1990;23(14):3399-406.

Zwiorek et al., Delivery by cationic gelatin nanoparticles strongly increases the immunostimulatory effects of CpG oligonucleotides. Pharm Res. Mar. 2008;25(3):551-62. Epub Oct. 3, 2007.

Robbins et al., Fabricated Nanoparticles with Cross Validation Using a Humanized Mouse Model. Nanomed Nanotech Biol Med. 2015. Accepted manuscript. doi: 10.1016/j.nano.2014.11.010. 36 pages.

Extended European Search Report dated Apr. 13, 2016 in connection with EP 11838881.8.

Ondachi et al., Synthesis and regioselective substitution of C-6 alkoxy derivatives of (S)-nicotine. Tetrehed Lett. Nov. 13, 2007;49(3):569-72. DOI: 1.1016/J.Tetlet.2007.11.041.

Lazarev et al., Organic Oxides and Peroxides. Harmful substances in industry. Chemistry. 1976;1:474-5.

* cited by examiner

SEQUENCE LISTING

```
<160> NUMBER OF SEQ ID NOS: 1

<210> SEQ ID NO 1
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 1

Ile Leu Met Gln Tyr Ile Lys Ala Asn Ser Lys Phe Ile Gly Ile Pro
1               5                   10                  15

Met Gly Leu Pro Gln Ser Ile Ala Leu Ser Ser Leu Met Val Ala Gln
            20                  25                  30
```

MODIFIED NICOTINIC COMPOUNDS AND RELATED METHODS

RELATED APPLICATIONS

This application claims the benefit under 35 U.S.C. § 119 of U.S. provisional application 61/410,597, filed Nov. 5, 2010, the entire contents of which are incorporated herein by reference.

SEQUENCE LISTING

The contents of the ASCII text file entitled "S168170022US01-SEQ-JAV", created on Jan. 25, 2018 and 1 kb in size, is herein incorporated by reference in its entirety.

BACKGROUND OF THE INVENTION

In the course of making immunogenic constructs to raise an antibody response to nicotinic compounds, such as nicotinic structures and analogs, it would be useful to provide chemical structures to present the nicotinic structures and analogs to cells of the immune system. However, such chemical structures are lacking in the art. Therefore, what are needed are compositions and methods that provide chemical compounds, compositions, and related methods that provide chemical structures to present the nicotinic structures and analogs.

SUMMARY OF THE INVENTION

In one aspect, a compound comprising:

Formula I

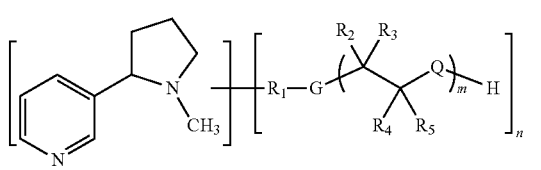

wherein:

$R_1$ is a linker connecting any atom in the nicotine residue to G;

G and Q are independently oxygen, sulfur, —NH—, or —NR—, wherein R comprises alkyl, substituted alkyl, acyl, aryl, or substituted aryl;

R2, R3, R4, and R5, independently, are H or an alkyl group; or R2 and R3, independently, are oxygen and R4 and R5, independently, are H or an alkyl group; or R4 and R5, independently, are oxygen and R2 and R3, independently, are H or an alkyl group;

m is an integer ranging from 1 to 500; with the proviso that if $R_1$ is covalently bound to a methyl residue present at the pyrrolidine nitrogen at position 1' of the nicotine residue, then m is an integer ranging from 50-500; and n is the number of polymeric moieties of

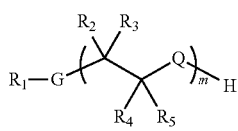

connected to the nicotine residue is provided.

In one embodiment, $R_1$ is either absent or comprises substituted or unsubstituted C1-C18 alkene or alkane, substituted or unsubstituted C1-C18 alkoxy, substituted or unsubstituted alkylamino, substituted or unsubstituted alkylthio, substituted or unsubstituted aryl, substituted or unsubstituted alkylaryl, substituted or unsubstituted heterocycle or substituted or unsubstituted alkylheterocycle.

In another embodiment, $R_2$ comprises H, substituted or unsubstituted C1-C18 alkene or alkane, substituted or unsubstituted C1-C18 alkoxy, substituted or unsubstituted alkylamino, substituted or unsubstituted alkylthio, substituted or unsubstituted aryl, substituted or unsubstituted alkylaryl, substituted or unsubstituted heterocycle, substituted or unsubstituted alkylheterocyclic.

In yet another embodiment, $R_3$ comprises H, substituted or unsubstituted C1-C18 alkene or alkane, substituted or unsubstituted C1-C18 alkoxy, substituted or unsubstituted alkylamino, substituted or unsubstituted alkylthio, substituted or unsubstituted aryl, substituted or unsubstituted alkylaryl, substituted or unsubstituted heterocycle, substituted or unsubstituted alkylheterocyclic.

In still another embodiment, $R_4$ comprises H, substituted or unsubstituted C1-C18 alkene or alkane, substituted or unsubstituted C1-C18 alkoxy, substituted or unsubstituted alkylamino, substituted or unsubstituted alkylthio, substituted or unsubstituted aryl, substituted or unsubstituted alkylaryl, substituted or unsubstituted heterocycle, substituted or unsubstituted alkylheterocyclic.

In a further embodiment, $R_5$ comprises H, substituted or unsubstituted C1-C18 alkene or alkane, substituted or unsubstituted C1-C18 alkoxy, substituted or unsubstituted alkylamino, substituted or unsubstituted alkylthio, substituted or unsubstituted aryl, substituted or unsubstituted alkylaryl, substituted or unsubstituted heterocycle, substituted or unsubstituted alkylheterocyclic.

In one embodiment, G comprises oxygen. In another embodiment, G comprises sulfur. In yet another embodiment, G comprises nitrogen.

In one embodiment, Q comprises oxygen. In another embodiment, Q comprises sulfur. In still another embodiment, Q comprises nitrogen.

In a further embodiment, m ranges from 20 to 500. In another embodiment, m ranges from 50 to 500. In still another embodiment, m ranges from 100 to 500. In yet another embodiment, m ranges from 200 to 500.

In one embodiment, n is an integer ranging from 1 to 12. In another embodiment, n ranges from 1 to 5. In yet another embodiment, n ranges from 1 to 2. In still another embodiment, n equals 1.

In a further embodiment, $R_1$ comprises $C_1$-$C_6$, G and Q comprise oxygen; $R_2$, $R_3$, $R_4$, and $R_5$ comprise hydrogen, m ranges from 45 to 180, and n equals 1.

In another embodiment, the nicotine residue comprises optically pure (+)-(2'R, 3'R) or (−)-(2'S, 3'S)-hydroxylmethyl nicotine derivatives.

In another aspect, a compound comprising:

Formula II

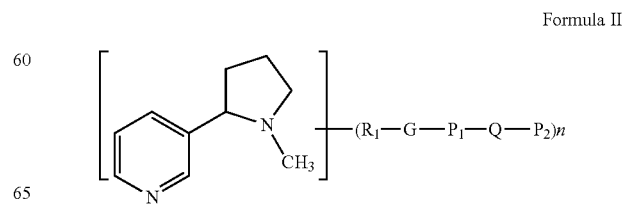

wherein:

P$_1$ is a polymer comprising monomeric residues of unsubstituted or substituted ethylene oxide, ethylene sulfide and/or ethyleneimine, and copolymers thereof, with the proviso that if R$_1$ is covalently bound to a methyl residue present at the pyrrolidine nitrogen at position 1' of the nicotine residue, then P$_1$ is not a polymer comprising 1-40 monomeric residues of unsubstituted ethylene oxide;

G and Q are independently oxygen, sulfur, —NH—, or —NR—, wherein R comprises alkyl, substituted alkyl, acyl, aryl, or substituted aryl;

R$_1$ is a linker connecting any atom in the nicotine residue to polymer P$_1$ through G;

P$_2$ is a second polymer covalently attached to Q; and n is the number of polymeric moieties of —[R$_1$-G-P$_1$-Q-P$_2$] connected to the nicotine residue is provided.

In one embodiment, P$_1$ comprises monomeric residues of unsubstituted or substituted ethylene oxide. In another embodiment, the ethylene oxide is substituted with C$_1$-C$_6$ alkyl or aryl. In yet another embodiment, P$_1$ comprises monomeric residues of unsubstituted or substituted ethylene sulfide. In still another embodiment, the ethylene sulfide is substituted with C$_1$-C$_6$ alkyl or aryl. In a further embodiment, P$_1$ comprises monomeric residues of unsubstituted or substituted ethyleneimine. In one embodiment, the ethyleneimine is substituted with C$_1$-C$_6$ alkyl or aryl. In yet a further embodiment, P$_1$ possesses a number average molecular weight ranging from 2 kilodalton to 10 kilodalton, as determined by nuclear magnetic resonance.

In another embodiment, R$_1$ is either absent or comprises substituted or unsubstituted C1-C18 alkene or alkane, substituted or unsubstituted C1-C18 alkoxy, substituted or unsubstituted alkylamino, substituted or unsubstituted alkylthio, substituted or unsubstituted aryl, substituted or unsubstituted alkylaryl, substituted or unsubstituted heterocycle or substituted or unsubstituted alkylheterocycle.

In still another embodiment, P$_2$ comprises a biodegradable polymer. In yet another embodiment, P$_2$ comprises polyester, polyamide, polycarbonates, polyanhydrides, polyketals or co-polymers thereof. In one embodiment, the polyester comprises polylactide, polyglycolide, polycaprolactone, polylactide-co-glycolide, or co-polymers thereof. In another embodiment, the polyamide comprises polycaprolactam. In a further embodiment, P$_2$ possesses a number average molecular weight ranging from 10 kilodaltons to 100 kilodaltons, as determined by nuclear magnetic resonance.

In one embodiment, G comprises oxygen. In another embodiment, G comprises sulfur. In yet another embodiment, G comprises nitrogen.

In a further embodiment, Q comprises oxygen. In another embodiment, Q comprises sulfur. In yet another embodiment, Q comprises nitrogen.

In one embodiment, n is an integer ranging from 1 to 12. In another embodiment, n ranges from 1 to 5. In still another embodiment, n ranges from 1 to 2. In yet another embodiment, n equals 1.

In a further embodiment, R$_1$ comprises —CH$_2$—, G and Q comprise oxygen, P$_1$ comprises a polymer that comprises monomeric residues of unsubstituted ethylene oxide; P$_2$ comprises polylactide, and n equals 1.

In another embodiment, the nicotine residue comprises optically pure (+)-(2'R, 3'R) or (−)-(2'S, 3'S)— hydroxylmethyl nicotine derivatives.

In yet another aspect, a method comprising: administering any of the compounds provided herein to a subject is provided.

In still another aspect, a vaccine comprising any of the compounds provided herein is provided. In one embodiment, the vaccine further comprises a synthetic nanocarrier. In another embodiment, the vaccine further comprises an additional antigen or an adjuvant. In yet another embodiment, the vaccine further comprises a pharmaceutically acceptable excipient.

In a further aspect, a method comprising administering any of the vaccine provided herein to a subject is provided.

In another aspect, a composition comprising any of the compounds provided herein and a pharmaceutically acceptable excipient is provided.

In yet another aspect, any of the compounds, compositions or vaccines provided may be for use in therapy or prophylaxis.

In still another aspect, any of the compounds, compositions or vaccines provided may be for use in any of the methods provided.

In a further aspect, any of the compounds, compositions or vaccines provided may be for use in a method of prophylaxis or treatment of an addiction or a condition resulting from exposure to a toxin, hazardous substance, environmental toxin or other harmful agent, infection or infectious disease. In one embodiment, said addiction is an addiction to nicotine.

In another aspect, use of any of the compounds provided herein for the manufacture of a medicament, for example a vaccine, for use in any of the methods provided is provided.

DETAILED DESCRIPTION OF THE INVENTION

Before describing the present invention in detail, it is to be understood that this invention is not limited to particularly exemplified materials or process parameters as such may, of course, vary. It is also to be understood that the terminology used herein is for the purpose of describing particular embodiments of the invention only, and is not intended to be limiting of the use of alternative terminology to describe the present invention.

All publications, patents and patent applications cited herein, whether supra or infra, are hereby incorporated by reference in their entirety for all purposes.

As used in this specification and the appended claims, the singular forms "a," "an" and "the" include plural referents unless the content clearly dictates otherwise. For example, reference to "a polymer" includes a mixture of two or more such molecules or a mixture of differing molecular weights of a single polymer species, reference to "a synthetic nanocarrier" includes a mixture of two or more such synthetic nanocarriers or a plurality of such synthetic nanocarriers, reference to a "DNA molecule" includes a mixture of two or more such DNA molecules or a plurality of such DNA molecules, reference to "an adjuvant" includes a mixture of two or more such materials or a plurality of adjuvant molecules, and the like.

As used herein, the term "comprise" or variations thereof such as "comprises" or "comprising" are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein, the term "comprising" is inclusive and does not exclude additional, unrecited integers or method/process steps.

In embodiments of any of the compositions and methods provided herein, "comprising" may be replaced with "consisting essentially of" or "consisting of". The phrase "consisting essentially of" is used herein to require the specified integer(s) or steps as well as those which do not materially affect the character or function of the claimed invention. As used herein, the term "consisting" is used to indicate the presence of the recited integer (e.g. a feature, element, characteristic, property, method/process step or limitation) or group of integers (e.g. features, element, characteristics, properties, method/process steps or limitations) alone.

The invention will be described in more detail below.

A. Introduction

The inventors have unexpectedly and surprisingly discovered that the problems and limitations noted above can be overcome by practicing the invention disclosed herein. In particular, the inventors have unexpectedly discovered that it is possible to provide compounds, and related methods, that comprise:

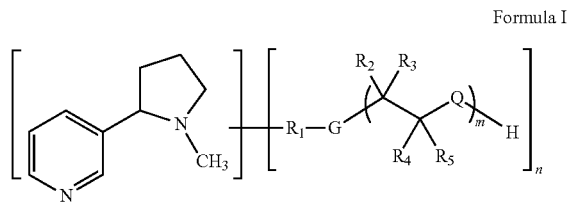

Formula I wherein:

R$_1$ is a linker connecting any atom in the nicotine residue to G;

G and Q are independently oxygen, sulfur, —NH—, or —NR—, wherein R comprises alkyl, substituted alkyl, acyl, aryl, or substituted aryl;

R$_2$, R$_3$, R$_4$, and R$_5$, independently, are H or an alkyl group; or R$_2$ and R$_3$, independently, are oxygen and R$_4$ and R$_5$, independently, are H or an alkyl group; or R$_4$ and R$_5$, independently, are oxygen and R$_2$ and R$_3$, independently, are H or an alkyl group;

m is an integer ranging from 1 to 500; with the proviso that if R$_1$ is covalently bound to a methyl residue present at the pyrrolidine nitrogen at position 1' of the nicotine residue, then m is an integer ranging from 50-500; and n is the number of polymeric moieties of

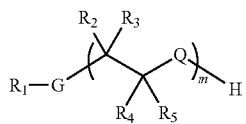

connected to the nicotine residue.

In embodiments, R$_2$, R$_3$, R$_4$, and/or R$_5$, independently, comprise H, substituted or unsubstituted C1-C18 alkene or alkane, substituted or unsubstituted C1-C18 alkoxy, substituted or unsubstituted alkylamino, substituted or unsubstituted alkylthio, substituted or unsubstituted aryl, substituted or unsubstituted alkylaryl, substituted or unsubstituted heterocycle, or substituted or unsubstituted alkylheterocyclic.

Additionally provided are compounds and related methods that comprise:

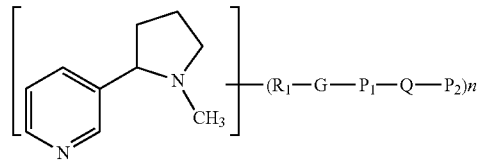

Formula II wherein:

P$_1$ is a polymer comprising monomeric residues of unsubstituted, or C$_1$-C$_6$ alkyl or aryl substituted, ethylene oxide, ethylene sulfide and/or ethyleneimine, and copolymers thereof, with the proviso that if R$_1$ is covalently bound to a methyl residue present at the pyrrolidine nitrogen at position 1' of the nicotine residue, then P$_1$ is not a polymer comprising 1-40 monomeric residues of unsubstituted ethylene oxide;

G and Q are independently oxygen, sulfur, —NH—, or —NR—, wherein R comprises alkyl, substituted alkyl, acyl, aryl, or substituted aryl;

R$_1$ is a linker connecting any atom in the nicotine residue to polymer P$_1$ through G;

P$_2$ is a second polymer covalently attached to Q; and n is the number of polymeric moieties of —[R$_1$-G-P$_1$-Q-P$_2$] connected to the nicotine residue.

Specific embodiments of these compounds, compositions that comprise the compounds, and related methods are disclosed in the Examples.

The invention will now be described in more detail below.

B. Definitions

"Adjuvant" means an agent that does not constitute a specific antigen, but boosts the strength and longevity of immune response to a concomitantly administered antigen. Such adjuvants may include, but are not limited to stimulators of pattern recognition receptors, such as Toll-like receptors, RIG-1 and NOD-like receptors (NLR), mineral salts, such as alum, alum combined with monphosphoryl lipid (MPL) A of Enterobacteria, such as *Escherihia coli, Salmonella minnesota, Salmonella typhimurium*, or *Shigella flexneri* or specifically with MPL® (AS04), MPL A of above-mentioned bacteria separately, saponins, such as QS-21, Quil-A, ISCOMs, ISCOMATRIX™, emulsions such as MF59™ Montanide® ISA 51 and ISA 720, AS02 (QS21+squalene+MPL®), liposomes and liposomal formulations such as AS01, synthesized or specifically prepared microparticles and microcarriers such as bacteria-derived outer membrane vesicles (OMV) of *N. gonorrheae, Chlamydia trachomatis* and others, or chitosan particles, depot-forming agents, such as Pluronic® block co-polymers, specifically modified or prepared peptides, such as muramyl dipeptide, aminoalkyl glucosaminide 4-phosphates, such as RC529, or proteins, such as bacterial toxoids or toxin fragments.

In embodiments, adjuvants comprise agonists for pattern recognition receptors (PRR), including, but not limited to Toll-Like Receptors (TLRs), specifically TLRs 2, 3, 4, 5, 7, 8, 9 and/or combinations thereof. In other embodiments, adjuvants comprise agonists for Toll-Like Receptors 3, agonists for Toll-Like Receptors 7 and 8, or agonists for Toll-Like Receptor 9; preferably the recited adjuvants comprise imidazoquinolines; such as R848; adenine derivatives, such as those disclosed in U.S. Pat. No. 6,329,381 (Sumitomo Pharmaceutical Company), US Published Patent Application 2010/0075995 to Biggadike et al., or WO 2010/018132 to Campos et al.; immunostimulatory DNA; or immunostimulatory RNA. In specific embodiments, synthetic nanocarriers incorporate as adjuvants compounds that are agonists for toll-like receptors (TLRs) 7 & 8 ("TLR 7/8 agonists"). Of utility are the TLR 7/8 agonist compounds disclosed in U.S. Pat. No. 6,696,076 to Tomai et al., including but not limited to imidazoquinoline amines, imidazopyridine amines, 6,7-fused cycloalkylimidazopyridine amines, and 1,2-bridged imidazoquinoline amines. Preferred adjuvants comprise imiquimod and resiquimod (also known as R848). In specific embodiments, an adjuvant may be an agonist for the DC surface molecule CD40. In certain embodiments, to stimulate immunity rather than tolerance, a synthetic nanocarrier incorporates an adjuvant that promotes DC maturation (needed for priming of naive T cells) and the production of cytokines, such as type I interferons, which promote antibody immune responses. In embodiments, adjuvants also may comprise immunostimulatory RNA molecules, such as but not limited to dsRNA, poly I:C or poly I:poly C12U (available as Ampligen®, both poly I:C and poly I:C12U being known as TLR3 stimulants), and/or those disclosed in F. Heil et al., "Species-Specific Recognition of Single-Stranded RNA via Toll-like Receptor 7 and 8" Science 303(5663), 1526-1529 (2004); J. Vollmer et al., "Immune modulation by chemically modified ribonucleosides and oligoribonucleotides" WO 2008033432 A2; A. Forsbach et al., "Immunostimulatory oligoribonucleotides containing specific sequence motif(s) and targeting the Toll-like receptor 8 pathway" WO 2007062107 A2; E. Uhlmann et al., "Modified oligoribonucleotide analogs with enhanced immunostimulatory activity" U.S. Pat. Appl. Publ. US 2006241076; G. Lipford et al., "Immunostimulatory viral RNA oligonucleotides and use for treating cancer and infections" WO 2005097993 A2; G. Lipford et al., "Immunostimulatory G,U-containing oligoribonucleotides, compositions, and screening methods" WO 2003086280 A2. In some embodiments, an adjuvant may be a TLR-4 agonist, such as bacterial lipopolysacccharide (LPS), VSV-G, and/or HMGB-1. In some embodiments, adjuvants may comprise TLR-5 agonists, such as flagellin, or portions or derivatives thereof, including but not limited to those disclosed in U.S. Pat. Nos. 6,130,082, 6,585,980, and 7,192,725. In specific embodiments, synthetic nanocarriers incorporate a ligand for Toll-like receptor (TLR)-9, such as immunostimulatory DNA molecules comprising CpGs, which induce type I interferon secretion, and stimulate T and B cell activation leading to increased antibody production and cytotoxic T cell responses (Krieg et al., CpG motifs in bacterial DNA trigger direct B cell activation. Nature. 1995. 374:546-549; Chu et al. CpG oligodeoxynucleotides act as adjuvants that switch on T helper 1 (Th1) immunity. J. Exp. Med. 1997. 186:1623-1631; Lipford et al. CpG-containing synthetic oligonucleotides promote B and cytotoxic T cell responses to protein antigen: a new class of vaccine adjuvants. Eur. J. Immunol. 1997. 27:2340-2344; Roman et al. Immunostimulatory DNA sequences function as T helper-1-promoting adjuvants. Nat. Med. 1997. 3:849-854; Davis et al. CpG DNA is a potent enhancer of specific immunity in mice immunized with recombinant hepatitis B surface antigen. J. Immunol. 1998. 160:870-876; Lipford et al., Bacterial DNA as immune cell activator. Trends Microbiol. 1998. 6:496-500; U.S. Pat. No. 6,207,646 to Krieg et al.; U.S. Pat. No. 7,223,398 to Tuck et al.; U.S. Pat. No. 7,250,403 to Van Nest et al.; or U.S. Pat. No. 7,566,703 to Krieg et al.

In some embodiments, adjuvants may be proinflammatory stimuli released from necrotic cells (e.g., urate crystals). In some embodiments, adjuvants may be activated components of the complement cascade (e.g., CD21, CD35, etc.). In some embodiments, adjuvants may be activated components of immune complexes. The adjuvants also include complement receptor agonists, such as a molecule that binds to CD21 or CD35. In some embodiments, the complement receptor agonist induces endogenous complement opsonization of the synthetic nanocarrier. In some embodiments, adjuvants are cytokines, which are small proteins or biological factors (in the range of 5 kD-20 kD) that are released by cells and have specific effects on cell-cell interaction, communication and behavior of other cells. In some embodiments, the cytokine receptor agonist is a small molecule, antibody, fusion protein, or aptamer.

In embodiments, at least a portion of the dose of adjuvant may be coupled to synthetic nanocarriers, preferably, all of the dose of adjuvant is coupled to synthetic nanocarriers. In other embodiments, at least a portion of the dose of the adjuvant is not coupled to the synthetic nanocarriers. In embodiments, the dose of adjuvant comprises two or more types of adjuvants. For instance, and without limitation, adjuvants that act on different TLR receptors may be combined. As an example, in an embodiment a TLR 7/8 agonist may be combined with a TLR 9 agonist. In another embodiment, a TLR 7/8 agonist may be combined with a TLR 4 agonist. In yet another embodiment, a TLR 9 agonist may be combined with a TLR 3 agonist.

"Administering" or "administration" means providing a drug to a subject in a manner that is pharmacologically useful.

"Antigen" means a B cell antigen or T cell antigen. In embodiments, antigens are coupled to the synthetic nanocarriers. In other embodiments, antigens are not coupled to the synthetic nanocarriers. In embodiments antigens are coadministered with the synthetic nanocarriers. In other embodiments antigens are not coadministered with the synthetic nanocarriers. "Type(s) of antigens" means molecules that share the same, or substantially the same, antigenic characteristics.

"B cell antigen" means any antigen that is or recognized by and triggers an immune response in a B cell (e.g., an antigen that is specifically recognized by a B cell receptor on a B cell). In some embodiments, an antigen that is a T cell antigen is also a B cell antigen. In other embodiments, the T cell antigen is not also a B cell antigen. B cell antigens include, but are not limited to, proteins, peptides, small molecules, and carbohydrates. In some embodiments, the B cell antigen comprises a non-protein antigen (i.e., not a protein or peptide antigen). In some embodiments, the B cell antigen comprises a carbohydrate associated with an infectious agent. In some embodiments, the B cell antigen comprises a glycoprotein or glycopeptide associated with an infectious agent. The infectious agent can be a bacterium, virus, fungus, protozoan, or parasite. In some embodiments, the B cell antigen comprises a poorly immunogenic antigen. In some embodiments, the B cell antigen comprises an abused substance or a portion thereof. In some embodiments, the B cell antigen comprises an addictive substance or a portion thereof. Addictive substances include, but are not limited to, nicotine, a narcotic, a cough suppressant, a tranquilizer, and a sedative. In some embodiments, the B cell antigen comprises a toxin, such as a toxin from a chemical weapon or natural sources. The B cell antigen may also comprise a hazardous environmental agent. In some embodiments, the B cell antigen comprises a self antigen. In other embodiments, the B cell antigen comprises an alloantigen, an allergen, a contact sensitizer, a degenerative disease antigen, a hapten, an infectious disease antigen, a cancer antigen, an atopic disease antigen, an autoimmune disease antigen, an addictive substance, a xenoantigen, or a metabolic disease enzyme or enzymatic product thereof.

"Couple" or "Coupled" or "Couples" (and the like) means to chemically associate one entity (for example a moiety) with another. In some embodiments, the coupling is covalent, meaning that the coupling occurs in the context of the presence of a covalent bond between the two entities. In non-covalent embodiments, the non-covalent coupling is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. In embodiments, encapsulation is a form of coupling.

"Dosage form" means a pharmacologically and/or immunologically active material in a medium, carrier, vehicle, or device suitable for administration to a subject.

"Encapsulate" means to enclose at least a portion of a substance within a synthetic nanocarrier. In some embodiments, a substance is enclosed completely within a synthetic nanocarrier. In other embodiments, most or all of a substance that is encapsulated is not exposed to the local environment external to the synthetic nanocarrier. In other embodiments, no more than 50%, 40%, 30%, 20%, 10% or 5% is exposed to the local environment. Encapsulation is distinct from absorption, which places most or all of a substance on a surface of a synthetic nanocarrier, and leaves the substance exposed to the local environment external to the synthetic nanocarrier.

"Linker" means a moiety that connects two chemical components together through either single covalent bonds or multiple covalent bonds.

"Maximum dimension of a synthetic nanocarrier" means the largest dimension of a nanocarrier measured along any axis of the synthetic nanocarrier. "Minimum dimension of a synthetic nanocarrier" means the smallest dimension of a synthetic nanocarrier measured along any axis of the synthetic nanocarrier. For example, for a spheriodal synthetic nanocarrier, the maximum and minimum dimension of a synthetic nanocarrier would be substantially identical, and would be the size of its diameter. Similarly, for a cuboidal synthetic nanocarrier, the minimum dimension of a synthetic nanocarrier would be the smallest of its height, width or length, while the maximum dimension of a synthetic nanocarrier would be the largest of its height, width or length. In an embodiment, a minimum dimension of at least 75%, preferably at least 80%, more preferably at least 90%, of the synthetic nanocarriers in a sample, based on the total number of synthetic nanocarriers in the sample, is greater than 100 nm. In an embodiment, a maximum dimension of at least 75%, preferably at least 80%, more preferably at least 90%, of the synthetic nanocarriers in a sample, based on the total number of synthetic nanocarriers in the sample, is equal to or less than 5 μm. Preferably, a minimum dimension of at least 75%, preferably at least 80%, more preferably at least 90%, of the synthetic nanocarriers in a sample, based on the total number of synthetic nanocarriers in the sample, is greater than 110 nm, more preferably greater than 120 nm, more preferably greater than 130 nm, and more preferably still greater than 150 nm. Aspects ratios of the maximum and minimum dimensions of inventive synthetic nanocarriers may vary depending on the embodiment. For instance, aspect ratios of the maximum to minimum dimensions of the synthetic nanocarriers may vary from 1:1 to 1,000,000:1, preferably from 1:1 to 100,000:1, more preferably from 1:1 to 1000:1, still more preferably from 1:1 to 100:1, and yet more preferably from 1:1 to 10:1. Preferably, a maximum dimension of at least 75%, preferably at least 80%, more preferably at least 90%, of the synthetic nanocarriers in a sample, based on the total number of synthetic nanocarriers in the sample is equal to or less than 3 μm, more preferably equal to or less than 2 μm, more preferably equal to or less than 1 μm, more preferably equal to or less than 800 nm, more preferably equal to or less than 600 nm, and more preferably still equal to or less than 500 nm. In preferred embodiments, a maximum dimension of at least 75%, preferably at least 80%, more preferably at least 90%, of the synthetic nanocarriers in a sample, based on the total number of synthetic nanocarriers in the sample, is equal to or greater than 100 nm, more preferably equal to or greater than 120 nm, more preferably equal to or greater than 130 nm, more preferably equal to or greater than 140 nm, and more preferably still equal to or greater than 150 nm. Measurement of synthetic nanocarrier sizes is obtained by suspending the synthetic nanocarriers in a liquid (usually aqueous) media and using dynamic light scattering (DLS) (e.g. using a Brookhaven ZetaPALS instrument). For example, a suspension of synthetic nanocarriers can be diluted from an aqueous buffer into purified water to achieve a final synthetic nanocarrier suspension concentration of approximately 0.01 to 0.1 mg/mL. The diluted suspension may be prepared directly inside, or transferred to, a suitable cuvette for DLS analysis. The cuvette may then be placed in the DLS, allowed to equilibrate to the controlled temperature, and then scanned for sufficient time to aquire a stable and reproducible distribution based on appropriate inputs for viscosity of the medium and refractive indicies of the sample. The effective diameter, or mean of the distribution, is then reported.

"Pharmaceutically acceptable excipient" means a pharmacologically inactive material used together with the recited synthetic nanocarriers to formulate the inventive compositions. Pharmaceutically acceptable excipients comprise a variety of materials known in the art, including but not limited to saccharides (such as glucose, lactose, and the like), preservatives such as antimicrobial agents, reconstitution aids, colorants, saline (such as phosphate buffered saline), and buffers.

"Release" or "Release Rate" means the rate that an entrapped substance transfers from a synthetic nanocarrier into local environment, such as a surrounding release media. First, the synthetic nanocarrier is prepared for the release testing by placing into the appropriate release media. This is generally done by exchanging a buffer after centrifugation to pellet the synthetic nanocarrier and reconstitution of the synthetic nanocarriers under a mild condition. The assay is started by placing the sample at 37° C. in an appropriate temperature-controlled apparatus. A sample is removed at various time points.

The synthetic nanocarriers are separated from the release media by centrifugation to pellet the synthetic nanocarriers. The release media is assayed for the substance that has been released from the synthetic nanocarriers. The substance is measured using HPLC to determine the content and quality of the substance. The pellet containing the remaining entrapped substance is dissolved in solvents or hydrolyzed by base to free the entrapped substance from the synthetic nanocarriers. The pellet-contained substance is then also measured by HPLC after dissolution or destruction of the pellet to determine the content and quality of the substance that has not been released at a given time point.

The mass balance is closed between substance that has been released into the release media and what remains in the synthetic nanocarriers. Data are presented as the fraction released or as the net release presented as micrograms released over time.

"Subject" means animals, including warm blooded mammals such as humans and primates; avians; domestic household or farm animals such as cats, dogs, sheep, goats, cattle, horses and pigs; laboratory animals such as mice, rats and guinea pigs; fish; reptiles; zoo and wild animals; and the like.

"Synthetic nanocarrier(s)" means a discrete object that is not found in nature, and that possesses at least one dimension that is less than or equal to 5 microns in size. Albumin nanoparticles are generally included as synthetic nanocarriers, however in certain embodiments the synthetic nanocarriers do not comprise albumin nanoparticles. In embodiments, inventive synthetic nanocarriers do not comprise chitosan.

A synthetic nanocarrier can be, but is not limited to, one or a plurality of lipid-based nanoparticles, polymeric nanoparticles, metallic nanoparticles, surfactant-based emulsions, dendrimers, buckyballs, nanowires, virus-like particles, peptide or protein-based particles (such as albumin nanoparticles) and/or nanoparticles that are developed using a combination of nanomaterials such as lipid-polymer nanoparticles. Synthetic nanocarriers may be a variety of different shapes, including but not limited to spheroidal, cuboidal, pyramidal, oblong, cylindrical, toroidal, and the like. Synthetic nanocarriers according to the invention comprise one or more surfaces. Exemplary synthetic nanocarriers that can be adapted for use in the practice of the present invention comprise: (1) the biodegradable nanoparticles disclosed in U.S. Pat. No. 5,543,158 to Gref et al., (2) the polymeric nanoparticles of Published US Patent Application 20060002852 to Saltzman et al., (3) the lithographically constructed nanoparticles of Published US Patent Application 20090028910 to DeSimone et al., (4) the disclosure of WO 2009/051837 to von Andrian et al., (5) the nanoparticles disclosed in Published US Patent Application 2008/0145441 to Penades et al, (6) the protein nanoparticles disclosed in Published US Patent Application 20090226525 to de los Rios et al., (7) the virus-like particles disclosed in published US Patent Application 20060222652 to Sebbel et al., (8) the nucleic acid coupled virus-like particles disclosed in published US Patent Application 20060251677 to Bachmann et al., (9) the virus-like particles disclosed in WO2010047839A1 or WO2009106999A2, or (10) the nanoprecipitated nanoparticles disclosed in P. Paolicelli et al., "Surface-modified PLGA-based Nanoparticles that can Efficiently Associate and Deliver Virus-like Particles" Nanomedicine. 5(6):843-853 (2010). In embodiments, synthetic nanocarriers may possess an aspect ratio greater than 1:1, 1:1.2, 1:1.5, 1:2, 1:3, 1:5, 1:7, or greater than 1:10.

Synthetic nanocarriers according to the invention that have a minimum dimension of equal to or less than about 100 nm, preferably equal to or less than 100 nm, do not comprise a surface with hydroxyl groups that activate complement or alternatively comprise a surface that consists essentially of moieties that are not hydroxyl groups that activate complement. In a preferred embodiment, synthetic nanocarriers according to the invention that have a minimum dimension of equal to or less than about 100 nm, preferably equal to or less than 100 nm, do not comprise a surface that substantially activates complement or alternatively comprise a surface that consists essentially of moieties that do not substantially activate complement. In a more preferred embodiment, synthetic nanocarriers according to the invention that have a minimum dimension of equal to or less than about 100 nm, preferably equal to or less than 100 nm, do not comprise a surface that activates complement or alternatively comprise a surface that consists essentially of moieties that do not activate complement. In embodiments, synthetic nanocarriers exclude virus-like particles. In embodiments, when synthetic nanocarriers comprise virus-like particles, the virus-like particles comprise non-natural adjuvant (meaning that the VLPs comprise an adjuvant other than naturally occurring RNA generated during the production of the VLPs). In embodiments, synthetic nanocarriers may possess an aspect ratio greater than 1:1, 1:1.2, 1:1.5, 1:2, 1:3, 1:5, 1:7, or greater than 1:10.

"T cell antigen" means any antigen that is recognized by and triggers an immune response in a T cell (e.g., an antigen that is specifically recognized by a T cell receptor on a T cell or an NKT cell via presentation of the antigen or portion thereof bound to a Class I or Class II major histocompatability complex molecule (MHC), or bound to a CD1 complex). In some embodiments, an antigen that is a T cell antigen is also a B cell antigen. In other embodiments, the T cell antigen is not also a B cell antigen. T cell antigens generally are proteins or peptides. T cell antigens may be an antigen that stimulates a CD8+ T cell response, a CD4+ T cell response, or both. The nanocarriers, therefore, in some embodiments can effectively stimulate both types of responses.

In some embodiments the T cell antigen is a T helper cell antigen (i.e. one that can generate an enhanced response to a B cell antigen, preferably an unrelated B cell antigen, through stimulation of T cell help). In embodiments, a T helper cell antigen may comprise one or more peptides obtained or derived from tetanus toxoid, Epstein-Barr virus, influenza virus, respiratory syncytial virus, measles virus, mumps virus, rubella virus, cytomegalovirus, adenovirus, diphtheria toxoid, or a PADRE peptide (known from the work of Sette et al. U.S. Pat. No. 7,202,351). In other embodiments, a T helper cell antigen may comprise one or more lipids, or glycolipids, including but not limited to: α-galactosylceramide (α-GalCer), α-linked glycosphingolipids (from *Sphingomonas* spp.), galactosyl diacylglycerols (from *Borrelia burgdorferi*), lypophosphoglycan (from *Leishmania donovani*), and phosphatidylinositol tetramannoside (PIM4) (from *Mycobacterium leprae*). For additional lipids and/or glycolipids useful as a T helper cell antigen, see V. Cerundolo et al., "Harnessing invariant NKT cells in vaccination strategies." Nature Rev Immun, 9:28-38 (2009). In embodiments, CD4+ T-cell antigens may be derivatives of a CD4+ T-cell antigen that is obtained from a source, such as a natural source. In such embodiments, CD4+ T-cell antigen sequences, such as those peptides that bind to MHC II, may have at least 70%, 80%, 90%, or 95% identity to the antigen obtained from the source. In embodiments, the T cell antigen, preferably a T helper cell antigen, may be coupled to, or uncoupled from, a synthetic nanocarrier.

"Vaccine" means a composition of matter that improves the immune response to a particular pathogen or disease. A vaccine typically contains factors that stimulate a subject's immune system to recognize a specific antigen as foreign and eliminate it from the subject's body. A vaccine also establishes an immunologic 'memory' so the antigen will be quickly recognized and responded to if a person is re-challenged. Vaccines can be prophylactic (for example to prevent future infection by any pathogen), or therapeutic (for example a vaccine against a tumor specific antigen for the treatment of cancer). In embodiments, a vaccine may comprise dosage forms according to the invention.

C. Inventive Compounds and Methods of Making and Using the Compounds

In embodiments, the invention provides for compounds of Formula I:

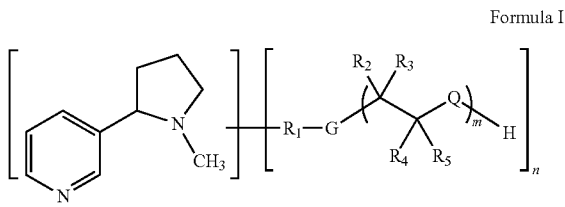

Formula I wherein:

$R_1$ is a linker connecting any atom in the nicotine residue to G;

G and Q are independently oxygen, sulfur, —NH—, or —NR—, wherein R comprises alkyl, substituted alkyl, acyl, aryl, or substituted aryl;

R2, R3, R4, and R5, independently, are H or an alkyl group; or R2 and R3, independently, are oxygen and R4 and R5, independently, are H or an alkyl group; or R4 and R5, independently, are oxygen and R2 and R3, independently, are H or an alkyl group;

m is an integer ranging from 1 to 500; with the proviso that if $R_1$ is covalently bound to a methyl residue present at the pyrrolidine nitrogen at position 1' of the nicotine residue, then m is an integer ranging from 50-500; and n is the number of polymeric moieties of

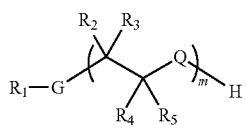

connected to the nicotine residue.

In embodiments, $R_1$ is either absent or comprises substituted or unsubstituted C1-C18 alkene or alkane, substituted or unsubstituted C1-C18 alkoxy, substituted or unsubstituted alkylamino, substituted or unsubstituted alkylthio, substituted or unsubstituted aryl, substituted or unsubstituted alkylaryl, substituted or unsubstituted heterocycle or substituted or unsubstituted alkylheterocycle.

In embodiments, $R_2$, $R_3$, $R_4$, and/or $R_5$, independently, comprise H, substituted or unsubstituted C1-C18 alkene or alkane, substituted or unsubstituted C1-C18 alkoxy, substituted or unsubstituted alkylamino, substituted or unsubstituted alkylthio, substituted or unsubstituted aryl, substituted or unsubstituted alkylaryl, substituted or unsubstituted heterocycle, or substituted or unsubstituted alkylheterocyclic.

In embodiments, m ranges from 20 to 500, preferably m ranges from 50 to 500, more preferably m ranges from 100 to 500, and still more preferably m ranges from 200 to 500. Measurement of the polymeric portion molecular weight, and some effects of varying molecular weight, is generally discussed elsewhere herein. In embodiments, n is an integer ranging from 1 to 12, preferably n ranges from 1 to 5, more preferably n ranges from 1 to 2, and still more preferably n equals 1.

In a preferred embodiment, an inventive compound of Formula I is contemplated, wherein $R_1$ comprises $C_1$-$C_6$, G and Q comprise oxygen; $R_2$, $R_3$, $R_4$, and $R_5$ comprise hydrogen, m ranges from 45 to 180, and n equals 1.

Compounds useful for initiating ring opening polymerization of epoxides, thioepoxides and ethyleneimines or oxazolines include, but are not limited to 1'-hydroxyalkylnicotine such as 1'-hydroxyethylnicotine, 1'-hydroxybutylnicotine, 3'-hydroxyalkylnicotine such as 3'-hydroxymethylnicotine, 4'-hydroxyalkylnicotine such as 4'-hydroxymethylnicotine and 4'-hydroxyethylnicotine, 5'-hydroxyalkylnicotine such as 5'-hydroxypropyl nicotine, 2-hydroxyalkylnicotine such as 2-hydroxymethylnicotine, 4-hydroxyalkylnicotine such as 4-hydroxymethylnicotine, 6-hydroxyalkylnicotine such as 6-hydroxymethylnicotine, 6-hydroxyethylnicotine, and 6-hydroxypropyl nicotine. The syntheses of these compounds are described in this application and in a paper by Seeman, et al, [Journal of Organic Chemistry, 51, 1548, (1986)]. In addition, the amino and mercapto analogs of these compounds can also function as initiators. In embodiments, the nicotine residue may comprise optically pure enantiomers, such as (+)-(2'R, 3'R) or (−)-(2'S, 3'S)-hydroxylmethyl nicotine derivatives. In other embodiments, the nicotine residue may comprise a racemic mixture. The optically pure enantiomers may be separated from one another using chiral separation techniques, for instance using a chiral separation column such as a Chiral Daicel IC® column.

Many epoxides, thioepoxides, ethyleneimines and oxazolines will undergo ring opening polymerization when initiated, under various conditions known to those skilled in the art, by a hydroxyalkylnicotine, a thioalkylnicotine or aminoalkylnicotine. Commonly available epoxides suitable for polymerization in the practice of the present invention, include but are not limited to; ethylene oxide, propylene oxide glycidyl methyl ether, 2,2,3,3-tetramethyloxirane, 3,3,3-Trifluoro-1,2-epoxypropane, styrene oxide, cyclooctene oxide, 1,2-epoxyoctane, tert-Butyl glycidyl ether, 4-Fluorophenyloxirane, Glycidaldehyde diethyl acetal, Phenyl glycidyl ether, Benzyl glycidyl ether, cis, and trans-Stilbene oxide, and many others. Commonly available thiiranes suitable for polymerization in the practice of the present invention, include but are not limited to; ethylene sulfide, propylene sulfide, Cyclohexene sulfide, 1,2-Epithiooctane, 1,2-Epithiododecane, 4-phenoxyphenyl 2-thiiranylmethyl sulfone and many others. Commonly available ethyleneimines and oxazolines suitable for polymerization in the practice of the present invention, include but are not limited to; aziridine, 2-methylaziridine, 1-(benzylsulfonyl)aziridine, 1-(toluene-3-sulfonyl)aziridine, 2-phenylaziridine, 2,3-diphenylaziridine, 1-methylaziridine, 1-phenylaziridine, 2-ethyl-2-oxazoline, 2-methyl2-oxazoline 2-phenyl-2-oxazoline, 4,4-Dimethyl-2-phenyl-2-oxazoline, 3-(4,4-dimethyl-4,5-dihydro-1,3-oxazol-2-yl)pyridine, and many others.

Polymers as covered by Formula I are made by ring opening polymerization of epoxides, thioepoxides, aziridines or 2-alkyl-2-oxazolines. The actual conditions used depend on the particular polymer of Formula I to be synthesized. For example, epoxide and thioepoxide polymerizations are typically initiated with an anionic compound. For compounds of Formula I, a nicotine compound with an alcohol containing substituent can be converted to the alkoxide by reaction with a strong base. This nicotine alkoxide may then used to initiate ring opening polymerization of an amount of epoxide or thioepoxide chosen to provide the nicotine substituted polyether or polythioether of a particular molecular weight. Polyacylethylenimines may be formed by ring opening polymerization of 2-alkyl-2-oxazolines using a cationic initiator or alkylating agent. For compounds of Formula I, a nicotine compound with an alcohol containing substituent may be converted to a halide or sulfonate ester. This alkylating agent may then be used to initiate ring opening polymerization of an amount of 2-alkyl-2-oxazoline chosen to provide the nicotine substituted polyacylethylenimines of a particular molecular weight.

In embodiments, a compound of Formula II is provided:

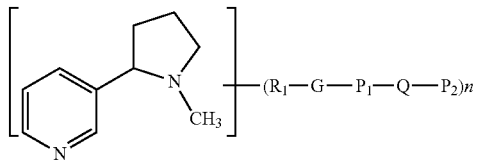

Formula II wherein:

$P_1$ is a polymer comprising monomeric residues of unsubstituted, or $C_1$-$C_6$ alkyl or aryl substituted, ethylene oxide, ethylene sulfide and/or ethyleneimine, and copolymers thereof, with the proviso that if $R_1$ is covalently bound to a methyl residue present at the pyrrolidine nitrogen at position 1' of the nicotine residue, then $P_1$ is not a polymer comprising 1-40 monomeric residues of unsubstituted ethylene oxide;

G and Q are independently oxygen, sulfur, —NH—, or —NR—, wherein R comprises alkyl, substituted alkyl, acyl, aryl, or substituted aryl;

$R_1$ is a linker connecting any atom in the nicotine residue to polymer $P_1$ through G;

$P_2$ is a second polymer covalently attached to Q; and n is the number of polymeric moieties of —[$R_1$-G-$P_1$-Q-$P_2$] connected to the nicotine residue.

In embodiments, $R_1$ is either absent or comprises substituted or unsubstituted C1-C18 alkene or alkane, substituted or unsubstituted C1-C18 alkoxy, substituted or unsubstituted alkylamino, substituted or unsubstituted alkylthio, substituted or unsubstituted aryl, substituted or unsubstituted alkylaryl, substituted or unsubstituted heterocycle or substituted or unsubstituted alkylheterocycle.

In embodiments, $P_2$ comprises a biodegradable polymer. In embodiments, the biodegradable polymer comprises polyester, polyamide, polycarbonates, polyanhydrides, polyketals or co-polymers thereof. In embodiments, the polyester comprises polylactide, polyglycolide, polycaprolactone, polylactide-co-glycolide, or co-polymers thereof; the polyamide comprises polycaprolactam.

In embodiments, the molecular weight of the polymeric portions of compounds of Formula I or Formula II may be varied. In embodiments, the molecular weights of $P_1$ and $P_2$ may be adjusted to maximize the ability of the inventive compounds to self-assemble during a typical emulsion process and to form nanoparticles. In embodiments, $P_1$ possesses a number average molecular weight ranging from 2 kilodaltons to 10 kilodaltons, preferably $P_1$ possesses a number average molecular weight ranging from 3 kilodaltons to 6 kilodaltons, as determined by nuclear magnetic resonance. In embodiments, $P_2$ possesses a number average molecular weight ranging from 10 kilodaltons to 100 kilodaltons, $P_2$ possesses a number average molecular weight ranging from 15 kilodaltons to 30 kilodaltons, preferably as determined by nuclear magnetic resonance. For example, number average molecular weight can be determined by proton NMR wherein the ratio of the polymer repeating units to the end group is established and then multiplied by theoretical repeating unit molecular weight. Alternatively, in the case of a titratable (e.g., acid or base) end group polymer, a known weight concentration may be established and then titrated in the presence of an indicator dye with an appropriate neutralizing agent of known molar concentration to provide moles of end group per mass of polymer. Polymer number average molecular weights can also be determined using conventional NMR techniques, such as those generally explained at sigmaaldrich.com/materials-science/polymer-science/polymer-analysis.html. Any of the molecular weights of the polymers provided herein may be a number average molecular weight.

In embodiments, n is an integer ranging from 1 to 12, preferably n ranges from 1 to 5, more preferably n ranges from 1 to 2, and still more preferably n equals 1.

In a preferred embodiment, the invention provides a compound of Formula II, wherein $R_1$ comprises —$CH_2$—, G and Q comprise oxygen, $P_1$ comprises a polymer that comprises monomeric residues of unsubstituted ethylene oxide; $P_2$ comprises polylactide, and n equals 1.

With respect to Formula II, compounds useful for initiating ring opening polymerization of epoxides, thioepoxides and ethyleneimines or oxazolines include, but are not limited to 1'-hydroxyalkylnicotine such as 1'-hydroxyethylnicotine, 1'-hydroxybutylnicotine, 3'-hydroxyalkylnicotine such as 3'-hydroxymethylnicotine, 4'-hydroxyalkylnicotine such as 4'-hydroxymethylnicotine and 4'-hydroxyethylnicotine, 5'-hydroxyalkylnicotine such as 5'-hydroxypropyl nicotine, 2-hydroxyalkylnicotine such as 2-hydroxymethylnicotine, 4-hydroxyalkylnicotine such as 4-hydroxymethylnicotine, 6-hydroxyalkylnicotine such as 6-hydroxymethylnicotine, 6-hydroxyethylnicotine, and 6-hydroxypropyl nicotine. The syntheses of these compounds are described in this application and in a paper by Seeman, et al, [Journal of Organic Chemistry, 51, 1548, (1986)]. In addition the amino and mercapto analogs of these compounds can also function as initiators. Many epoxides, thioepoxides, ethyleneimines and oxazolines will undergo ring opening polymerization when initiated, under various conditions known to those skilled in the art, by a hydroxyalkylnicotine, a thioalkylnicotine or aminoalkylnicotine. Commonly available epoxides, include but are not limited to; ethylene oxide, propylene oxide glycidyl methyl ether, 2,2,3,3-tetramethyloxirane, 3,3,3-Trifluoro-1,2-epoxypropane, styrene oxide, cyclooctene oxide, 1,2-epoxyoctane, tert-Butyl glycidyl ether, 4-Fluorophenyloxirane, Glycidaldehyde diethyl acetal, Phenyl glycidyl ether, Benzyl glycidyl ether, cis, and trans-Stilbene oxide, and many others. Commonly available thioepoxides, include but are not limited to; ethylene sulfide, propylene sulfide, Cyclohexene sulfide, 1,2-Epithiooctane, 1,2-Epithiododecane, 4-phenoxyphenyl 2-thiiranylmethyl sulfone and many others. Commonly available ethyleneimines, and oxazolines, include but are not limited to; aziridine, 2-methylaziridine, 1-(benzylsulfonyl)aziridine, 1-(toluene-3-sulfonyl)aziridine, 2-phenylaziridine, 2,3-diphenylaziridine, 1-methylaziridine, 1-phenylaziridine, 2-ethyl-2-oxazoline, 2-methyl2-oxazoline 2-phenyl-2-oxazoline, 4,4-Dimethyl-2-phenyl-2-oxazoline, 3-(4,4-dimethyl-4,5-dihydro-1,3-oxazol-2-yl)pyridine, and many others. The polymers comprising these monomers all are examples of nicotine-$P_1$ conjugates of Formula I.

The nicotine-$P_1$ conjugates of Formula I can then be used to initiate polymerization of a second monomer to provide the compound of Formula II. Of interest are compounds of Formula II formed by ring opening polymerization of cyclic esters, lactones, anhydrides, carbonates, lactams, and N-carboxyanhydrides. Of particular interest are compounds of Formula II formed by ring opening polymerization of lactide, and caprolactone. The ring opening polymerization of these can be initiated by compounds of Formula I, often at elevated temperatures, under the influence of a catalyst such as tin (II) ethylhexanoate or an amine catalyst such as TBD (1,5,7-triazabicyclo[4,4,0]dec-5-ene), DBU (1,8-diazabicyclo[5,4,0]undec-7-ene), DMAP (dimethylaminopyridine) as well as other catalysts known to those skilled in the art.

Compounds useful for initiating ring opening polymerization of epoxides, thioepoxides and ethyleneimines or oxazolines include, but are not limited to 1'-hydroxyalkylnicotine such as 1'-hydroxyethylnicotine, 1'-hydroxybutylnicotine, 3'-hydroxyalkylnicotine such as 3'-hydroxymethylnicotine, 4'-hydroxyalkylnicotine such as 4'-hydroxymethylnicotine and 4'-hydroxyethylnicotine, 5'-hydroxyalkylnicotine such as 5'-hydroxypropyl nicotine, 2-hydroxyalkylnicotine such as 2-hydroxymethylnicotine, 4-hydroxyalkylnicotine such as 4-hydroxymethylnicotine, 6-hydroxyalkylnicotine such as 6-hydroxymethylnicotine, 6-hydroxyethylnicotine, and 6-hydroxypropyl nicotine. The syntheses of these compounds are described in this application and in a paper by Seeman, et al, [Journal of Organic Chemistry, 51, 1548, (1986)]. In addition the amino and mercapto analogs of these compounds can also function as initiators. Many epoxides, thioepoxides, ethyleneimines and oxazolines will undergo ring opening polymerization when initiated, under various conditions known to those skilled in the art, by a hydroxyalkylnicotine, a thioalkylnicotine or aminoalkylnicotine. Commonly available epoxides, include but are not limited to; ethylene oxide, propylene oxide glycidyl methyl ether, 2,2,3,3-tetramethyloxirane, 3,3,3-Trifluoro-1,2-epoxypropane, styrene oxide, cyclooctene oxide, 1,2-epoxyoctane, tert-Butyl glycidyl ether, 4-Fluorophenyloxirane, Glycidaldehyde diethyl acetal, Phenyl glycidyl ether, Benzyl glycidyl ether, cis, and trans-Stilbene oxide, and many others. Commonly available thioepoxides, include but are not limited to; ethylene sulfide, propylene sulfide, Cyclohexene sulfide, 1,2-Epithiooctane, 1,2-Epithiododecane, 4-phenoxyphenyl 2-thiiranylmethyl sulfone and many others. Commonly available ethyleneimines, and oxazolines, include but are not limited to; aziridine, 2-methylaziridine, 1-(benzylsulfonyl)aziridine, 1-(toluene-3-sulfonyl) aziridine, 2-phenylaziridine, 2,3-diphenylaziridine, 1-methylaziridine, 1-phenylaziridine, 2-ethyl-2-oxazoline, 2-methyl2-oxazoline 2-phenyl-2-oxazoline, 4,4-Dimethyl-2-phenyl-2-oxazoline, 3-(4,4-dimethyl-4,5-dihydro-1,3-oxazol-2-yl)pyridine, and many others. The polymers comprising these monomers all are examples of nicotine-$P_1$ conjugates of Formula I.

The nicotine-$P_1$ conjugates of Formula I can then be used to initiate polymerization of a second monomer to provide the compound of Formula II. Of interest are compounds of Formula II formed by ring opening polymerization of cyclic esters, lactones, anhydrides, carbonates, lactams, and N-carboxyanhydrides. Of particular interest are compounds of Formula II formed by ring opening polymerization of lactide, and caprolactone. The ring opening polymerization of these can be initiated by compounds of Formula I, often at elevated temperatures, under the influence of a catalyst such as tin (II) ethylhexanoate or an amine catalyst such as TBD (1,5,7-triazabicyclo[4,4,0]dec-5-ene), DBU (1,8-diazabicyclo[5,4,0]undec-7-ene), DMAP (dimethylaminopyridine) as well as other catalysts known to those skilled in the art.

Compounds of Formula II may be produced by the ring opening polymerization of cyclic esters, carbonates or anhydrides wherein the polymerization is initiated by a polymer of Formula I. Typical catalysts for this process include metals such as tin(II) ethylhexanoate and organic bases such as 1,5,7-triazabicyclo[4,4,0]dec-5-ene (TBD), 1,8-diazabicyclo[5,4,0]undec-7-ene (DBU), or 4-dimethylaminopyridine (DMAP). The polymerization can be carried out without solvent at elevated temperature (100-200° C.), or in an inert solvent such as toluene at reflux temperature.

D. Inventive Compositions

The compounds of the present invention are particularly useful in the making of vaccines that generate an antibody response to the nicotine residue in subjects that are administered the inventive compounds. In embodiments, the recited compositions and/or vaccines may comprise one or more adjuvants, and one or more additional antigens, in addition to the inventive compounds. Formulation of vaccines that comprise the inventive compounds may be performed using conventional techniques. The inventive compounds may also be incorporated into synthetic nanocarriers. For example, the compounds may be adsorbed onto the surface of synthetic nanocarriers, preferably leaving the nicotine residue exposed where it could serve as a B cell antigen. Alternatively, the compounds may be covalently bound to a surface of synthetic nanocarriers, again preferably leaving the nicotine residue exposed where it could serve as a B cell antigen.

Preferably, inventive compositions, and even more preferably inventive vaccines, may comprise synthetic nanocarriers that comprise the inventive compounds. A wide variety of synthetic nanocarriers can be used according to the invention. In some embodiments, synthetic nanocarriers are spheres or spheroids. In some embodiments, synthetic nanocarriers are flat or plate-shaped. In some embodiments, synthetic nanocarriers are cubes or cubic. In some embodiments, synthetic nanocarriers are ovals or ellipses. In some embodiments, synthetic nanocarriers are cylinders, cones, or pyramids. In some embodiments, it is desirable to use a population of synthetic nanocarriers that is relatively uniform in terms of size, shape, and/or composition so that each synthetic nanocarrier has similar properties. For example, at least 80%, at least 90%, or at least 95% of the synthetic nanocarriers, based on the total number of synthetic nanocarriers, may have a minimum dimension or maximum dimension that falls within 5%, 10%, or 20% of the average diameter or average dimension of the synthetic nanocarriers. In some embodiments, a population of synthetic nanocarriers may be heterogeneous with respect to size, shape, and/or composition.

Synthetic nanocarriers can be solid or hollow and can comprise one or more layers. In some embodiments, each layer has a unique composition and unique properties relative to the other layer(s). To give but one example, synthetic nanocarriers may have a core/shell structure, wherein the core is one layer (e.g. a polymeric core) and the shell is a second layer (e.g. a lipid bilayer or monolayer). Synthetic nanocarriers may comprise a plurality of different layers.

In some embodiments, synthetic nanocarriers may optionally comprise one or more lipids. In some embodiments, a synthetic nanocarrier may comprise a liposome. In some embodiments, a synthetic nanocarrier may comprise a lipid bilayer. In some embodiments, a synthetic nanocarrier may comprise a lipid monolayer. In some embodiments, a synthetic nanocarrier may comprise a micelle. In some embodiments, a synthetic nanocarrier may comprise a core comprising a polymeric matrix surrounded by a lipid layer (e.g., lipid bilayer, lipid monolayer, etc.). In some embodiments, a synthetic nanocarrier may comprise a non-polymeric core (e.g., metal particle, quantum dot, ceramic particle, bone particle, viral particle, proteins, nucleic acids, carbohydrates, etc.) surrounded by a lipid layer (e.g., lipid bilayer, lipid monolayer, etc.).

In some embodiments, synthetic nanocarriers can comprise one or more polymers. In some embodiments, such a polymer can be surrounded by a coating layer (e.g., liposome, lipid monolayer, micelle, etc.). In some embodiments, various elements of the synthetic nanocarriers can be coupled with the polymer.

In some embodiments, an immunofeature surface, targeting moiety, and/or oligonucleotide can be covalently associated with a polymeric matrix. In some embodiments, covalent association is mediated by a linker. In some embodiments, an immunofeature surface, targeting moiety, and/or oligonucleotide can be noncovalently associated with a polymeric matrix. For example, in some embodiments, an immunofeature surface, targeting moiety, and/or oligonucleotide can be encapsulated within, surrounded by, and/or dispersed throughout a polymeric matrix. Alternatively or additionally, an immunofeature surface, targeting moiety, and/or nucleotide can be associated with a polymeric matrix by hydrophobic interactions, charge interactions, van der Waals forces, etc.

A wide variety of polymers and methods for forming polymeric matrices therefrom are known conventionally. In general, a polymeric matrix comprises one or more polymers. Polymers may be natural or unnatural (synthetic) polymers. Polymers may be homopolymers or copolymers comprising two or more monomers. In terms of sequence, copolymers may be random, block, or comprise a combination of random and block sequences. Typically, polymers in accordance with the present invention are organic polymers.

Examples of polymers suitable for use in the present invention—either as mixtures with the compounds of Formula I and/or II or useful as $P_2$ in Formula II, include, but are not limited to, polyethylenes, polycarbonates (e.g. poly(1,3-dioxan-2one)), polyanhydrides (e.g. poly(sebacic anhydride)), polypropylfumerates, polyamides (e.g. polycaprolactam), polyacetals, polyethers, polyesters (e.g., polylactide, polyglycolide, polylactide-co-glycolide, polycaprolactone, polyhydroxyacid (e.g. poly(β-hydroxyalkanoate))), poly(orthoesters), polycyanoacrylates, polyvinyl alcohols, polyurethanes, polyphosphazenes, polyacrylates, polymethacrylates, polyureas, polystyrenes, and polyamines, polylysine, polylysine-PEG copolymers, and poly(ethyleneimine), poly(ethylene imine)-PEG copolymers.

In some embodiments, polymers in accordance with the present invention include polymers which have been approved for use in humans by the U.S. Food and Drug Administration (FDA) under 21 C.F.R. § 177.2600, including but not limited to polyesters (e.g., polylactic acid, poly(lactic-co-glycolic acid), polycaprolactone, polyvalerolactone, poly(1,3-dioxan-2one)); polyanhydrides (e.g., poly(sebacic anhydride)); polyethers (e.g., polyethylene glycol); polyurethanes; polymethacrylates; polyacrylates; and polycyanoacrylates.

In some embodiments, polymers can be hydrophilic. For example, polymers may comprise anionic groups (e.g., phosphate group, sulphate group, carboxylate group); cationic groups (e.g., quaternary amine group); or polar groups (e.g., hydroxyl group, thiol group, amine group). In some embodiments, a synthetic nanocarrier comprising a hydrophilic polymeric matrix generates a hydrophilic environment within the synthetic nanocarrier. In some embodiments, polymers can be hydrophobic. In some embodiments, a synthetic nanocarrier comprising a hydrophobic polymeric matrix generates a hydrophobic environment within the synthetic nanocarrier. Selection of the hydrophilicity or hydrophobicity of the polymer may have an impact on the nature of materials that are incorporated (e.g. coupled) within the synthetic nanocarrier.

In some embodiments, polymers may be modified with one or more moieties and/or functional groups. A variety of moieties or functional groups can be used in accordance with the present invention. In some embodiments, polymers may be modified with polyethylene glycol (PEG), with a carbohydrate, and/or with acyclic polyacetals derived from polysaccharides (Papisov, 2001, ACS Symposium Series, 786:301). Certain embodiments may be made using the general teachings of U.S. Pat. No. 5,543,158 to Gref et al., or WO publication WO2009/051837 by Von Andrian et al. The inventive compounds may be used in the making of such embodiments, particularly if a B cell response against nicotine or nicotine-like compounds is desired.

In some embodiments, polymers may be modified with a lipid or fatty acid group. In some embodiments, a fatty acid group may be one or more of butyric, caproic, caprylic, capric, lauric, myristic, palmitic, stearic, arachidic, behenic, or lignoceric acid. In some embodiments, a fatty acid group may be one or more of palmitoleic, oleic, vaccenic, linoleic, alpha-linoleic, gamma-linoleic, arachidonic, gadoleic, arachidonic, eicosapentaenoic, docosahexaenoic, or erucic acid.

In some embodiments, polymers may be polyesters, including copolymers comprising lactic acid and glycolic acid units, such as poly(lactic acid-co-glycolic acid) and poly(lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEG copolymers and copolymers of lactide and glycolide (e.g., PLA-PEG copolymers, PGA-PEG copolymers, PLGA-PEG copolymers, and derivatives thereof. In some embodiments, polyesters include, for example, poly(caprolactone), poly(caprolactone)-PEG copolymers, poly(L-lactide-co-L-lysine), poly(serine ester), poly(4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA are characterized by the ratio of lactic acid:glycolic acid. Lactic acid can be L-lactic acid, D-lactic acid, or D,L-lactic acid. The degradation rate of PLGA can be adjusted by altering the lactic acid:glycolic acid ratio. In some embodiments, PLGA to be used in accordance with the present invention is characterized by a lactic acid:glycolic acid ratio of approximately 85:15, approximately 75:25, approximately 60:40, approximately 50:50, approximately 40:60, approximately 25:75, or approximately 15:85.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid anhydride), methyl methacrylate, polymethacrylate, poly(methyl methacrylate) copolymer, polyacrylamide, aminoalkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g. DNA, or derivatives thereof). Amine-containing polymers such as poly(lysine) (Zauner et al., 1998, Adv. Drug Del. Rev., 30:97; and Kabanov et al., 1995, Bioconjugate Chem., 6:7), poly(ethylene imine) (PEI; Boussif et al., 1995, Proc. Natl. Acad. Sci., USA, 1995, 92:7297), and poly (amidoamine) dendrimers (Kukowska-Latallo et al., 1996, Proc. Natl. Acad. Sci., USA, 93:4897; Tang et al., 1996, Bioconjugate Chem., 7:703; and Haensler et al., 1993, Bioconjugate Chem., 4:372) are positively-charged at physiological pH, form ion pairs with nucleic acids, and mediate transfection in a variety of cell lines. In embodiments, the inventive synthetic nanocarriers may not comprise (or may exclude) cationic polymers.

In some embodiments, polymers can be degradable polyesters bearing cationic side chains (Putnam et al., 1999, Macromolecules, 32:3658; Barrera et al., 1993, J. Am. Chem. Soc., 115:11010; Kwon et al., 1989, Macromolecules, 22:3250; Lim et al., 1999, J. Am. Chem. Soc., 121:5633; and Zhou et al., 1990, Macromolecules, 23:3399). Examples of these polyesters include poly(L-lactide-co-L-lysine) (Barrera et al., 1993, J. Am. Chem. Soc., 115:11010), poly(serine ester) (Zhou et al., 1990, Macromolecules, 23:3399), poly(4-hydroxy-L-proline ester) (Putnam et al., 1999, Macromolecules, 32:3658; and Lim et al., 1999, J. Am. Chem. Soc., 121:5633), and poly(4-hydroxy-L-proline ester) (Putnam et al., 1999, Macromolecules, 32:3658; and Lim et al., 1999, J. Am. Chem. Soc., 121:5633).

The properties of these and other polymers and methods for preparing them are well known in the art (see, for example, U.S. Pat. Nos. 6,123,727; 5,804,178; 5,770,417; 5,736,372; 5,716,404; 6,095,148; 5,837,752; 5,902,599; 5,696,175; 5,514,378; 5,512,600; 5,399,665; 5,019,379; 5,010,167; 4,806,621; 4,638,045; and 4,946,929; Wang et al., 2001, J. Am. Chem. Soc., 123:9480; Lim et al., 2001, J. Am. Chem. Soc., 123:2460; Langer, 2000, Acc. Chem. Res., 33:94; Langer, 1999, J. Control. Release, 62:7; and Uhrich et al., 1999, Chem. Rev., 99:3181). More generally, a variety of methods for synthesizing certain suitable polymers are described in Concise Encyclopedia of Polymer Science and Polymeric Amines and Ammonium Salts, Ed. by Goethals, Pergamon Press, 1980; Principles of Polymerization by Odian, John Wiley & Sons, Fourth Edition, 2004; Contemporary Polymer Chemistry by Allcock et al., Prentice-Hall, 1981; Deming et al., 1997, Nature, 390:386; and in U.S. Pat. Nos. 6,506,577, 6,632,922, 6,686,446, and 6,818,732.

In some embodiments, polymers can be linear or branched polymers. In some embodiments, polymers can be dendrimers. In some embodiments, polymers can be substantially cross-linked to one another. In some embodiments, polymers can be substantially free of cross-links. In some embodiments, polymers can be used in accordance with the present invention without undergoing a cross-linking step. It is further to be understood that inventive synthetic nanocarriers may comprise block copolymers, graft copolymers, blends, mixtures, and/or adducts of any of the foregoing and other polymers. Those skilled in the art will recognize that the polymers listed herein represent an exemplary, not comprehensive, list of polymers that can be of use in accordance with the present invention.

In some embodiments, synthetic nanocarriers do not comprise a polymeric component. In some embodiments, synthetic nanocarriers may comprise metal particles, quantum dots, ceramic particles, etc. In some embodiments, a non-polymeric synthetic nanocarrier is an aggregate of non-polymeric components, such as an aggregate of metal atoms (e.g., gold atoms).

In some embodiments, synthetic nanocarriers may optionally comprise one or more amphiphilic entities. In some embodiments, an amphiphilic entity can promote the production of synthetic nanocarriers with increased stability, improved uniformity, or increased viscosity. In some embodiments, amphiphilic entities can be associated with the interior surface of a lipid membrane (e.g., lipid bilayer, lipid monolayer, etc.). Many amphiphilic entities known in the art are suitable for use in making synthetic nanocarriers in accordance with the present invention. Such amphiphilic entities include, but are not limited to, phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; a surface active fatty acid, such as palmitic acid or oleic acid; fatty acids; fatty acid monoglycerides; fatty acid diglycerides; fatty acid amides; sorbitan trioleate (Span®85) glycocholate; sorbitan monolaurate (Span®20); polysorbate 20 (Tween®20); polysorbate 60 (Tween®60); polysorbate 65 (Tween®65); polysorbate 80 (Tween®80); polysorbate 85 (Tween®85); polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly(ethylene glycol)5000-phosphatidylethanolamine; poly(ethylene glycol)400-monostearate; phospholipids; synthetic and/or natural detergents having high surfactant properties; deoxycholates; cyclodextrins; chaotropic salts; ion pairing agents; and combinations thereof. An amphiphilic entity component may be a mixture of different amphiphilic entities. Those skilled in the art will recognize that this is an exemplary, not comprehensive, list of substances with surfactant activity. Any amphiphilic entity may be used in the production of synthetic nanocarriers to be used in accordance with the present invention.

In some embodiments, synthetic nanocarriers may optionally comprise one or more carbohydrates. Carbohydrates may be natural or synthetic. A carbohydrate may be a derivatized natural carbohydrate. In certain embodiments, a carbohydrate comprises monosaccharide or disaccharide, including but not limited to glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid. In certain embodiments, a carbohydrate is a polysaccharide, including but not limited to pullulan, cellulose, microcrystalline cellulose, hydroxypropyl methylcellulose (HPMC), hydroxycellulose (HC), methylcellulose (MC), dextran, cyclodextran, glycogen, hydroxyethylstarch, carageenan, glycon, amylose, chitosan, N,O-carboxylmethylchitosan, algin and alginic acid, starch, chitin, inulin, konjac, glucommannan, pustulan, heparin, hyaluronic acid, curdlan, and xanthan. In embodiments, the inventive synthetic nanocarriers do not comprise (or specifically exclude) carbohydrates, such as a polysaccharide. In certain embodiments, the carbohydrate may comprise a carbohydrate derivative such as a sugar alcohol, including but not limited to mannitol, sorbitol, xylitol, erythritol, maltitol, and lactitol.

Compositions according to the invention comprise inventive synthetic nanocarriers in combination with pharmaceutically acceptable excipients, such as preservatives, buffers, saline, or phosphate buffered saline. The compositions may be made using conventional pharmaceutical manufacturing and compounding techniques to arrive at useful dosage forms. In an embodiment, inventive synthetic nanocarriers are suspended in sterile saline solution for injection together with a preservative.

In embodiments, when preparing synthetic nanocarriers as carriers for adjuvants for use in vaccines, methods for coupling the adjuvants to the synthetic nanocarriers may be useful. If the adjuvant is a small molecule it may be of advantage to attach the adjuvant to a polymer prior to the assembly of the synthetic nanocarriers. In embodiments, it may also be an advantage to prepare the synthetic nanocarriers with surface groups that are used to couple the adjuvant to the synthetic nanocarrier through the use of these surface groups rather than attaching the adjuvant to a polymer and then using this polymer conjugate in the construction of synthetic nanocarriers.

For detailed descriptions of available conjugation methods, see Hermanson G T "Bioconjugate Techniques", 2nd Edition Published by Academic Press, Inc., 2008. In addition to covalent attachment the adjuvant can be coupled by absorption to a pre-formed synthetic nanocarrier or it can be coupled by encapsulation during the formation of the synthetic nanocarrier.

D. Methods of Making and Using the Inventive Compositions and Related Methods

Synthetic nanocarriers may be prepared using a wide variety of methods known in the art. For example, synthetic nanocarriers can be formed by methods as nanoprecipitation, flow focusing fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanomaterials have been described (Pellegrino et al., 2005, Small, 1:48; Murray et al., 2000, Ann. Rev. Mat. Sci., 30:545; and Trindade et al., 2001, Chem. Mat., 13:3843). Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755, and also U.S. Pat. Nos. 5,578,325 and 6,007,845; P. Paolicelli et al. "Surface-modified PLGA-based Nanoparticles that can Efficiently Associate and Deliver Virus-like Particles". Nanomedicine. 5(6):843-853 (2010)).

Various materials may be encapsulated into synthetic nanocarriers as desirable using a variety of methods including but not limited to C. Astete et al., "Synthesis and characterization of PLGA nanoparticles" J. Biomater. Sci. Polymer Edn, Vol. 17, No. 3, pp. 247-289 (2006); K. Avgoustakis "Pegylated Poly(Lactide) and Poly(Lactide-Co-Glycolide) Nanoparticles: Preparation, Properties and Possible Applications in Drug Delivery" Current Drug Delivery 1:321-333 (2004); C. Reis et al., "Nanoencapsulation I. Methods for preparation of drug-loaded polymeric nanoparticles" Nanomedicine 2:8-21 (2006); P. Paolicelli et al. "Surface-modified PLGA-based Nanoparticles that can Efficiently Associate and Deliver Virus-like Particles". Nanomedicine. 5(6):843-853 (2010). Other methods suitable for encapsulating materials, such as oligonucleotides, into synthetic nanocarriers may be used, including without limitation methods disclosed in U.S. Pat. No. 6,632,671 to Unger Oct. 14, 2003.

In certain embodiments, synthetic nanocarriers are prepared by a nanoprecipitation process or spray drying. Conditions used in preparing synthetic nanocarriers may be altered to yield particles of a desired size or property (e.g., hydrophobicity, hydrophilicity, external morphology, "stickiness," shape, etc.). The method of preparing the synthetic nanocarriers and the conditions (e.g., solvent, temperature, concentration, air flow rate, etc.) used may depend on the materials to be coupled to the synthetic nanocarriers and/or the composition of the polymer matrix.

If particles prepared by any of the above methods have a size range outside of the desired range, particles can be sized, for example, using a sieve.

Elements of the inventive synthetic nanocarriers (such as moieties of which an immunofeature surface is comprised, targeting moieties, polymeric matrices, antigens and the like) may be coupled to the overall synthetic nanocarrier, e.g., by one or more covalent bonds, or may be coupled by means of one or more linkers. Additional methods of functionalizing synthetic nanocarriers may be adapted from Published US Patent Application 2006/0002852 to Saltzman et al., Published US Patent Application 2009/0028910 to DeSimone et al., or Published International Patent Application WO/2008/127532 A1 to Murthy et al.

Alternatively or additionally, synthetic nanocarriers can be coupled to immunofeature surfaces, targeting moieties, adjuvants, various antigens, and/or other elements directly or indirectly via non-covalent interactions. In non-covalent embodiments, the non-covalent coupling is mediated by non-covalent interactions including but not limited to charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. Such couplings may be arranged to be on an external surface or an internal surface of an inventive synthetic nanocarrier. In embodiments, encapsulation and/or absorption are/is a form of coupling.

In embodiments, the inventive synthetic nanocarriers can be combined with other adjuvants by admixing in the same vehicle or delivery system. Such adjuvants may include, but are not limited to mineral salts, such as alum, alum combined with monphosphoryl lipid (MPL) A of Enterobacteria, such as *Escherihia coli, Salmonella minnesota, Salmonella typhimurium*, or *Shigella flexneri* or specifically with MPL® (AS04), MPL A of above-mentioned bacteria separately, saponins, such as QS-21, Quil-A, ISCOMs, ISCOMATRIX™, emulsions such as MF59™, Montanide® ISA 51 and ISA 720, AS02 (QS21+squalene+MPL®), liposomes and liposomal formulations such as AS01, synthesized or specifically prepared microparticles and microcarriers such as bacteria-derived outer membrane vesicles (OMV) of *N.*

*gonorrheae, Chlamydia trachomatis* and others, or chitosan particles, depot-forming agents, such as Pluronic® block co-polymers, specifically modified or prepared peptides, such as muramyl dipeptide, aminoalkyl glucosaminide 4-phosphates such as RC529, or proteins, such as bacterial toxoids or toxin fragments. The doses of such other adjuvants can be determined using conventional dose ranging studies.

In embodiments, the inventive synthetic nanocarriers can be combined with an antigen different, similar or identical to those coupled to a nanocarrier (with or without adjuvant, utilizing or not utilizing another delivery vehicle) administered separately at a different time-point and/or at a different body location and/or by a different immunization route or with another antigen and/or adjuvant-carrying synthetic nanocarrier administered separately at a different time-point and/or at a different body location and/or by a different immunization route.

Populations of synthetic nanocarriers may be combined to form pharmaceutical dosage forms according to the present invention using traditional pharmaceutical mixing methods. These include liquid-liquid mixing in which two or more suspensions, each containing one or more subset of nanocarriers, are directly combined or are brought together via one or more vessels containing diluent. As synthetic nanocarriers may also be produced or stored in a powder form, dry powder-powder mixing could be performed as could the re-suspension of two or more powders in a common media. Depending on the properties of the nanocarriers and their interaction potentials, there may be advantages conferred to one or another route of mixing.

Typical inventive compositions that comprise synthetic nanocarriers may comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol).

Compositions according to the invention comprise inventive synthetic nanocarriers in combination with pharmaceutically acceptable excipients. The compositions may be made using conventional pharmaceutical manufacturing and compounding techniques to arrive at useful dosage forms. Techniques suitable for use in practicing the present invention may be found in *Handbook of Industrial Mixing: Science and Practice*, Edited by Edward L. Paul, Victor A. Atiemo-Obeng, and Suzanne M. Kresta, 2004 John Wiley & Sons, Inc.; and *Pharmaceutics: The Science of Dosage Form Design*, 2nd Ed. Edited by M. E. Auten, 2001, Churchill Livingstone. In an embodiment, inventive synthetic nanocarriers are suspended in sterile saline solution for injection together with a preservative.

It is to be understood that the compositions of the invention can be made in any suitable manner, and the invention is in no way limited to compositions that can be produced using the methods described herein. Selection of an appropriate method may require attention to the properties of the particular moieties being associated.

In some embodiments, inventive synthetic nanocarriers are manufactured under sterile conditions or are terminally sterilized. This can ensure that resulting composition are sterile and non-infectious, thus improving safety when compared to non-sterile compositions. This provides a valuable safety measure, especially when subjects receiving synthetic nanocarriers have immune defects, are suffering from infection, and/or are susceptible to infection. In some embodiments, inventive synthetic nanocarriers may be lyophilized and stored in suspension or as lyophilized powder depending on the formulation strategy for extended periods without losing activity.

The inventive compositions may be administered by a variety of routes of administration, including but not limited to parenteral (such as subcutaneous, intramuscular, intravenous, or intradermal), pulmonary, sublingual, oral, intranasal, transnasal, intramucosal, transmucosal, rectal, ophthalmic, transcutaneous, transdermal or by a combination of these routes.

Doses of dosage forms contain varying amounts of populations of synthetic nanocarriers and varying amounts of the compounds of Formulas I or II, according to the invention. The amount of synthetic nanocarriers and/or antigens present in the inventive dosage forms can be varied according to the nature of the antigens, the therapeutic benefit to be accomplished, and other such parameters. In embodiments, dose ranging studies can be conducted to establish optimal therapeutic amount of the population of synthetic nanocarriers and the amount of antigens to be present in the dosage form. In embodiments, the synthetic nanocarriers and the antigens are present in the dosage form in an amount effective to generate an immune response to the antigens upon administration to a subject. It may be possible to determine amounts of the antigens effective to generate an immune response using conventional dose ranging studies and techniques in subjects. Inventive dosage forms may be administered at a variety of frequencies. In a preferred embodiment, at least one administration of the dosage form is sufficient to generate a pharmacologically relevant response. In more preferred embodiment, at least two administrations, at least three administrations, or at least four administrations, of the dosage form are utilized to ensure a pharmacologically relevant response.

The compositions and methods described herein can be used to induce, enhance, suppress, modulate, direct, or redirect an immune response. The compositions and methods described herein can be used in the diagnosis, prophylaxis and/or treatment of conditions such as cancers, infectious diseases, metabolic diseases, degenerative diseases, autoimmune diseases, inflammatory diseases, immunological diseases, or other disorders and/or conditions. The compositions and methods described herein can also be used for the prophylaxis or treatment of an addiction, such as an addiction to nicotine or a narcotic. In preferred embodiments, the compounds of Formulas I or II are used in the prophylaxis or treatment of an addiction to nicotine. The compositions and methods described herein can also be used for the prophylaxis and/or treatment of a condition resulting from the exposure to a toxin, hazardous substance, environmental toxin, or other harmful agent.

EXAMPLES

Example 1

Preparation of Peg-Nicotine Conjugates by Grafting and Reduction: Amine Linkage to Nicotine at 3'-Position. Molecular Weight of about 3.5 KD

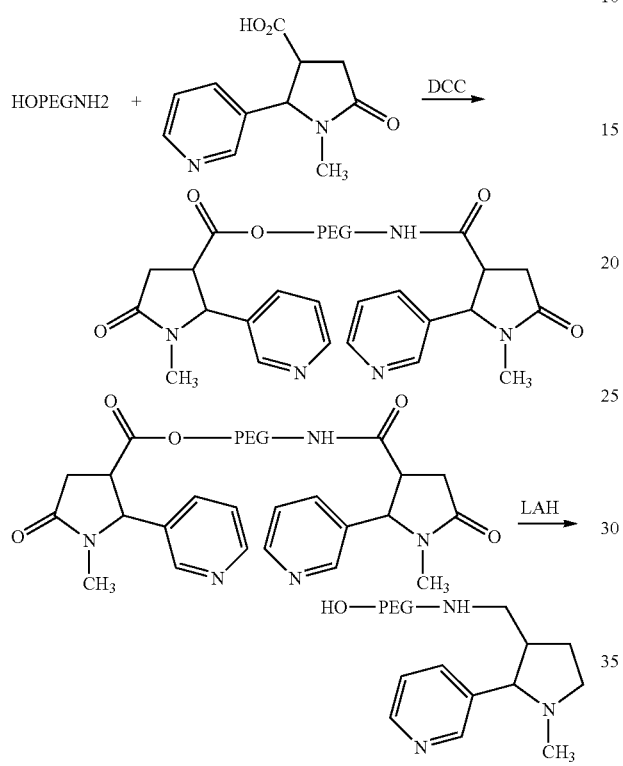

Monoamino poly(ethylene glycol) from JenKem with a molecular weight of 3.5 KD (0.20 gm, $5.7\times10^{-5}$ moles) and an excess of trans-4-cotininecarboxylic acid (0.126 gm, $5.7\times10^{-4}$ moles) were dissolved in dimethylformamide (5.0 mL). The solution was stirred and dicyclohexylcarbodiimide (0.124 gm, $6.0\times10^{-4}$ moles) was added. This solution was stirred overnight at room temperature. Water (0.10 mL) was added and stirring was continued for an additional 15 minutes. The precipitate of dicyclohexyl urea was removed by filtration and the filtrates were evaporated under vacuum. The residue was dissolved in methylene chloride (4.0 mL) and this solution was added to diethyl ether (100 mL). The solution was cooled in the refrigerator for 2 hours and the precipitated polymer was isolated by filtration. After washing with diethyl ether, the solid white polymer was dried under high vacuum. The yield was 0.188 gm. This polymer was used without further purification for the next step.

The cotinine/PEG polymer (0.20 gm, $5.7\times10^{-5}$ moles) was dissolved in dry tetrahydrofuran (10 mL) under nitrogen and the solution was stirred as a solution of lithium aluminum hydride in tetrahydrofuran (1.43 mL of 2.0M, $2.85\times10^{-3}$ moles) was added. The addition of the lithium aluminum hydride caused the polymer to precipitate as a gelatinous mass. The reaction was heated to 80° C. under a slow stream of nitrogen and the tetrahydrofuran was allowed to evaporate. The residue was then heated at 80° C. for 2 hours. After cooling, water (0.5 mL) was cautiously added. Once the hydrogen evolution had stopped, 10% methanol in methylene chloride (50 mL) was added and the reaction mixture was stirred until the polymer had dissolved. This mixture was filtered through Celite and the filtrates were evaporated to dryness under vacuum. The residue was dissolved in methylene chloride (4.0 mL) and this solution was slowly added to diethyl ether (100 mL). The polymer separated as a white flocculent solid and was isolated by centrifugation. After washing with diethyl ether, the solid was dried under vacuum. The yield was 0.129 gm.

Example 2

Preparation of Peg-Nicotine Conjugates by Polymerization with Ethylene Oxide: Amine Linkage to Nicotine at 3'-Position. Molecular Weight of about 2.2 KD

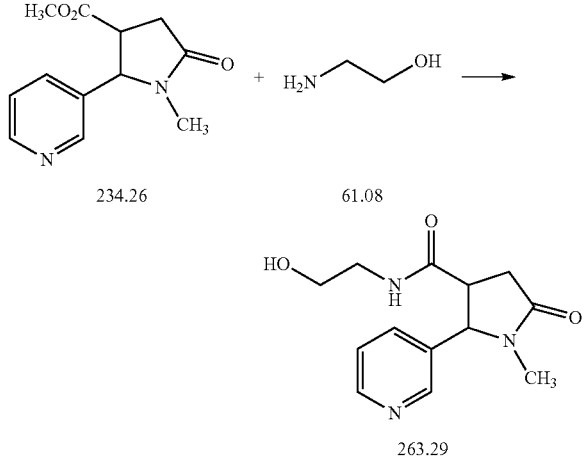

Trans-4-Cotininecarboxylic acid, methyl ester (7.1 gm, $3.03\times10^{-2}$ moles) and ethanolamine (2.22 gm, $3.64\times10^{-2}$ moles) were combined and heated at 150° C. for 45 minutes. The reaction mass was cooled to about 85° C. and boiling tetrahydrofuran (75 mL) was added. The mixture was stirred to provide a solution which was cooled on ice. The amide crystallized as a white solid and was isolated by filtration, washed with THF followed by ether and dried. The yield was 7.2 gm.

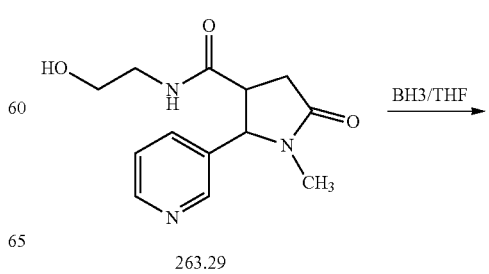

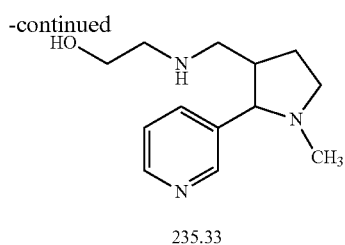

235.33

To a stirred suspension of the cotinine-amide (2.63 gm, 1.0×10$^{-2}$ moles) in THF (20 mL) under argon was added borane in THF (60 mL of 1.0 M solution, 6.0×10$^{-2}$ moles). The reaction was stirred at room temperature for 4 hours and then at 55° C. overnight. After cooling on ice, the reaction was treated with concentrated hydrochloric acid (6.0 mL) followed by methanol (100 mL) containing concentrated hydrochloric acid (6.0 mL). After stirring at room temperature for 4 hours, the reaction was slowly brought to reflux. A portion of the solvents (60 mL) was removed by distillation and the clear solution remaining was cooled and evaporated under vacuum. Additional methanol (100 mL) was added to the residue and the resulting solution was again evaporated under vacuum. The remaining oil was dissolved in water (50 mL) and this solution was treated with solid potassium carbonate which caused the amine to separate. The aqueous mixture was extracted with methylene chloride (2×50 mL) and the pooled extracts were dried over sodium sulfate. After filtration, the methylene chloride was evaporated under vacuum to provide the crude amine as a pale yellow oil in a yield of 2.7 gm. The amine was purified by chromatography on silica gel using 15% of 0.3N methanolic ammonia in methylene chloride (200 mL) followed by 20% of 0.6N methanolic ammonia in methylene chloride. The fractions containing the amine were pooled and evaporated to provide the purified amine as colorless oil in a yield of 1.23 gm.

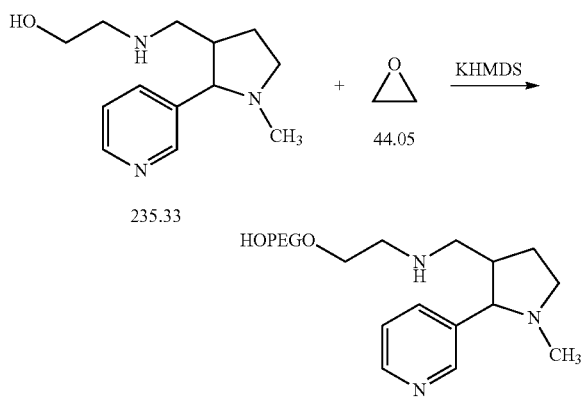

3'-Hydroxyethylaminomethylnicotine (1.10 gm, 4.67×10$^{-3}$ moles) was dissolved in dry dioxane (100 mL) in a pressure flask. A portion of the dioxane (25 mL) was removed by distillation to remove water via azeotropic distillation. This solution was cooled under argon on ice. Potassium hexamethyldisilazide (9.3 mL of 0.5M in toluene, 4.65×10$^{-3}$ moles) was added via syringe and stirring was continued on ice for 15 minutes. To this solution was added ethylene oxide (25 mL, 22 gm, 0.50 moles) which had been condensed in a cooled graduated cylinder. The flask was sealed and the reaction was stirred at room temperature overnight. The reaction was then heated at 50° C. for 30 minutes before being cooled to room temperature. The flask was opened and concentrated hydrochloric acid (2.0 mL) was added. After stirring for 30 minutes the solvents were removed under vacuum.

The viscous liquid residue was stirred with diethyl ether (500 mL) which caused the polymer to separate as a white powder. This was isolated by filtration, washed with ether and dried under vacuum. The polymer was obtained in a yield of 7.2 gm and had a molecular weight of 2200 as determined by NMR.

Example 3

Preparation of Peg-Nicotine Conjugates by Reductive Alkylation: Amine Linkage to Nicotine at 4'-Position. Molecular Weight of about 3.5 KD

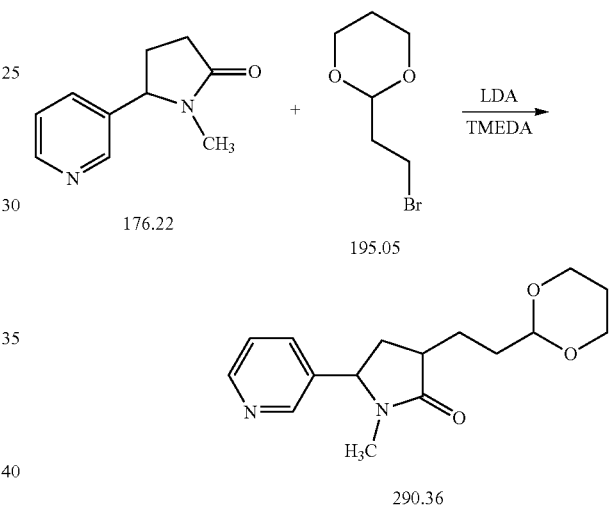

A solution of lithium diisopropylamide (3.23 mL of 2M, 6.46×10$^{-3}$ moles) in dry THF (20 mL) was cooled in a dry ice bath under nitrogen. To this solution was added a solution of cotinine (1.0 gm 5.6×10$^{-3}$ moles) and tetramethylethylenediamine (968 μL) in dry THF (10 mL) over 5 minutes. This solution was stirred at dry ice temperature for 15 minutes and at ice temperature for 10 minutes. The reaction was again cooled in a dry ice bath and 2-bromoethyl dioxane (1.26 gm, 6.46×10$^{-3}$ moles) dissolved in dry THF (10 mL) was added. The reaction was stirred on ice for 30 minutes and then overnight at room temperature. To the reaction was added methanol (20 mL) and after stirring a few minutes, the solvents were removed under vacuum. The residue was partitioned between ethyl acetate (200 mL) and water (200 mL). To the aqueous portion sodium carbonate (20 gm) was added and once dissolved the solution was extracted with methylene chloride (200 mL). The combined ethyl acetate and methylene chloride extracts were dried over magnesium sulfate, filtered and evaporated under vacuum. The oily crude product was dried under high vacuum. The yield was 1.59 gm and was hydrolyzed to the aldehyde without purification.

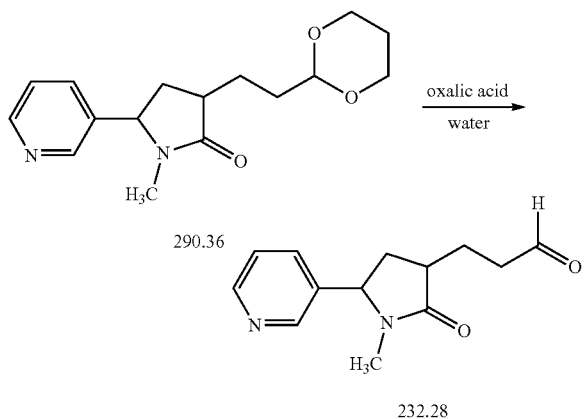

The crude acetal (1.59 gm, 5.48×10$^{-3}$ moles) was added to 0.20 M oxalic acid in water (20 mL) and this solution was heated at reflux for 2 hours. The reaction was cooled to room temperature and solid sodium carbonate was added with stirring to neutralize the oxalic acid. The oil which separated was extracted into methylene chloride (100 mL) and this solution was dried over magnesium sulfate. After filtration, the methylene chloride was removed under vacuum to provide the aldehyde as a pale brown oil in a yield of 0.89 gm. TLC (silica, 10% methanol in methylene chloride) showed that the product was about 85% pure. This was used without purification for the next step.

Monoamino poly(ethylene glycol)hydrochloride from JenKem with a molecular weight of 3.5 KD (350 mg, 1.0×10$^{-5}$ moles) was dissolved in chloroform (10 mL). To this solution was added the cotinine aldehyde (116 mg, 5×10$^{-4}$ moles) followed by acetic acid (60 mg, 1.0×10$^{-3}$ moles) and sodium triacetoxyborohydride (212 mg, 1.0×10$^{-3}$ moles). The reaction was stirred at room temperature overnight. Solid sodium bicarbonate (100 mg) was added and stirring was continued for 2 hours. The reaction mixture was centrifuged to remove a small amount of solids and the supernatant was placed on top of a silica column (1"×10"). The column was developed with 10% methanol in methylene chloride (200 mL) followed by 20% methanol in methylene chloride (500 mL). The fractions containing the polymer were pooled and evaporated. After drying under high vacuum the polymer was obtained as a white solid in a yield of 227 mg.

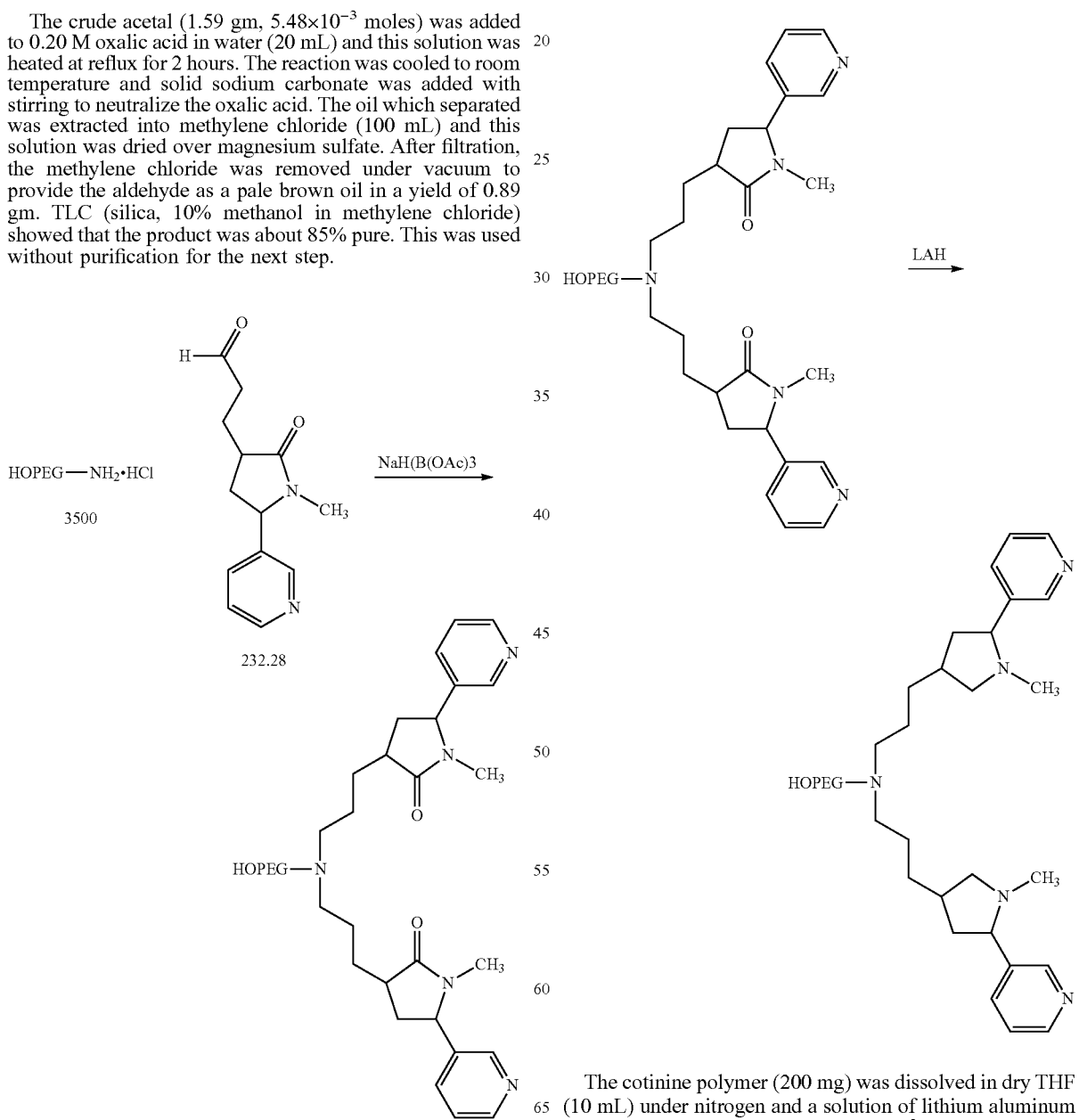

The cotinine polymer (200 mg) was dissolved in dry THF (10 mL) under nitrogen and a solution of lithium aluminum hydride (1.5 mL of 2.0 M in THF, 3×10$^{-3}$ moles) was added via syringe. The reaction was heated at 80° C. for 2 hours.

After cooling, water (0.5 mL) was added followed by 10% methanol in methylene chloride (15 mL). After stirring for 15 minutes the slurry was filtered through a Celite pad which was washed with methylene chloride (10 mL). The combined filtrates were evaporated under vacuum to provide the nicotine polymer in a yield of 200 mg. NMR clearly showed the nicotine in a ratio of 2 nicotines per poly(ethylene) glycol.

Example 4

Preparation of Peg-Nicotine Conjugates by Reaction with Ethylene Oxide:Ether Linkage to Nicotine at 1'-Position. Molecular Weight of about 2.0 KD

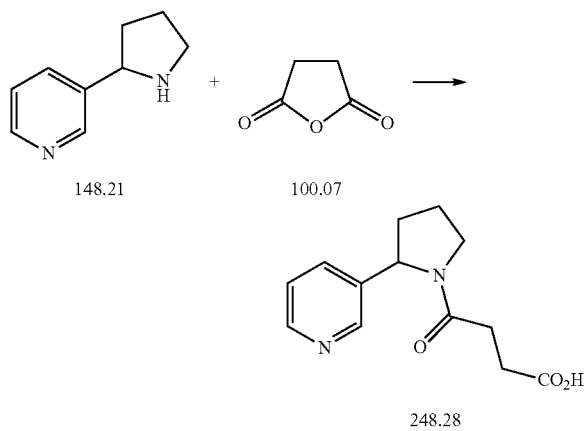

Nornicotine (1.48 gm, 0.01 moles) and succinic anhydride (1.00 gm, 0.01 moles) were combined in chloroform (15 mL). This mixture was brought to reflux causing the succinic anhydride to dissolve. The solution was then stirred at room temperature overnight. The chloroform was removed under vacuum and the residue was dried under high vacuum to give the amide as a tan foam in a yield of 2.4 gm.

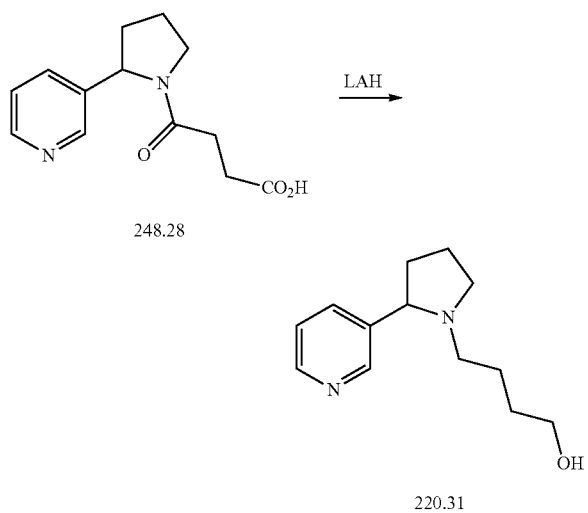

The succinoylated nornicotine (2.4 gm, $9.7 \times 10^{-3}$ moles) was dissolved in dry THF (30 mL) and the solution was stirred on ice under an atmosphere of argon. A solution of lithium aluminum hydride in THF (11.0 mL of a 2.0M solution, $2.2 \times 10^{-2}$ moles) was slowly added. After the addition was complete, the hazy solution was heated at reflux for 2 hours. The pale yellow solution that had formed was stirred at room temperature overnight. After cooling on ice, the reaction was treated with water (0.83 mL) followed by 15% sodium hydroxide (0.83 mL) and then water again (2.5 mL). The resulting slurry was stirred at room temperature for 30 minutes and was then filtered to remove the aluminum salts. The solids were washed with THF (25 mL) and the combined filtrates were evaporated under vacuum. The crude product was purified by chromatography on silica using 15% methanol in methylene chloride as eluent. The fractions containing the product were pooled and evaporated under vacuum to provide the nicotine derivative as a pale yellow oil in a yield of 1.2 gm.

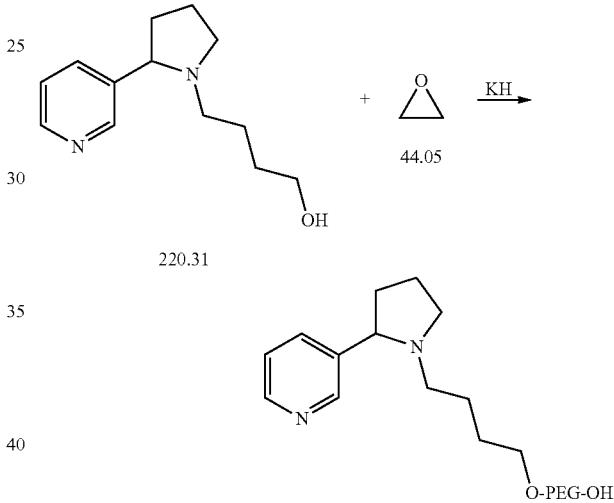

The nicotine alcohol (1.30 gm, $5.9 \times 10^{-3}$ moles) was dissolved in dry THF (120 mL) under a blanket of argon in a pressure bottle. Potassium hydride suspension in mineral oil (780 mg of a 30% oil dispersion, $5.8 \times 10^{-3}$ moles) was added and the reaction was stirred at room temperature for one hour when the hydrogen evolution had stopped and the potassium hydride had dissolved. This solution was cooled on ice and condensed ethylene oxide (23.6 gm, 0.535 moles) was added. The pressure flask was sealed and the reaction was stirred overnight at room temperature. The THF was removed under vacuum and the semi-solid residue was dissolved in chloroform (10 mL). This solution was added to diethyl ether (200 mL) and the mixture was cooled on ice which caused the polymer to separate as a powder. Most of the ether was removed by decantation and the solid polymer was then isolated by filtration of the remaining slurry. The solid was washed with ether and was then dried under vacuum to give the poly(ethylene)glycol conjugate as a white powder in a yield of 11.0 gm. The molecular weight, determined by NMR was 2 KD.

Example 5

Preparation of Peg-Nicotine Conjugates by Grafting: Amide Linkage to Nicotine at 1'-Position. Molecular Weight of about 3.5 KD

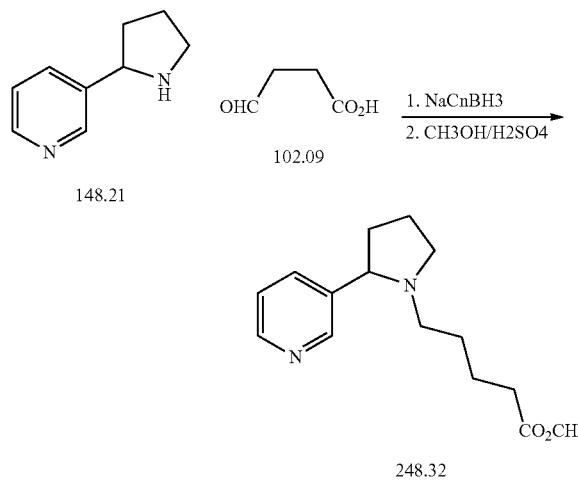

Nornicotine (2.18 gm, $1.47 \times 10^{-2}$ moles) and succinic semialdehyde (10 gm of a 15% solution in water, 1.5 gm, $1.47 \times 10^{-2}$ moles) were dissolved in acetonitrile (50 mL). This solution was stirred at room temperature as sodium cyanoborohydride (0.92 gm, $1.47 \times 10^{-2}$ moles) and acetic acid (0.88 gm, $1.47 \times 10^{-2}$ moles) was added. The reaction was stirred at room temperature overnight. The solution was filtered to remove some solids and the filtrates were evaporated to dryness under vacuum. Methanol (250 mL) was added along with concentrated sulfuric acid (1.44 gm, $1.47 \times 10^{-2}$ moles). Methanol (200 mL) was distilled from the reaction to remove boron. Additional methanol (100 mL) and sulfuric acid (5 gm) were added and the solution was stirred at room temperature overnight. Methanol (100 mL) was removed under vacuum and the remaining material was partitioned between methylene chloride (300 mL) and 10% potassium carbonate (200 mL). The methylene chloride phase was isolated and dried over magnesium sulfate. After filtering the solution free from the magnesium sulfate, the filtrates were evaporated under vacuum to provide the product as a pale yellow oil in a yield of 2.22 gm.

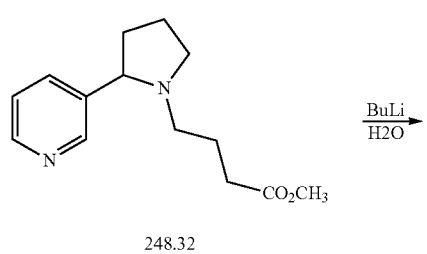

The methyl ester (248 mg, $1.0 \times 10^{-3}$ moles) was dissolved in THF (10 mL). Methanol (5 mL) and water (200 μL) were treated with n-butyl lithium (500 μL of 2.0M in hexanes, $1.0 \times 10^{-3}$ moles) and this solution was added to the THF solution of the methyl ester. The solution was refluxed for 30 minutes and was then left at room temperature overnight. The solvents were removed under vacuum and the solid residue was dried under vacuum. Ether (50 mL) was added and this mixture was stirred overnight. The solid which resulted was isolated by centrifugation and was washed with ether. After drying under vacuum the lithium salt was isolated as a white powder in a yield of 141 mg.

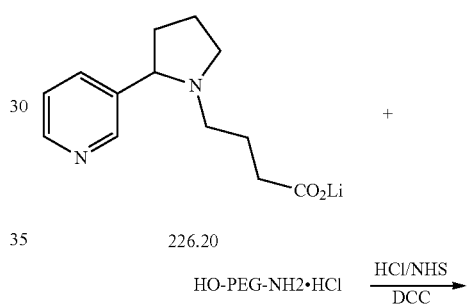

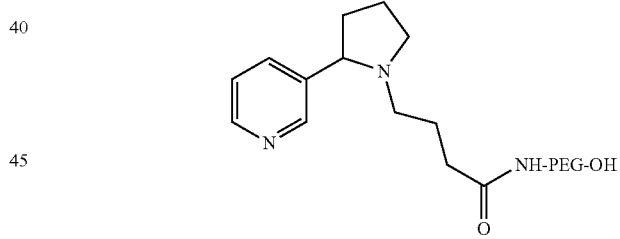

The nicotine carboxylic acid lithium salt (113 mg, $5.0 \times 10^{-4}$ moles) was stirred in DMF (2.0 mL) and hydrogen chloride dissolved in dioxane (4M) was added until an aliquot in water had a pH of 5.0 (250 μL). To this solution was added N-hydroxysuccinimide (57.5 mg, $5.0 \times 10^{-4}$ moles) and dicyclohexyl carbodiimide (103 mg, $5.0 \times 10^{-4}$ moles). This solution was stirred at room temperature overnight. The resulting slurry was treated with a solution of aminopoly(ethylene)glycol hydrochloride (750 mg, $2.14 \times 10^{-4}$ moles) and diisopropylethylamine (1.0 mL) in DMF (5.0 mL). This solution was stirred at room temperature overnight. The reaction was filtered free of solids and the filtrates were evaporated under vacuum. The residue was subjected to chromatography on silica gel using 15% methanol in methylene chloride as eluent. The fractions containing the product were pooled and evaporated to provide the polymer conjugate as a white waxy solid. This was dissolved in chloroform (5 mL) and the mixture was filtered free from

Example 6

Preparation of Peg-Nicotine Conjugate by Reaction with Ethylene Oxide: Ether Linkage to Nicotine at Position 3'-Position. Molecular Weight of about 5.0 KD. KHMDS as Base

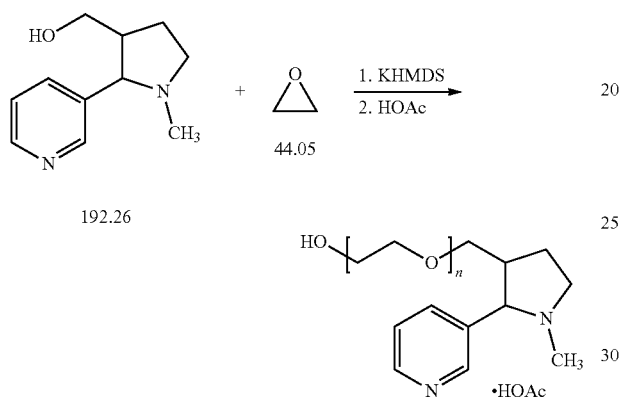

A solution of 3'-hydroxymethylnicotine (1.92 gm, 1.0×10$^{-2}$ moles) was prepared in dry dioxane (100 mL). This solution was brought to reflux and a portion of the dioxane (50 mL) was allowed to distill from the flask to remove water. The flask and contents were cooled to room temperature under argon. The solution was then cooled to 10° C. and a solution of potassium bis-trimethylsilylamide (20 mL, 0.5 M in toluene, 1.0×10$^{-2}$ moles) was added via syringe. This solution was kept at 10° C. under argon until needed for the next step.

Dry THF (150 mL) was placed in a pressure flask which was cooled in a dry ice/acetone bath under argon. Ethylene oxide (50 gm, 56.7 mL, 1.14 moles) was condensed in a cooled graduated cylinder and this was added to the cooled THF. To this solution was added the alkoxide solution from step 1 and the pressure flask was sealed. The reaction was allowed to warm to room temperature and after about 1.5 hours an exothermic reaction began. When the temperature reached 50° C. the flask and contents were placed in a water bath set at 25° C. and the reaction was stirred at that temperature overnight. The flask was opened and acetic acid (0.6 gm, 1.0×10$^{-2}$ moles) was added. After stirring for an additional 30 minutes, the polymer was precipitated by addition to diethyl ether (1.5 L) with stirring. The solid polymer was isolated by filtration and was washed with ether before being dried under vacuum. The yield of polymer was 48 gm (96%) with a molecular weight of about 5000 by GPC.

Example 7

Preparation of Peg-Nicotine Conjugate by Reaction with Ethylene Oxide: Ether Linkage to Nicotine at 3'-Position. Molecular Weight of about 4.7 KD. KH as Base

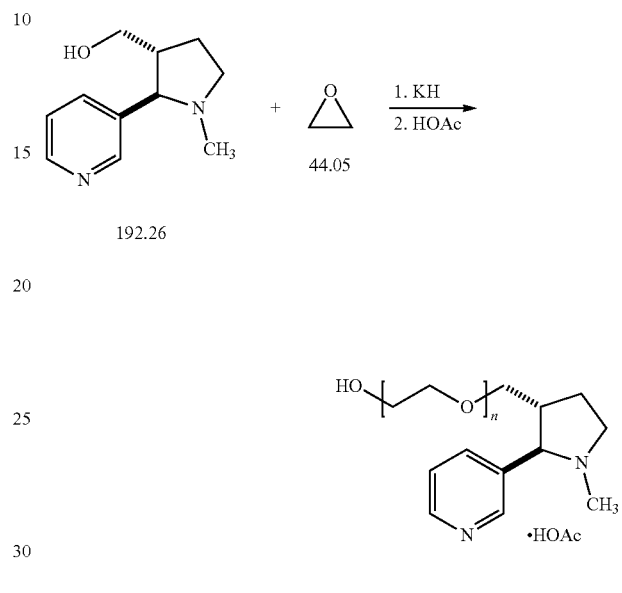

A solution of trans-3'-hydroxymethylnicotine (1.92 gm, 1.0×10$^{-2}$ moles) was prepared in dry dioxane (100 mL). This solution was brought to reflux and a portion of the dioxane (50 mL) was allowed to distill from the flask to remove water. The flask and contents were cooled to room temperature under argon. The solution was then cooled to 10° C. and potassium hydride (1.34 gm, 1.49 mL of a 30% suspension in mineral oil, 1.0×10$^{-2}$ moles) was added via pipette. This solution was stirred at room temperature for an hour at which point hydrogen evolution had stopped.

Dry THF (240 mL) was placed in a pressure flask which was cooled in an ice bath under argon. Ethylene oxide (50 gm, 56.7 mL, 1.14 moles) was condensed in a cooled graduated cylinder and this was added to the cooled THF. To this solution was added the alkoxide solution from above and the pressure flask was sealed. The reaction was allowed to warm to room temperature and the flask and contents were stirred at room temperature overnight. The flask was opened and acetic acid (0.6 gm, 1.0×10$^{-2}$ moles) was added. After stirring for an additional 30 minutes, the polymer was precipitated by addition to t-butyl methyl ether (1.0 L) with stirring. The solid polymer was isolated by filtration and was washed with TBME (2×100 mL). The polymer was partially dried by vacuum under a rubber dam before being recrystallized from 2-propanol (150 mL). The polymer was isolated by filtration and was washed with 2-propanol (50 mL) followed by TBME (100 mL) before being dried under vacuum. The yield of polymer was 42.2 gm (81%) with a molecular weight of about 4700 by NMR.

(Continued from previous page: a small amount of dicyclohexyl urea. The filtrates were added to diethyl ether (100 mL) and the precipitated polymer was isolated by centrifugation and dried under vacuum. The poly(ethylene)glycol/nicotine conjugate was isolated as a white powder in a yield of 480 mg.)

Example 8

Preparation of Peg-Nicotine Conjugate by Reaction with Ethylene Oxide: Ether Linkage to Nicotine at Position 3'-Position. Molecular Weight of about 4.9 KD. KH as Base

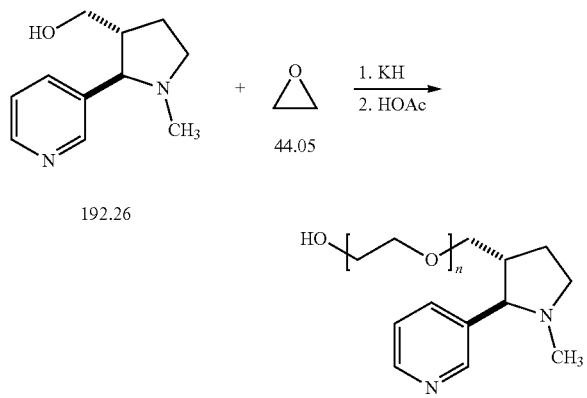

A solution of trans-3'-hydroxymethylnicotine (1.92 gm, $1.0\times10^{-2}$ moles) was prepared in dry 2-methyltetrahydrofuran (100 mL). This solution was brought to reflux and a portion of the 2-methyltetrahydrofuran (50 mL) was allowed to distill from the flask to remove water. The flask and contents were cooled to room temperature under argon. The solution was then cooled to 0° C. and potassium hydride (1.34 gm, 1.49 mL of a 30% suspension in mineral oil $1.0\times10^{-2}$ moles) was added via pipette. This mixture was stirred at room temperature for 2 hours at which point hydrogen evolution had stopped.

Dry 2-methyltetrahydrofuran (180 mL) was placed in a pressure flask which was cooled in an ice bath under argon. Ethylene oxide (50 gm, 56.7 mL, 1.14 moles) was condensed in a cooled, dry graduated cylinder and this was added to the cooled 2-methyl-tetrahydrofuran. To this solution was added the alkoxide solution from step 1 and the pressure flask was sealed. The reaction was allowed to warm to room temperature. After a period of about 2 hours an exothermic reaction commenced and the temperature rose to 55° C. over the course of 45 minutes. At this point a water bath was used to keep the temperature between 40-50° C. After another 30 minutes the temperature began to fall and the flask and contents were stirred at room temperature overnight. During this period a solid mass had formed and the reaction was heated to 50° C. to provide a pale yellow solution. The flask was opened and acetic acid (0.6 gm, $1.0\times10^{-2}$ moles) was added. After stirring for an additional 30 minutes a thin slurry had formed and this was added to t-butyl methyl ether (TBME, 1.0 L) with stirring. The solid polymer which separated was isolated by filtration and was washed with TBME (2×100 mL). The polymer was partially dried by vacuum under a rubber dam before being recrystallized from 2-propanol (200 mL). The polymer was isolated by filtration and was washed with 2-propanol (50 mL) followed by TBME (2×50 mL) before being dried under vacuum at 30° C. The yield of polymer was 42.7 gm (82.3%) with a molecular weight of about 4900 by NMR.

Example 9

Preparation of Peg-Nicotine Conjugate by Reaction with Ethylene Oxide: Ether Linkage to Nicotine at Position 3'-Position. Molecular Weight of about 0.6 KD. KH as Base

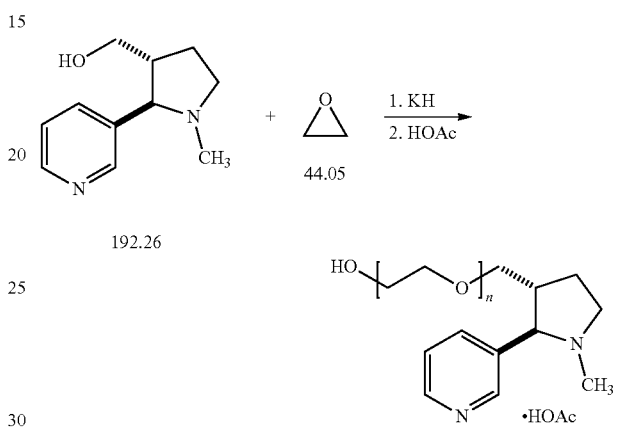

A solution of trans-3'-hydroxymethylnicotine (3.85 gm, $2.0\times10^{-2}$ moles) was prepared in dry 2-methyltetrahydrofuran (200 mL). This solution was brought to reflux and a portion of the 2-methyltetrahydrofuran (100 mL) was allowed to distill from the flask to remove water. The flask and contents were cooled in an ice bath under argon. The solution was then treated with potassium hydride (2.68 gm, 3.0 mL of a 30% suspension in mineral oil, $2.0\times10^{-2}$ moles) was added via pipette. This mixture was stirred at room temperature for 1 hour at which point hydrogen evolution had stopped. After cooling on ice again ethylene oxide (8.8 gm, 9.9 mL, 0.20 moles) was condensed in a cooled, dry graduated cylinder. The ethylene oxide was added to the cooled reaction and the pressure flask was sealed. The reaction was warmed to 55° C. in an oil bath which caused an exothermic reaction to begin and the temperature rose to 65° C. At this point a water bath was used to keep the temperature between 40-50° C. and the flask and contents were stirred at room temperature overnight. The flask was opened and acetic acid (3.6 gm, $6.0\times10^{-2}$ moles) was added. After stirring for an additional 30 minutes the hazy solution was decanted through a cotton plug and the 2-methyltetrahydrofuran was removed under vacuum. The residual oil was dissolved in methylene chloride and was washed with 10% potassium carbonate solution (200 mL). After drying over magnesium sulfate the solution was filtered and evaporated under vacuum. The residual oil was washed by decantation with hexane (3×50 mL) to remove mineral oil and was then purified by chromatography on silica gel using 10% methanol in methylene chloride as eluent. The fractions containing the product were pooled and evaporated to give the polymer as a pale yellow oil. The yield of polymer was 10.5 gm (83%) with a molecular weight of about 600 by NMR.

Example 10

Preparation of Peg-Nicotine Conjugate by Reaction with Ethylene Oxide: Ether Linkage to Nicotine at Position 3'-Position. Molecular Weight of about 2 KD. KH as Base

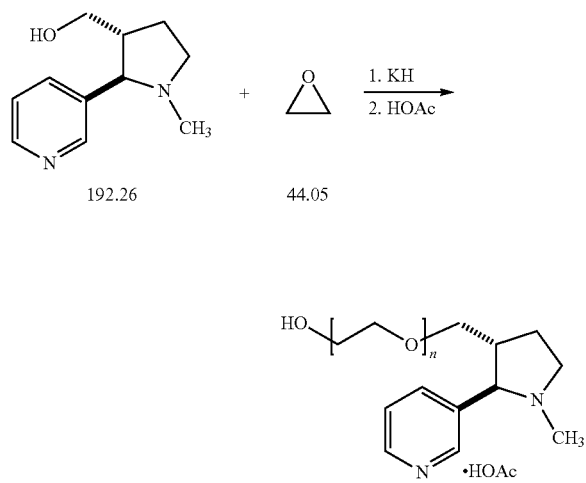

A solution of trans-3'-hydroxymethylnicotine (3.85 gm, $2.0 \times 10^{-2}$ moles) was prepared in dry 2-methyltetrahydrofuran (300 mL). This solution was brought to reflux and a portion of the 2-methyltetrahydrofuran (100 mL) was allowed to distill from the flask to remove water. The flask and contents were cooled in an ice bath under argon. The solution was then treated with potassium hydride (2.68 gm, 3.0 mL of a 30% suspension in mineral oil, $2.0 \times 10^{-2}$ moles) was added via pipette. This mixture was stirred at room temperature for 2 hours at which point hydrogen evolution had stopped. After cooling on ice again ethylene oxide (40 gm, 44.9 mL, 0.91 moles) was condensed in a cooled, dry graduated cylinder. The ethylene oxide was added to the cooled reaction and the pressure flask was sealed. The flask and contents were stirred at room temperature overnight. The flask was opened and acetic acid (1.8 gm, $3.0 \times 10^{-2}$ moles) was added. After stirring for an additional 30 minutes the hazy solution was decanted through a cotton plug and was added to diethyl ether (1.0 L) with vigorous stirring. After settling, the solid polymer was isolated by filtration and was washed with ether before being dried under vacuum. The solid polymer was dissolved in boiling tetrahydrofuran (300 mL) and, after cooling, the solution was filtered through a thin pad of Celite to remove insoluble material. The clear filtrates were diluted with diethyl ether (600 mL) and this solution was cooled on ice for 2 hours with stirring. The polymer which had separated was isolated by filtration and was washed with ether before being dried under vacuum. The yield of polymer was 30 gm (68%) with a molecular weight of about 2 KD by NMR.

Example 11

Preparation of a Polylactide—Block Poly(Ethylene)Glycol Nicotine Conjugate Using the Poly(Ethylene)Glycol Nicotine Conjugate from Example 1

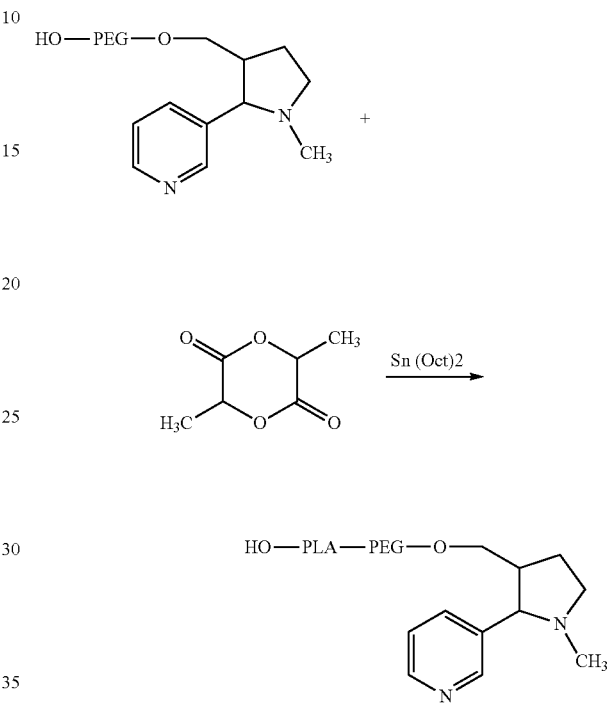

A 100 mL round bottom flask, equipped with a stir bar and reflux condenser was charged with the PEG/nicotine polymer (0.081 gm, $2.2 \times 10^{-5}$ moles) from example 1, D/L lactide (0.410 gm, $2.85 \times 10^{-3}$ moles) and anhydrous sodium sulfate (0.380 gm). This was dried under vacuum at 55° C. for 8 hours. The flask was cooled and flushed with argon and then dry toluene (10 mL) was added. The flask was placed in an oil bath set at 120° C., and once the lactide had dissolved, tin ethylhexanoate (5.5 mg, $1.36 \times 10^{-5}$ moles) was added. The reaction was allowed to proceed at 120° C. for 16 hours. After cooling to room temperature, water (15 mL) was added and stirring was continued for 30 minutes. Methylene chloride (200 mL) was added, and after agitation in a separatory funnel, the phases were allowed to settle. The methylene chloride layer was isolated and dried over anhydrous magnesium sulfate. After filtration to remove the drying agent, the filtrates were evaporated under vacuum to give the polymer as a colorless foam. The polymer was dissolved in tetrahydrofuran (10 mL) and this solution was slowly added to water (150 mL) with stirring. The precipitated polymer was isolated by centrifugation and the solid was dissolved in methylene chloride (10 mL). The methylene chloride was removed under vacuum and the residue was dried under vacuum. The yield was 0.38 gm.

Example 12

Preparation of a Polylactide—Block Poly(Ethylene)Glycol Nicotine Conjugate Using the Poly(Ethylene)Glycol Nicotine Conjugate from Example 3

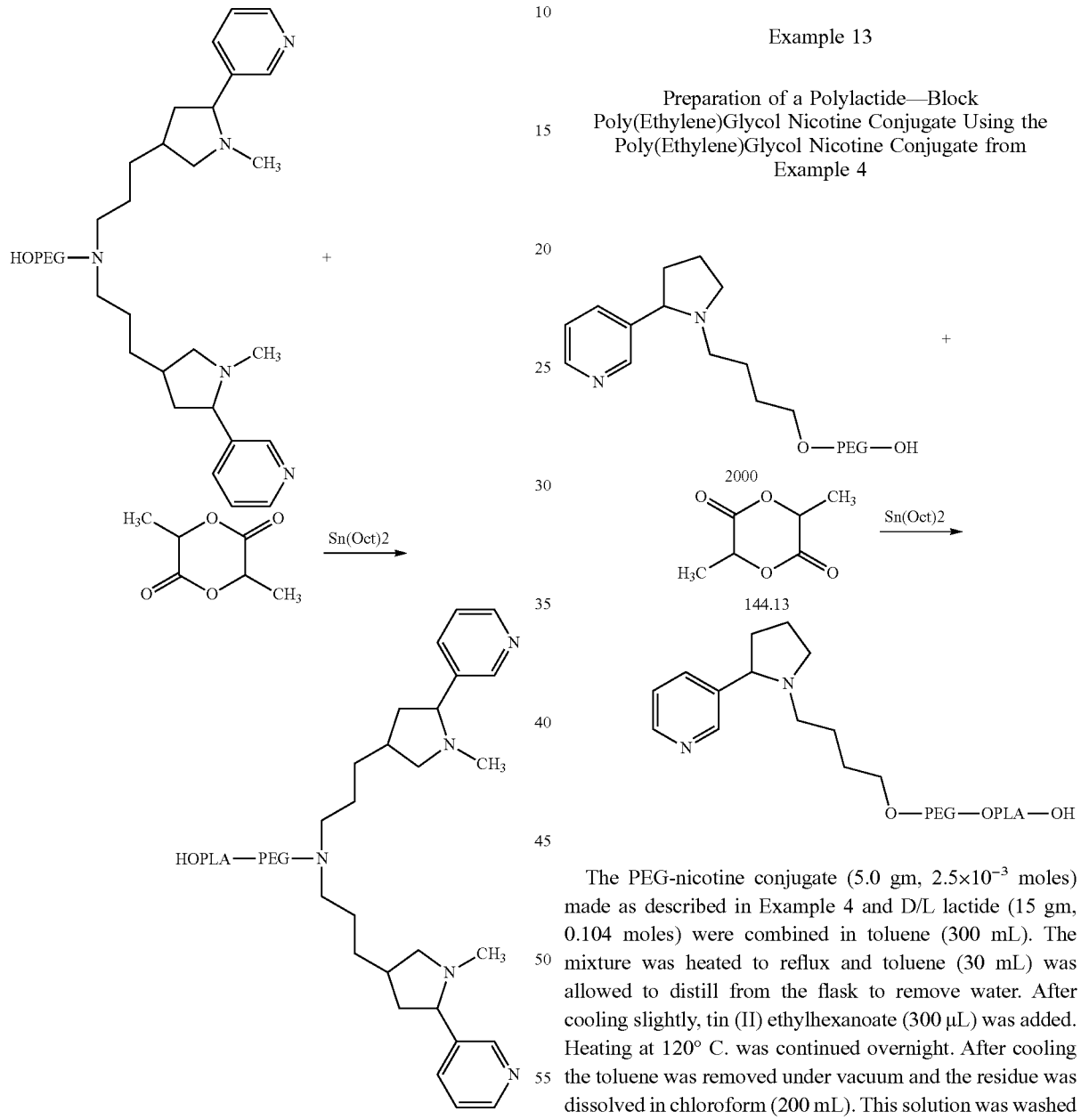

The poly(ethylene)glycol—nicotine conjugate made as described in Example 2 (190 mg, 4.86×10⁻⁵ moles), D/L lactide (911 mg, 6.3×10⁻³ moles), and sodium sulfate (844 mg) were dried under vacuum at 50° C. for 8 hours. To the dried mixture was added dry toluene (20 mL). The flask was purged with nitrogen and heated to 120° C. After stirring for 10 minutes, tin (II) ethylhexanoate (10 µL) was added and the reaction was stirred at 120° C. overnight under nitrogen. After cooling water (10 mL) was added and stirring was continued for 15 minutes. Methylene chloride (100 mL) was added along with additional water (20 mL). After agitation, the layers were settled and the organic layer was isolated and dried over magnesium sulfate. The solution was filtered and evaporated under vacuum to give the product as a pale brown waxy solid in a yield of 880 mg.

Example 13

Preparation of a Polylactide—Block Poly(Ethylene)Glycol Nicotine Conjugate Using the Poly(Ethylene)Glycol Nicotine Conjugate from Example 4

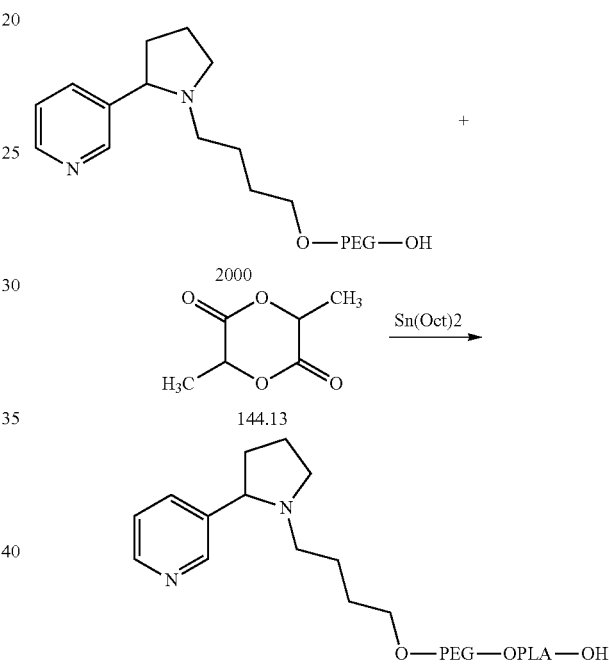

The PEG-nicotine conjugate (5.0 gm, 2.5×10⁻³ moles) made as described in Example 4 and D/L lactide (15 gm, 0.104 moles) were combined in toluene (300 mL). The mixture was heated to reflux and toluene (30 mL) was allowed to distill from the flask to remove water. After cooling slightly, tin (II) ethylhexanoate (300 µL) was added. Heating at 120° C. was continued overnight. After cooling the toluene was removed under vacuum and the residue was dissolved in chloroform (200 mL). This solution was washed with water (200 mL) and then dried over magnesium sulfate. After filtering the solution free from the magnesium sulfate, the filtrates were evaporated under vacuum to a volume of about 40 mL. This solution was stirred as 2-propanol (300 mL) was slowly added. After stirring for 5 minutes, the 2-propanol was decanted from the polymer mass and the polymer was dried under vacuum. The product was obtained as a light brown waxy solid in a yield of 14.8 gm. Molecular weight by NMR was about 9 KD.

Example 14

Preparation of a Polylactide—Block Poly(Ethylene)Glycol Nicotine Conjugate Using the Poly(Ethylene)Glycol Nicotine Conjugate from Example 6

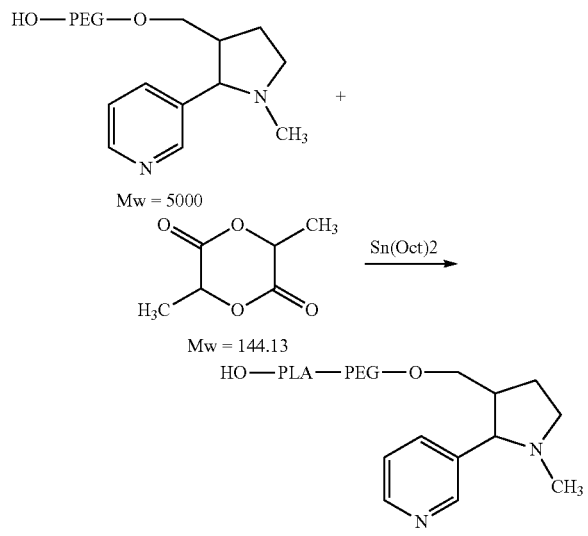

A 1000 mL round bottom flask, equipped with a stir bar and reflux condenser was charged with the PEG/nicotine polymer (5.0 gm, $1.0 \times 10^{-3}$ moles) described in example 6, D/L lactide (18.7 gm, 0.13 moles) and toluene (400 mL). A portion of the toluene (50 mL) was distilled from the flask to remove any water present and the solution was then cooled to about 100° C. and flushed with argon. The flask was placed in an oil bath set at 120° C. and tin ethylhexanoate (250 µL) was added. The reaction was allowed to proceed at 120° C. for 16 hours under argon with stirring. After cooling to room temperature the toluene was removed under vacuum and the remaining polymer was dissolved in methylene chloride (250 mL). Water (250 mL) was added and this mixture was shaken in a separatory funnel. The phases were allowed to settle and the methylene chloride layer was isolated and dried over anhydrous sodium sulfate. After filtration to remove the drying agent, the filtrates were evaporated under vacuum to a volume of approximately 50 mL. This solution was stirred as 2-propanol (300 mL) was added which caused the polymer to precipitate as a sticky mass. The precipitated polymer was isolated by decantation of the 2-propanol which was a milky fluid. Any remaining 2-propanol was removed under vacuum before the polymer was dried under high vacuum. The polymer was isolated as an off white solid in a yield of 17 gm (72%).

By NMR, the polymer had a lactide —CH to PEG —$CH_2CH_2$— ratio of 2.1/4. If the PEG has a molecular weight of 5000 then the PLA has a molecular weight of 17,200.

Example 15

Preparation of a Polylactide—Block Poly(Ethylene)Glycol Nicotine Conjugate Using the Poly(Ethylene)Glycol Nicotine Conjugate from Example 7

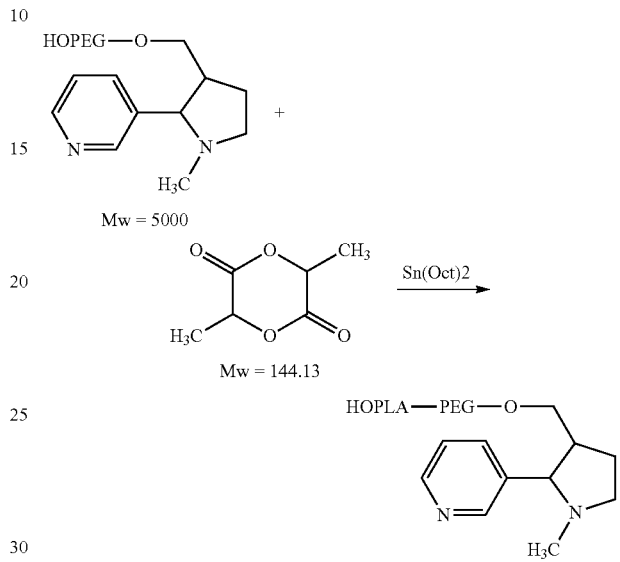

A 500 mL round bottom flask, equipped with a stir bar and reflux condenser was charged with the PEG/nicotine polymer (5.0 gm, $1.0 \times 10^{-3}$ moles), D/L lactide (18.7 gm, 0.13 moles) and toluene (100 mL). A portion of the toluene (50 mL) was distilled from the flask to remove any water present and the solution was then cooled to about 100° C. and flushed with argon. The flask was placed in an oil bath set at 120° C. and tin ethylhexanoate (200 µL) was added. The reaction was allowed to proceed at 120° C. for 16 hours under argon with stirring. After cooling to room temperature methylene chloride (250 mL) was added along with water (200 mL) and this mixture was shaken in a separatory funnel. The phases were allowed to settle and the methylene chloride layer was isolated and dried over anhydrous sodium sulfate. After filtration by decantation through a cotton plug to remove the drying agent, the filtrates were evaporated under vacuum to a volume of approximately 50 mL. This solution was stirred as 2-propanol (300 mL) was added which caused the polymer to precipitate as a sticky mass. The precipitated polymer was isolated by decantation of the 2-propanol which was a milky fluid. After washing with 2-propanol (50 mL) by decantation, any remaining 2-propanol was removed under vacuum before the polymer was dried under high vacuum. The polymer was isolated as an off white solid in a yield of 18 gm (76%).

By NMR, assuming that the PEG has a molecular weight of 5000 then the PLA has a molecular weight of 21,500 (theoretical PLA Mw=18,700).

Example 16

Preparation of a Polylactide—Block Poly(Ethylene)Glycol Nicotine Conjugate Using the Poly(Ethylene)Glycol Nicotine Conjugate from Example 8

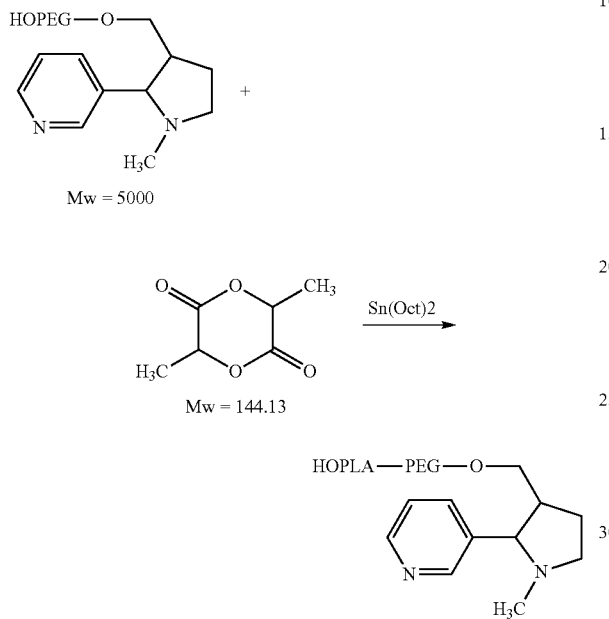

A 1.0 liter round bottom flask, equipped with a stir bar and reflux condenser was charged with the PEG/nicotine polymer (25.0 gm, $5.0 \times 10^{-3}$ moles) prepared as described in Example 8, D/L lactide (93.7 gm, 0.65 moles) and toluene (350 mL). A portion of the toluene (100 mL) was distilled from the flask to remove any water present and the solution was then cooled to about 100° C. and flushed with argon. The flask was placed in an oil bath set at 120° C. and tin ethylhexanoate (1.0 mL) was added. The reaction was allowed to proceed at 120° C. for 16 hours under argon with stirring. After cooling to room temperature, 2-propanol (500 mL) was added with vigorous stirring. After stirring for 15 minutes, the polymer mass was isolated by decantation of the liquid supernatant. To the polymer was added additional 2-propanol (500 mL). This mixture was heated to 65° C. with stirring to provide a hazy solution. The solution was cooled on ice to a temperature of 20° C. which caused the polymer to separate as a viscous mass. The supernatant was decanted from the polymer mass and remaining 2-propanol was removed under vacuum on a rotary evaporator before the polymer was dried under high vacuum at 30° C. for 3 days. The polymer was isolated as a white solid in a yield of 95 gm (80%).

By NMR, assuming that the PEG had a molecular weight of 5000 then the PLA had a molecular weight of 21,200. Remaining lactide was 1.2% by weight.

Example 17

Preparation of a Polylactide—Block Poly(Ethylene)Glycol Nicotine Conjugate Using Organic Base Catalyzed Ring Opening Polymerization

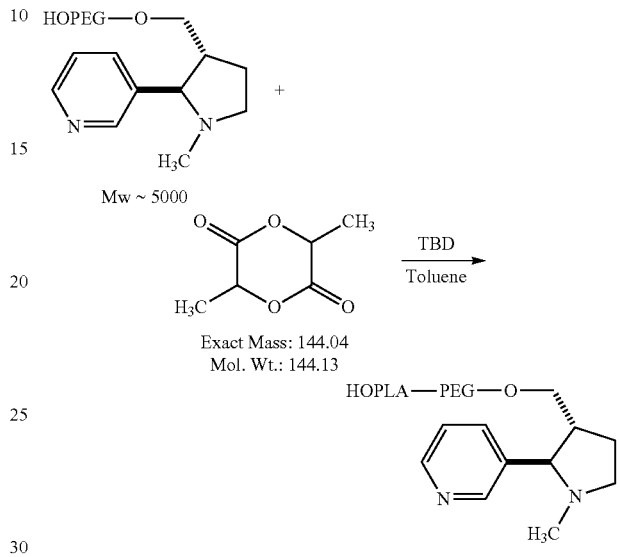

Step-1. Polymerization of dl-lactide with HO-PEG-Nic:

A 100 mL round bottom flask, equipped with a stir bar, an azeotrope collector with a reflux condenser with drying tube on top was charged with HO-PEG-Nic (2.5 gm, 0.0005 mol) prepared as in Example 8, dl-lactide recrystallized from EtOAc (9.4 gm, 0.065 mol) and anhydrous toluene (50 mL). A portion of the toluene (25-26 mL) was distilled from the flask to remove any water present (oil bath temperature is ca. 150° C.; it takes about 30 min to collect 25 mL of toluene and the distillate was not allowed to return to flask). The oil bath temperature was then lowered to ca. 105-110° C. while the azeotrope collector was removed and the drying tube on top of the condenser was replaced with argon balloon (or dry inert gas inlet). Once the oil bath temperature reached ca. 100° C., 1,5,7-triazabicyclo[4.4.0]dec-5-ene (TBD, 0.07 gm, 0.0005 mol) was added to the hot solution which was stirred overnight (17 h) under argon at oil bath temperature of 100° C. The oil bath was removed and the clear pale yellow solution was then cooled to RT (ice water was used for rapid cooling). The dense solution was then added to a solution of 2-propanol (100 mL) with vigorous stirring and a sticky gel-like polymer precipitated out of the solution (the reaction flask was rinsed with ca. 10 mL of 2-propanol to transfer the residue solution. Stirring could be difficult and gentle shaking could be applied). The mixture was stirred or shaken for ca. 10 min and then allowed to settle. The top milky 2-propanol supernatant was then decanted (residue 2-propanol could be removed on a Rotavap). The residue polymer was then dissolved in 30 mL of EtOAc and transferred to an additional funnel (the flask is rinsed with ca. 5 mL of EtOAc, total volume was about 55 mL).

Step-2. Isolation of PLA-PEG-NIC polymer:

A 500 mL RB flask equipped a stirring bar was charged with 250 mL of hexane and cooled with dry ice-acetone bath to <−50 C under dry condition (bath temperature −78° C.). With vigorous stirring, the polymer solution in EtOAc from Step-1 was added drop wise into the cold hexane from the addition funnel. Polymers precipitated out of the solution as lumpy solids during the addition. After the addition was complete, the cooling bath was removed and the resulting mixture was allowed to warm to room temperature. The lumpy solid polymers were collected by filtration on a Buchner funnel equipped with a Grade-3 filter paper. The flask and the polymers were rinsed with ca. 20 mL of hexane. After drying under vacuum at ambient temperature to remove residue solvent, PLA-PEG-NIC was isolated as white granular solids (11.0 g, 92.4%) (GPC: MW=24430, Mn=12600, PDI=1.9).

Example 18

Preparation of a Polylactide—Block Poly(Ethylene)Glycol Nicotine Conjugate Using Organic Base Catalyzed Ring Opening Polymerization

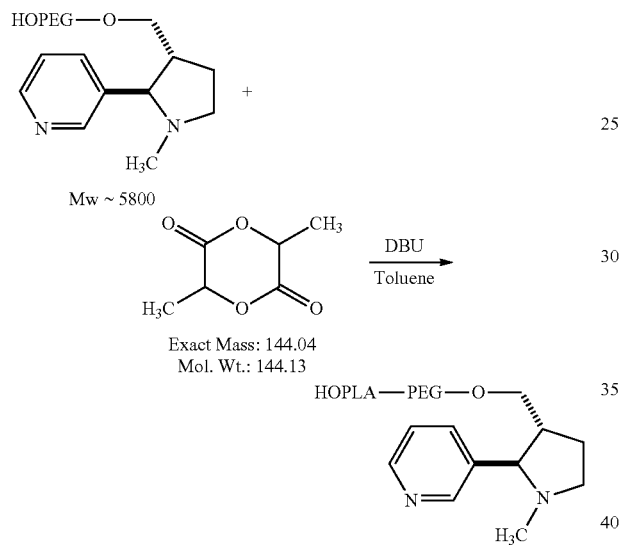

Step-1. Polymerization of dl-lactide with HO-PEG-Nic:

A 200 mL round bottom flask, equipped with a stir bar, an azeotrope collector with a reflux condenser with drying tube on top was charged with HO-PEG-Nic (MW: 5800 by GPC, 2.5 gm, 0.00043 mol), dl-lactide (9.4 gm, 0.065 mol) and anhydrous toluene (50 mL). A portion of the toluene (25 mL) was distilled from the flask to remove any water present (oil bath temperature was ca. 150° C.). The oil bath temperature was then lowered to ca. 100° C. while the azeotrope collector was removed and the drying tube on top of the condenser was replaced with argon balloon (or dry inert gas inlet). Once the oil bath temperature reached ca. 100° C., 1,8-Diazabicyclo[5.4.0]undec-7-ene (DBU, 0.065 gm, 0.00043 mol) was added to the hot solution which was stirred overnight (18 h) under argon at oil bath temperature of 100° C. The oil bath was removed and the clear pale yellow solution was then cooled to RT (ice water was used for rapid cooling). 2-propanol (100 mL) was then added to the solution with vigorous stirring and a sticky gel-like polymer precipitated out of the solution. The mixture was stirred for ca. 10 min and then allowed to settle. The top milky 2-propanol supernatant was then decanted. The residue polymer was then dissolved in 25 mL of EtOAc and transferred to an additional funnel (the flask was rinsed with ca. 5 mL of EtOAc, total volume was about 57 mL).

Step-2. Isolation of PLA-PEG-NIC polymer:

A 500 mL RB flask equipped a stirring bar was charged with 250 mL of heptane and cooled with dry ice-acetone bath to <−50° C. under dry condition (bath temperature −78° C.). With vigorous stirring, the polymer solution in EtOAc from Step-1 was added drop wise into the cold heptane from the addition funnel. Polymers precipitated out the solution as hard solids during the addition. After the addition was complete, cooling bath was removed and the resulting mixture was allowed to warm to room temperature. The hard solid polymers were collected by filtration on a Buchner funnel equipped with a Grade-3 filter paper. The flask and the polymers were rinsed with ca. 50 mL of heptane. After drying under vacuum at ambient temperature to remove residue solvent, PLA-PEG-NIC was isolated as white granular solids (11.1 g, 94%) (GPC: MW=24680, PDI=1.4).

Example 19

Preparation of (2S', 3S')- and (2R', 3R')-hydroxylmethylnicotine

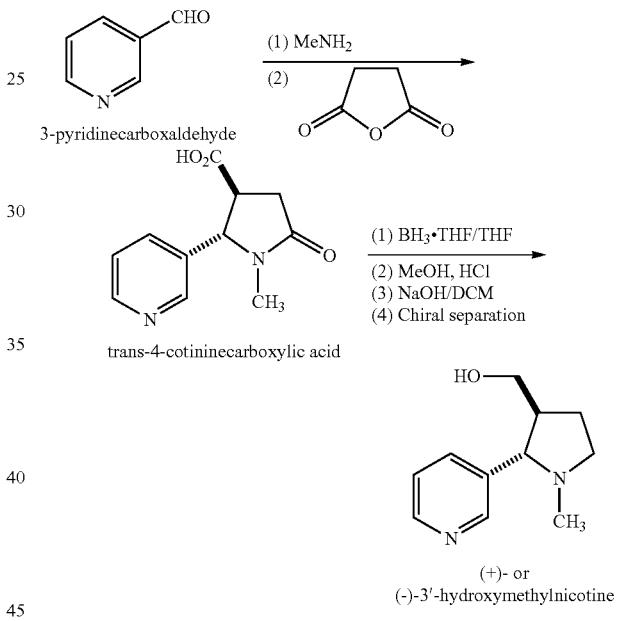

Preparation of racemic trans-4-cotininecarboxylic acid

A one liter flask was charged with 3-pyridinecarboxaldehyde (107 g, 1.0 mol, 97%) and 400 mL of toluene (ACS reagent grade). The solution was cooled with ice water and a solution of methylamine in methanol (33 wt %, 185 mL, 1.5 mol) was added via an addition funnel. The resulting solution was stirred at rt for 1 h. K2CO3 (50 g) was added and the mixture was stirred at rt for 1 h and then 30 g of anhydrous MgSO4 was added. The mixture was filtered and the solid was washed with 2×50 L of toluene. The filtrate was then refluxed for about 1 h. The solution was then concentrated and azeotroped with toluene or heptane to dryness to give crude N-3-pyridylenemethylamine which was used without further purification (H NMR).

The crude imine was then dissolved in m-xylene (120 mL) and succinic anhydride (100 g, 1.0 mol, 1.0 eq) was added. The resulting mixture was heated at reflux for 22-30 h (a dark brown heavy mixture). The mixture was cooled to rt and the crude product solidified at bottom of the flask. m-Xylene was then decanted away (although not tried, m-xylene could be left in the flask during the workup) and the residue solids were carefully dissolved with 10% aq. NaHCO3 (1.6 L) with cooling (release of CO2) to ca. pH 8.5. The aqueous mixture (remaining m-xylene could be removed at this step) was washed with DCM (2×350 mL) and then de-colorized with activated carbon (10 g) (solution was still brown in color).

The pH of the aqueous solution was then adjusted to 4.7 with conc. H3PO4 with cooling to precipitate the product. The mixture was cooled overnight. The white solids were collected and washed with cold water until no color in washes. The solids were dried at 40° C. under vacuum until constant weight as trans-4-cotininecarboxylic acid (103 g). The combined aqueous filtrates (ca. 2 L) were further concentrated to ca. 300 mL and cooled to precipitate out more products (21 g). Total recovery was 124 g (56% yd, H NMR). The product was used without further purification.

Preparation of racemic trans-3'-hydroxymethylnicotine

An dried 2-L three neck flask equipped with a thermometer, an addition funnel and a reflux condenser was charged with trans-4-cotininecarboxylic acid from procedure-(1) (36 g, 0.16 mol, 1.0 eq) and dry THF (200 mL) under argon. The white suspension was cooled with ice water (internal temperature 5-10 C). BH3.THF (1.0 M in THF, 800 mL, 0.8 mol, 5 eq) was added drop-wise through the funnel while maintaining the internal temperature at 10-20 C (gas evolution during addition). After addition, the resulting mixture was heated to reflux for 40 h (a clear solution was formed. The product forms a strong complex with borane. In order to check the reaction, an aliquot was quenched with 6 N HCl with heating and then basified with NaOH and extracted with DCM. On TLC (20% MeOH in DCM), the original less polar borane complex was converted to the more polar product). The solution was cooled with ice water and MeOH (200 mL) was added drop wise at 10-20° C. with caution to destroy excess BH3.THF (gas evolution). The mixture was stirred at rt for 1 h and was concentrated to ca. 150 mL in volume. The concentrate was cooled and conc. HCl (36%, 12 N, 130 mL, 1.6 mol) was added with caution. The solution was warmed to rt and concentrated to remove most of the MeOH. The residual aq. solution was heated at reflux overnight (ca. 14 h) to destroy the borane-product complex and then cooled with ice water. DCM (300 mL) was added and solid NaOH (ca. 40 g) (the product is soluble in water and minimum amount of aq. phase is maintained) was added in small portions with caution (exotherm) to adjust pH to 10-11 (a thick slurry was formed due to salt formation). The mixture was filtered to remove the solids and the filter cake was washed with DCM (2×50 mL). The DCM phase was separated from the combined filtrates. The aq. phase was extracted with 3×100 mL of DCM. The combined DCM phase was dried over Na2SO4 and concentrated to dryness to give crude trans-3'-hydroxymethylnicotine as a yellow liquid (ca. 30 g). The crude product was further purified by vacuum distillation to give pure trans-3'-hydroxymethylnicotine (bp 145-155 C/3-4 torr; recovery: 23.4 g from 30 g crude, 76%). Alternatively, the crude product can also be purified by chromatography on silica gel eluting with MeOH in DCM.

Preparation of Optically Pure (+)-(2R', 3R') or (−)-(2S', 3S')-hydroxymethylnicotine by Chiral Resolution of Optically Racemic trans-3'-hydroxymethylnicotine Racemic trans-3'-hydroxymethylnicotine prepared from above procedure is subjected to chiral separation on a Chiral Daicel IC column (21×250 mm, 5 µm). The detailed conditions are as follows:

Column: Chiral Daicel IC, 21×250 mm, 5 µm
Mobile phase: CO2/MeOH (0.5% Diethylamine)=70:30
Flow rate: 50 mL/min
Injection amount: 1.2 mL (100 mg)
Temperature: 40° C.
Wave length: 254 nm Sample preparation: 27 g of racemic trans-3'-hydroxymethylnicotine is dissolved in 324 mL MeOH (containing 0.5% diethylamine).

Operational Procedure: A preparative SFC80 (Waters) instrument is set-up using stack-injection program (1.2 mL per injection, 100 mg compound, total 270 injections). A binary pump is used to deliver CO2 (liquid) and MeOH (with total 0.5% DEA). Each cycle is set-up for 4 min. The Peak #1 is collected during 2.05-2.25 min and Peak #2 is collected during 2.30-2.55 min. After the completion, CO2 is evaporated, all Peak #1 and Peak #2 fractions are combined separately. The residues are concentrated at 35-45° C./5-10 mmHg until dryness.

Thus, from 27 g of racemic trans-3'-hydroxymethylnicotine, 10.1 g of (−)-(2S', 3S')-hydroxymethylnicotine (Peak #1. Chemical purity: 99.8%, ee: 98.76%, Optical rotation: $[\alpha]_D 25=-42.678°$, c=2.14% in MeOH) and 8.3 g of (+)-(2R', 3R')-hydroxymethylnicotine (Peak #2. Chemical purity: 99.9%, ee: 99.9%, Optical rotation: $[\alpha]_D^{25}=+42.689°$ c=2.12% in MeOH) are obtained.

The absolute configurations are determined by X-ray crystallography on the ester derivative of (−)-3'-hydroxymethylnicotine (Peak #1) with 6-S-methoxynaphthalinyl-2-propanoic acid which confirmed that (−)-3'-hydroxymethylnicotine has the (2S', 3S')-configuration and (+)-3'-hydroxymethylnicotine has the (2R', 3R')-configuration.

Example 20

Preparation of (2S', 3S')- and (2R', 3R')-PEG-Nic by Reaction with Ethylene Oxide Following Example 8, (2R', 3R')-PEG-Nic with MW of 5580 or (2S', 3S')-PEG-Nic with MW of 4280 was prepared by ring opening polymerization of ethylene oxide with the corresponding (+)-(2R', 3R') or (−)-(2S', 3S')-hydroxymethylnicotine from Example 19.

Example 21

Preparation of PEG-Nicotine Conjugates: Nicotine Linker at 6-Position. Molecular Weight of about 3.5 KD. (Prophetic)

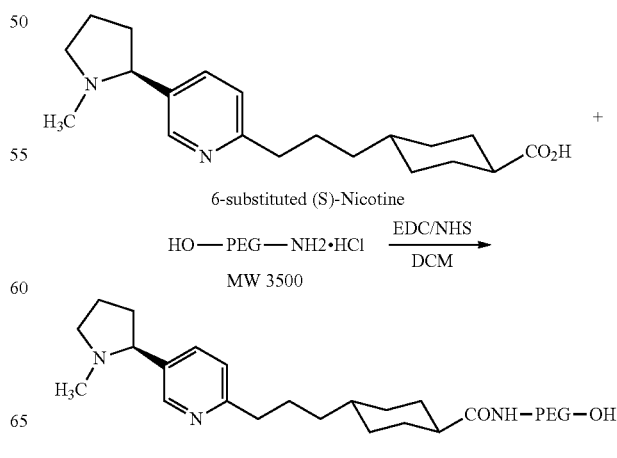

6-substituted (S)-nicotine ((S)-trans-4-[3-(5-(1-methyl-2-pyrrolidnyl)-2-pyridinyl)propyl]cyclohexanecarboxylic acid) is prepared according to procedures as described in PCT WO 01/70730 A1 (165 mg, 0.5 mmol, 1.1 eq) and HO-PEG-NH2.HCl (MW 3500, 1.6 g, 0.45 mmol, 1.0 eq) are dissolved in dry DCM (10 mL). EDC.HCl (115 mg, 0.6 mmol, 1.2 eq) and N-hydroxysuccinimide (NHS) (70 mg, 0.6 mmol, 1.2 eq) are added, followed by triethylamine (0.2 mL). The mixture is stirred at ambient temperature overnight under nitrogen. The solution is concentrated and the residue is precipitated out from 100 mL diethyl ether. After washing with 10% MeOH in diethyl ether (100 mL) and diethyl ether (50 mL), the resulting PEG-(S)-Nicotine conjugate is dried under vacuum as a white solid (1.5 g, MW ca. 3500).

Example 22

Preparation of a Polylactide—Block Poly(Ethylene)Glycol Nicotine Conjugate Using the Poly(Ethylene)Glycol Nicotine Conjugate from Example 21 (Prophetic)

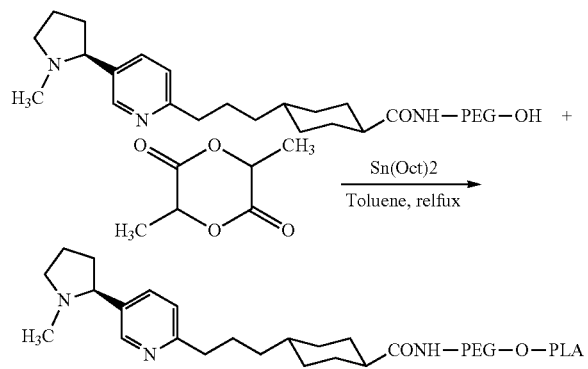

A mixture of PEG-(S)-Nicotine conjugate from Example 21 (1.5 g, 0.4 mmol, 1.0 eq) and dl-lactide (7.9 g, 59 mmol, 138 eq) in 60 mL dry toluene is heated to reflux while ca. 20 mL of toluene is collected via azeotrope distillation to remove residual water in the reaction. The resulting solution is cooled to ca. 90 C and Sn(Oct)2 (81 mg, 0.2 mmol) is added. The solution is then heated to reflux under argon overnight (15-18 h) and cooled with ice water to ambient temperature. The cooled solution is then added to 300 mL of 2-propanol with vigorous stirring and a gel-like polymer is formed. The mixture is stirred or shaken for 20 min and allowed to settle. The top 2-propanol layer is decanted and the residue is washed sequentially with 2-propanol (50 mL) and t-butyl methylether (50 mL). The gel-like polymer is then dried under vacuum at 35 C to constant weight to give PLA-PEG-(S)-nicotine conjugate as a white solid (ca. 8 g recovery, Mn by H NMR is 23,000).

Example 23

Preparation of Polypropylenesulfide-Nicotine Conjugates by Reaction with Propylene Sulfide: Thioether Linkage to Nicotine at Position 6. DBU Catalysis (Prophetic)

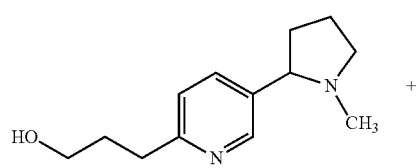

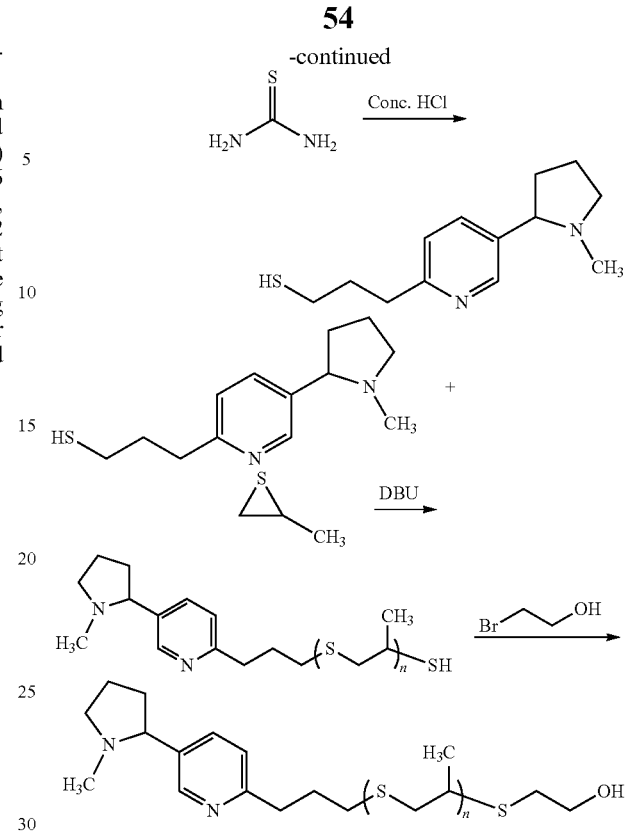

6-hydroxypropylnicotine is prepared according to the literature preparation [Seeman et al, Journal of Organic Chemistry 51, 1548, (1986)]. This compound is converted to the mercaptan by reaction with thiourea in the presence of concentrated hydrochloric acid [Buter and Kellogg, Organic Syntheses, Collective Volume 8, 592, (1993)]. This mercaptan is used to initiate ring opening polymerization of propylene sulfide in the following manner.

A solution of 6-mercaptopropylnicotine (4.73 gm, 2.0×$10^{-2}$ moles) is prepared in dry 2-methyltetrahydrofuran (300 mL). This solution is brought to reflux and a portion of the 2-methyltetrahydrofuran (100 mL) is allowed to distill from the flask to remove water. The flask and contents are cooled in an ice bath and the flask is flushed with argon. The solution is then treated with DBU (1,8-diazabicyclo[5,4,0]undec-7-ene, 3.04 gm, 2.0×$10^{-2}$ moles). This mixture is stirred at room temperature for 1 hour and is then cooled on ice again. Propylene sulfide (66.7 gm, 70 mL, 0.90 moles) is added to the cooled reaction and the flask is sealed under argon. The flask and contents are stirred at room temperature for 4 hours after which 2-bromoethanol (3.1 gm, 1.77 mL, 2.5×$10^{-2}$ moles) is added. Stirring at room temperature is continued overnight. The resulting solution is evaporated under vacuum and the oily residue is dissolved in methylene chloride (300 mL) and this solution is washed with water (2×100 mL). After drying over sodium sulfate, the solution is filtered and evaporated under vacuum. After drying under high vacuum there is obtained 51.8 gm (70%) of a polypropylene sulfide (PPS) conjugate of nicotine terminated with an alcohol function.

Example 24

Preparation of a Polycaprolactone—Block Polypropylene Sulfide-Nicotine Conjugate Using the Polypropylene Sulfide-Nicotine Conjugate from Example 21 (Prophetic)

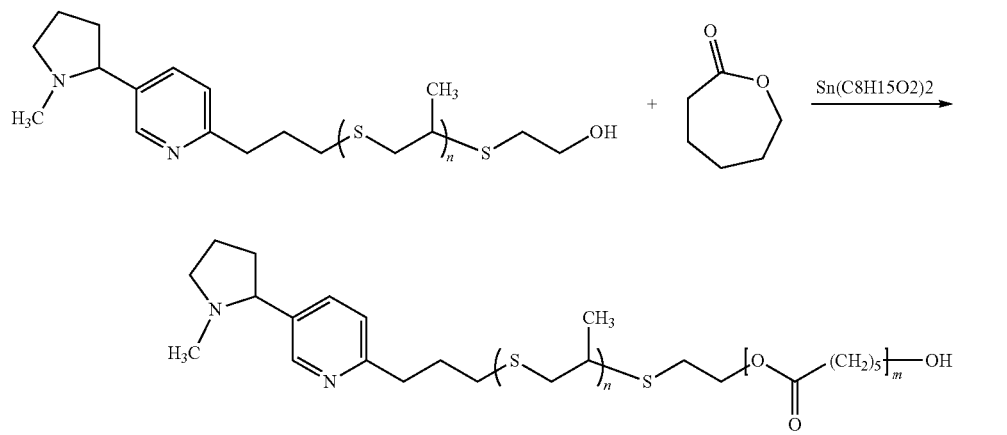

The PPS-nicotine conjugate (9.24 gm, $2.5 \times 10^{-3}$ moles), made as described in Example 21, and ε-caprolactone (11.9 gm, 0.104 moles) are combined in toluene (300 mL). The mixture is heated to reflux and toluene (30 mL) is allowed to distill from the flask to remove water. After cooling slightly, tin (II) ethylhexanoate (300 µL) is added. Heating at 120° C. is continued overnight. After cooling the toluene is removed under vacuum and the residue is dissolved in chloroform (200 mL). This solution is washed with water (200 mL) and then dried over magnesium sulfate. After filtering the solution free from the magnesium sulfate, the filtrates are evaporated under vacuum to a volume of about 40 mL. This solution is stirred as 2-propanol (300 mL) is slowly added. After stirring for 5 minutes, the 2-propanol is decanted from the polymer mass and the polymer is dried under vacuum. The product was obtained as a light brown waxy solid in a yield of 16 gm (76%).

Example 25

Preparation of Polyethyloxazoline-Nicotine Conjugate by Reaction with 2-ethyl-2-oxazoline: Amine Linkage to Nicotine at Position 3'. (Prophetic)

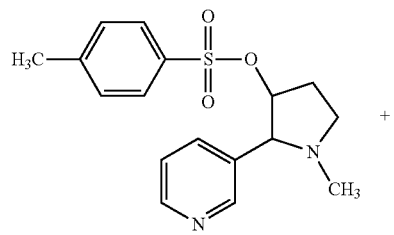

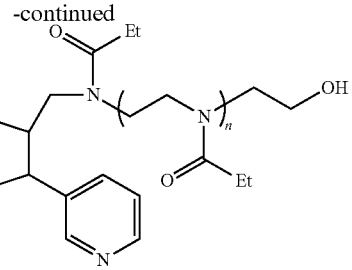

The toluenesulfonate ester of 3'-hydroxymethylnicotine is prepared by the literature method [Sanderson et al, *International Immunopharmacology*, 3, 137, (2003)].

A solution of the toluenesulfonate ester of 3'-hydroxymethylnicotine (1.68 gm, $5.0 \times 10^{-3}$ moles) and 2-ethyl-2-oxazoline (24.8 gm, 0.25 moles) in acetonitrile (75 mL) is heated in a sealed pressure flask under argon at 100° C. for 24 hours. After cooling to room temperature, the flask is opened and a solution of potassium hydroxide in methanol (1.0 N, 10 mL). After stirring for 30 minutes, the solution is filtered through a pad of silica and the filtrate is added to diethyl ether (1.0 L) to precipitate the polymer. The solid polymer is isolated by filtration and dried under vacuum.

Example 26

Preparation of Polyethyleneimine-Nicotine Conjugate by Hydrolysis of Polyethyloxazoline-Nicotine: Amine Linkage to Nicotine at Position 3'. (Prophetic)

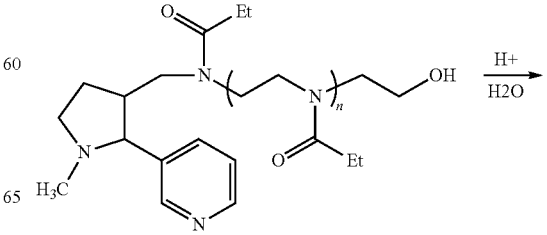

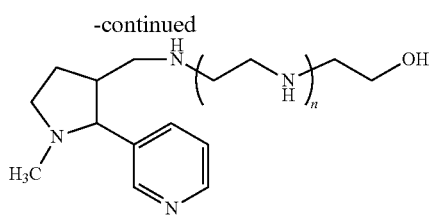

To a mixture of ethanol (100 mL) and concentrated hydrochloric acid (50 mL) is added the polyethyloxazoline-nicotine conjugate from above (10.0 gm). This mixture is stirred under argon and heated at reflux for 24 hours. After cooling, the ethanol and excess hydrochloric acid are removed under vacuum. The residue is stirred in ethanol (100 mL) and a solution of potassium hydroxide (5.6 gm, 0.10 moles) in ethanol (100 mL) is slowly added with stirring. After the addition is complete, the potassium chloride is removed by filtration and the filtrates are evaporated under vacuum. The residual polymer is dried under high vacuum.

Example 27

Preparation of a polylactide-co-glycolide—Block Ethyloxazoline-Nicotine Conjugate Using the Polyoxazoline-Nicotine Conjugate from Example 24. (Prophetic)

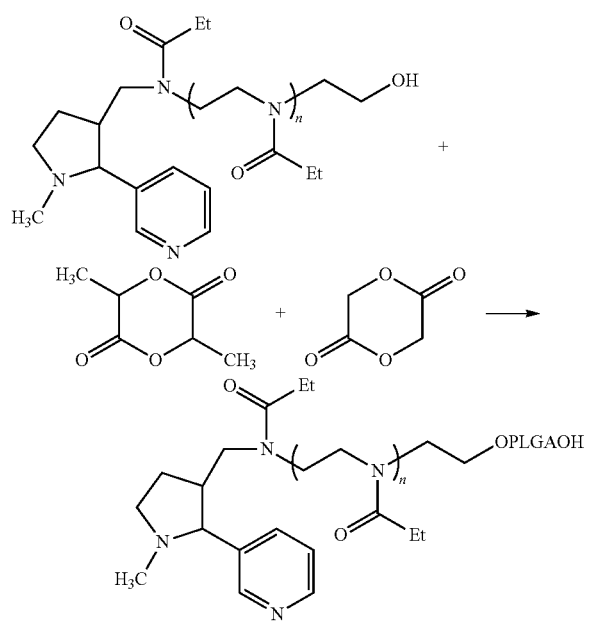

A 500 mL round bottom flask, equipped with a stir bar and reflux condenser is charged with the polyethyloxazoline-nicotine polymer (5.0 gm, $1.0 \times 10^{-3}$ moles) from example 24, D/L lactide (14.4 gm, 0.10 moles), glycolide (3.48 gm, 0.03 moles) and toluene (100 mL). A portion of the toluene (50 mL) is distilled from the flask to remove any water present and the solution is then cooled to about 100° C. and flushed with argon. The flask is placed in an oil bath set at 120° C. and tin ethylhexanoate (200 μL) is added. The reaction is allowed to proceed at 120° C. for 16 hours under argon with stirring. After cooling to room temperature methylene chloride (250 mL) is added along with water (200 mL) and this mixture is shaken in a separatory funnel. The phases are allowed to settle and the methylene chloride layer is isolated and dried over anhydrous sodium sulfate. After filtration by decantation through a cotton plug to remove the drying agent, the filtrates are evaporated under vacuum to a volume of approximately 50 mL. This solution is stirred as 2-propanol (300 mL) is added which causes the polymer to precipitate as a sticky mass. The precipitated polymer is isolated by decantation of the 2-propanol. After washing with 2-propanol (50 mL) by decantation, any remaining 2-propanol is removed under vacuum before the polymer is dried under high vacuum.

Example 28

Preparation of Amide-Nicotine Conjugates by Polymerization of an Amino Acid N-carboxyanhydride: Amine Linkage to Nicotine at Position 1'. (Prophetic)

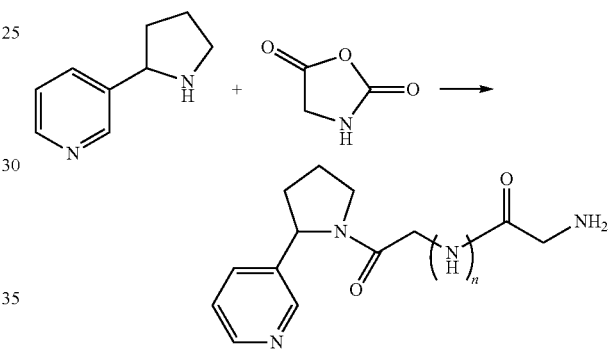

A solution of nornicotine (0.74 gm, $5.0 \times 10^{-3}$ moles) and 2,5-oxazolidinedione
(25.3 gm, 0.25 moles) in dry dichloromethane (100 mL) is stirred under argon at room temperature for 5 days. The resulting solution is slowly poured into diethyl ether (1 L) with vigorous stirring. The polymer which separates is isolated by filtration, washed with ether and dried under vacuum.

Example 29

Synthetic Nanocarriers, Containing the Adjuvant Resiquimod and a Protein, using the Inventive Compound of Example 16

Resiquimod (aka R848) was synthesized according to the synthesis provided in Example 99 of U.S. Pat. No. 5,389,640 to Gerster et al. A PLA-PEG-nicotine conjugate was prepared at Selecta Biosciences using the method of example 16. PLA was prepared by a ring opening polymerization using D,L-lactide (MW=approximately 15 KD–18 KD). The PLA-PEG-nicotine and PLA structures were confirmed by NMR and the molecular weights were determined by GPC. The polyvinyl alcohol (Mw=11 KD–31 KD, 85% hydrolyzed) was purchased from VWR scientific. These were used to prepare the following solutions:
1. Resiquimod in methylene chloride @ 7.5 mg/mL
2. PLA-PEG-nicotine in methylene chloride @ 100 mg/mL
3. PLA in methylene chloride @ 100 mg/mL 4. Peptide in water @ 10 mg/mL, the peptide having the sequence:

```
                                          SEQ ID NO. 1
ILMQYIKANSKFIGIPMGLPQSIALSSLMVAQ
```

5. Polyvinyl alcohol in water @50 mg/mL.

Solution #1 (0.4 mL), solution #2 (0.4 mL), solution #3 (0.4 mL) and solution #4 (0.1 mL) were combined in a small vial and the mixture was sonicated at 50% amplitude for 40 seconds using a Branson Digital Sonifier 250. To this emulsion was added solution #5 (2.0 mL) and sonication at 35% amplitude for 40 seconds using the Branson Digital Sonifier 250 formed the second emulsion. This was added to a beaker containing water (30 mL) and this mixture was stirred at room temperature for 2 hours to form the nanoparticles. A portion of the nanoparticle dispersion (1.0 mL) was diluted with water (14 mL) and this was concentrated by centrifugation in an Amicon Ultra centrifugal filtration device with a membrane cutoff of 100 KD. When the volume was about 250 μL, water (15 mL) was added and the particles were again concentrated to about 250 μL using the Amicon device. A second washing with phosphate buffered saline (pH=7.5, 15 mL) was done in the same manner and the final concentrate was diluted to a total volume of 1.0 mL with phosphate buffered saline. This provided a final nanoparticle dispersion of about 2.7 mg/mL in concentration. These nanoparticles contained both resiquimod and a protein encapsulated within the nanoparticle with nicotine displayed on the surface of the nanoparticle.

Example 30

Synthetic Nanocarriers Containing the Adjuvant Resiquimod, Using the Inventive Compound of Example 13

Resiquimod (aka R848) was synthesized according to the synthesis provided in Example 99 of U.S. Pat. No. 5,389,640 to Gerster et al and was attached to PLA using HOBT as condensing agent. The PLA-PEG-nicotine conjugate was prepared at Selecta Biosciences using the method of Example 13. PLA was prepared by a ring opening polymerization using D,L-lactide (MW=approximately 15 KD-18 KD). The PLA-PEG-nicotine and PLA structures were confirmed by NMR and the molecular weights were determined by GPC. The polyvinyl alcohol (Mw=11 KD-31 KD, 85% hydrolyzed) was purchased from VWR scientific. These were used to prepare the following solutions:

1. PLA-R848 conjugate @ 100 mg/mL in methylene chloride
2. PLA-PEG-nicotine in methylene chloride @ 100 mg/mL
3. PLA in methylene chloride @ 100 mg/mL
4. Polyvinyl alcohol in water @50 mg/mL.

Solution #1 (0.25 to 0.75 mL), solution #2 (0.25 mL), and solution #3 (0.25 to 0.5 mL) were combined in a small vial and the mixture was sonicated at 50% amplitude for 40 seconds using a Branson Digital Sonifier 250. To this emulsion was added solution #4 (2.0 mL) and sonication at 35% amplitude for 40 seconds using the Branson Digital Sonifier 250 formed the second emulsion. This was added to a beaker containing phosphate buffer solution (30 mL) and this mixture was stirred at room temperature for 2 hours to form the nanoparticles. To wash the particles a portion of the nanoparticle dispersion (7.0 mL) was transferred to a centrifuge tube and spun at 5,300 g for one hour, supernatant was removed, and the pellet was re-suspended in 7.0 mL of phosphate buffered saline. The centrifuge procedure was repeated and the pellet was re-suspended in 2.2 mL of phosphate buffered saline for a final nanoparticle dispersion of about 10 mg/mL. These nanoparticles contained the adjuvant, resiquimod, covalently attached to PLA situated in the interior of the nanoparticle with nicotine displayed on the surface of the nanoparticle.

Example 31

Immunization with Synthetic Nanocarriers from Example 29 or 30.(Prophetic)

Groups of five mice were immunized three times (subcutaneously, hind limbs) at 2-week intervals (days 0, 14 and 28) with 100 μg of synthetic nanocarriers from Example 29 or 30 and serum anti-nicotine antibodies were then measured on days 26, 40 and 54. EC50 for anti-nicotine antibodies are measured with a standard ELISA assay.

What is claimed is:

1. A compound comprising:

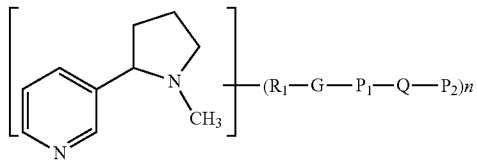

Formula II wherein:
- P₁ is a polymer comprising monomeric residues of unsubstituted or substituted ethylene oxide, ethylene sulfide and/or ethyleneimine, and copolymers thereof, with the proviso that if R₁ is covalently bound to a methyl residue present at the pyrrolidine nitrogen at position 1' of the nicotine residue, then P₁ is not a polymer comprising 1-40 monomeric residues of unsubstituted ethylene oxide;
- G comprises oxygen, sulfur, or —NR—, wherein R comprises alkyl, substituted alkyl, acyl, aryl, or substituted aryl;
- Q comprises oxygen, sulfur, —NH—, or —NR—, wherein R comprises alkyl, substituted alkyl, acyl, aryl, or substituted aryl;
- R₁ is a linker connecting any atom in the nicotine residue to polymer P₁ through G, wherein R₁ comprises substituted or unsubstituted C1-C18 alkene or alkane, substituted or unsubstituted C1-C18 alkoxy, substituted or unsubstituted alkylamino, substituted or unsubstituted alkylthio, substituted or unsubstituted aryl, substituted or unsubstituted alkylaryl, substituted or unsubstituted heterocycle or substituted or unsubstituted alkylheterocycle;
- P₂ is a second polymer covalently attached to Q; and
- n is the number of polymeric moieties of —[R₁-G-P₁-Q-P₂] connected to the nicotine residue, wherein n is an integer ranging from 1 to 12, and wherein P₁ and P₂ are different.

2. A method comprising: administering the compound of claim 1 to a subject.

3. A vaccine comprising: the compound of claim 1, and a synthetic nanocarrier.

4. A method comprising: administering the vaccine of claim 3 to a subject.

5. A composition comprising the compound of claim 1 and a pharmaceutically acceptable excipient.

6. The compound of claim 1, wherein P₁ comprises monomeric residues of unsubstituted or substituted ethylene oxide.

7. The compound of claim 6, wherein the ethylene oxide is substituted with $C_1$-$C_6$ alkyl or aryl.

8. The compound of claim 1, wherein P₁ comprises monomeric residues of unsubstituted or substituted ethylene sulfide.

9. The compound of claim 8, wherein the ethylene sulfide is substituted with $C_1$-$C_6$ alkyl or aryl.

10. The compound of claim 1, wherein P₁ comprises monomeric residues of unsubstituted or substituted ethyleneimine.

11. The compound of claim 10, wherein the ethyleneimine is substituted with $C_1$-$C_6$ alkyl or aryl.

12. The compound of claim 1, wherein P₁ possesses a number average molecular weight ranging from 2 kilodalton to 10 kilodalton, as determined by nuclear magnetic resonance.

13. The compound of claim 1, wherein P₂ comprises a biodegradable polymer.

14. The compound of claim 1, wherein P₂ comprises polyester, polyamide, polycarbonates, polyanhydrides, polyketals or co-polymers thereof.

15. The compound of claim 14, wherein the polyester comprises polylactide, polyglycolide, polycaprolactone, polylactide-co-glycolide, or co-polymers thereof.

16. The compound of claim 14, wherein the polyamide comprises polycaprolactam.

17. The compound of claim 1, wherein P₂ possesses a number average molecular weight ranging from 10 kilodaltons to 100 kilodaltons, as determined by nuclear magnetic resonance.

18. The compound of claim 1, wherein G comprises oxygen.

19. The compound of claim 1, wherein G comprises sulfur.

20. The compound of claim 1, wherein G comprises —NR—.

21. The compound of claim 1, wherein Q comprises oxygen.

22. The compound of claim 1, wherein Q comprises sulfur.

23. The compound of claim 1, wherein Q comprises nitrogen.

24. The compound of claim 1, wherein n is an integer ranging from 1 to 12.

25. The compound of claim 24, wherein n ranges from 1 to 5.

26. The compound of claim 25, wherein n ranges from 1 to 2.

27. The compound of claim 26, wherein n equals 1.

28. The compound of claim 1, wherein R₁ comprises —CH₂—, G and Q comprise oxygen, P₁ comprises a polymer that comprises monomeric residues of unsubstituted ethylene oxide; P₂ comprises polylactide, and n equals 1.

29. The compound of claim 1, wherein the nicotine residue comprises optically pure (+)-(2'R, 3'R) or (−)-(2'S, 3'S)- hydroxylmethyl nicotine derivatives.

* * * * *